(12) United States Patent
Shi et al.

(10) Patent No.: US 10,098,333 B2
(45) Date of Patent: Oct. 16, 2018

(54) METHOD FOR TREATING AN SLE-LIKE AUTOIMMUNE DISEASE IN A HUMAN SUBJECT CONSISTING OF ADMINISTERING STEM CELLS FROM HUMAN EXFOLIATED DECIDUOUS TEETH (SHED) AND ERYTHROPOIETIN (EPO) TO SAID HUMAN SUBJECT

(75) Inventors: Songtao Shi, Irvine, CA (US); Takayoshi Yamaza, Pasadena, CA (US); Kentaro Akiyama, Fukuoka (JP)

(73) Assignee: University Of Southern California, Los Angeles, CA (US)

( * ) Notice: Subject to any disclaimer, the term of this patent is extended or adjusted under 35 U.S.C. 154(b) by 915 days.

(21) Appl. No.: 13/133,638

(22) PCT Filed: Dec. 9, 2009

(86) PCT No.: PCT/US2009/067398
§ 371 (c)(1),
(2), (4) Date: Jul. 28, 2011

(87) PCT Pub. No.: WO2010/068707
PCT Pub. Date: Jun. 17, 2010

(65) Prior Publication Data
US 2011/0283371 A1    Nov. 17, 2011

Related U.S. Application Data

(60) Provisional application No. 61/121,081, filed on Dec. 9, 2008, provisional application No. 61/180,042, filed on May 29, 2009, provisional application No. 61/228,905, filed on Jul. 27, 2009.

(51) Int. Cl.
*C12N 5/077* (2010.01)
*A01K 67/027* (2006.01)

(52) U.S. Cl.
CPC .... *A01K 67/0275* (2013.01); *A01K 2227/105* (2013.01); *A01K 2267/03* (2013.01)

(58) Field of Classification Search
CPC .......... A01K 67/0275; A01K 2227/105; A01K 2267/03
See application file for complete search history.

(56) References Cited

U.S. PATENT DOCUMENTS

| | | | |
|---|---|---|---|
| 2002/0044923 A1* | 4/2002 | Mosca et al. | 424/93.21 |
| 2002/0064519 A1* | 5/2002 | Bruder | C12N 5/0663 424/93.1 |
| 2005/0239897 A1* | 10/2005 | Pittenger et al. | 514/569 |
| 2006/0089309 A1* | 4/2006 | Tucker | A61K 38/2257 514/10.1 |
| 2007/0258957 A1* | 11/2007 | Bowermaster | C12N 5/0607 424/93.7 |
| 2009/0324609 A1* | 12/2009 | Lodie et al. | 424/158.1 |

FOREIGN PATENT DOCUMENTS

| WO | WO 02/40061 A2 | 5/2002 | |
|---|---|---|---|
| WO | WO 2008036374 A2 * | 3/2008 | ............. A61K 35/28 |

OTHER PUBLICATIONS

Shi et al. "Bone formation by human postnatal bone marrow stromal stem cells is enhanced by telomerase expression." Nature Biotechnology(2002); 20:pp. 587-591.*
Wei et al. "Mesenchymal stem cells: a new trend for cell therapy." Acta Pharmacol Sin. Jun. 2013;34(6):747-54.*
Koc et al. "Allogeneic mesenchymal stem cell infusion for treatment of metachromatic leukodystrophy (MLD) and Hurler syndrome (MPS-IH)." Bone Marrow Transplant. Aug. 2002;30(4):215-22.*
Li et al. "Human mesenchymal stem cells inhibit metastasis of a hepatocellular carcinoma model using the MHCC97-H cell line." Cancer Sci. Dec. 2010;101(12):2546-53.*
Yin et al. "Bone marrow mesenchymal stromal cells to treat tissue damage in allogeneic stem cell transplant recipients: correlation of biological markers with clinical responses." Stem Cells. May 2014;32(5):1278-88.*
Miura et al. "SHED: stem cells from human exfoliated deciduous teeth." Proc Natl Acad Sci U S A. May 13, 2003;100(10):5807-12. Epub Apr. 25, 2003.*
Sun et al. "Allogenic bone marrow derived mesenchymal stem cells transplantation for refractory systemic lupus erythematosus." Arthritis & Rheumatism, (Sep. 2008) vol. 58, No. 9, Suppl. S, pp. S925.*
Sun et al. "Mesenchymal Stem Cells Transplantation for Refractory Systemic Lupus Erythematosus (SLE)". acessed from https://clinicaltrials.gov/ct2/show/NCT00698191 on Oct. 25, 2016.*
International preliminary report on patentability dated Jun. 14, 2011 for corresponding PCT application PCT/US2009/067398.

(Continued)

*Primary Examiner* — Titilayo Moloye
(74) *Attorney, Agent, or Firm* — McDermott Will & Emery LLP

(57) ABSTRACT

This invention discloses a stem cell modified animal model useful as a research tool for investigating aging-related degeneration processes and treatments. The animal model is preferably a rodent subcutaneously transplanted with a mesenchymal stem cell capable of generating a functional bone or marrow element. Also provided are a method for extending the lifespan and improving the quality of life of a subject by subcutaneously transplanting a plurality of mesenchymal stem cells to the subject, wherein the mesenchymal stem cells are capable of generating a functional bone or marrow element. Compositions and source of stem cells suitable for use with the methods of this invention, including stem cells from human exfoliated deciduous teeth (SHED), are also disclosed. Further disclosed is a method for identifying progenitor bone marrow mesenchymal stem cells, and a method for treating SLE-like autoimmune diseases by infusion of mesenchymal stem cells.

15 Claims, 28 Drawing Sheets
Specification includes a Sequence Listing.

(56) References Cited

OTHER PUBLICATIONS

Dianji Fang et al., "Transplantation of Mesenchymal Stem Cells Is an Optimal Approach for Plastic Surgery", Stem Cells, vol. 25, Dec. 14, 2006, pp. 1021-1028, XP-002576245.

Yasuo Miura et al., "Mesenchymal Stem Cell-Organized Bone Marrow Elements: An Alternative Hematopoietic Progenitor Resource", Stem Cells, vol. 24, No. 11, Nov. 1, 2006, pp. 2428-2436, XP-002576246.

Kevin J. Zwezdaryk et al., "Erythropoietin, a Hypoxia-regulated Factor, Elicits a Pro-Angiogenic Program in Human Mesenchymal Stem Sells", Exp Hematol, vol. 35, No. 4, Apr. 1, 2007, pp. 640-652, XP-002576247.

Elise Esneault et al., "Combined Therapeutic Strategy Using Erythropoietin and Mesenchymal Stem Cell Potentiates Neurogenesis After Transient Focal Cerebral Ischemia in Rats", J Cereb. Blood Flow Metab., vol. 28, No. 9, May 14, 2008, pp. 1552-1563 XP-002576248.

Ian B. Copland et al., "Coupling Erythropoietin Secretion to Mesenchymal Stromal Cells Enhances Their Regenerative Properties", Cardiovasc Res., vol. 79, No. 3, Apr. 8, 2008, pp. 405-415, XP-002576249.

Michael R. Ward et al., "Erythropoietin and Mesenchymal Stromal Cells in Angiogenesis and Myocardial Regeneration: One Plus One Equals Three?", Cardiovasc. Res., vol. 79, No. 3, Jun. 11, 2008, pp. 357-359, XP-002576250.

Takayoshi Yamaza et al., "Mesenchymal Stem Cell-Mediated Ectopic Hematopoiesis Alleviates Aging-Related Phonotype in Immunocompromised Mice", Blood, vol. 113, No. 11, Mar. 12, 2009, pp. 2595-2604, XP-002576251.

Lingyun Sun et al., Mesenchymal Stem Cell Transplantation Reverse Multiorgan Dysfunction in Systemic Lupus Erythematosus Mice and Humans:, Stem Cell, vol. 27, No. 6, Mar. 19, 2009, pp. 1421-1432, XP-002576252.

Il-Hyuk Chung et al., "Stem Cell Property of Postmigratory Cranial Neural Crest Cells and Their Utility in Alveolar Bone Regeneration and Tooth Development", Stem Cells, vol. 27, No. 4, Sep. 20, 2009, pp. 866-877, XP-002576253.

* cited by examiner

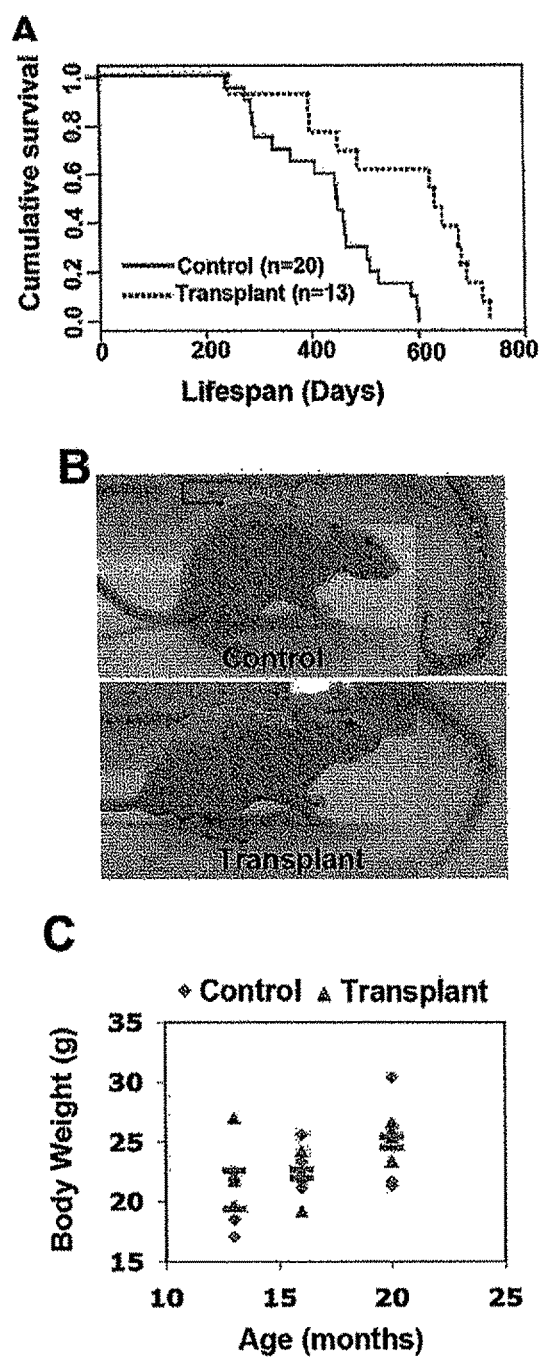
Figure 1A – C

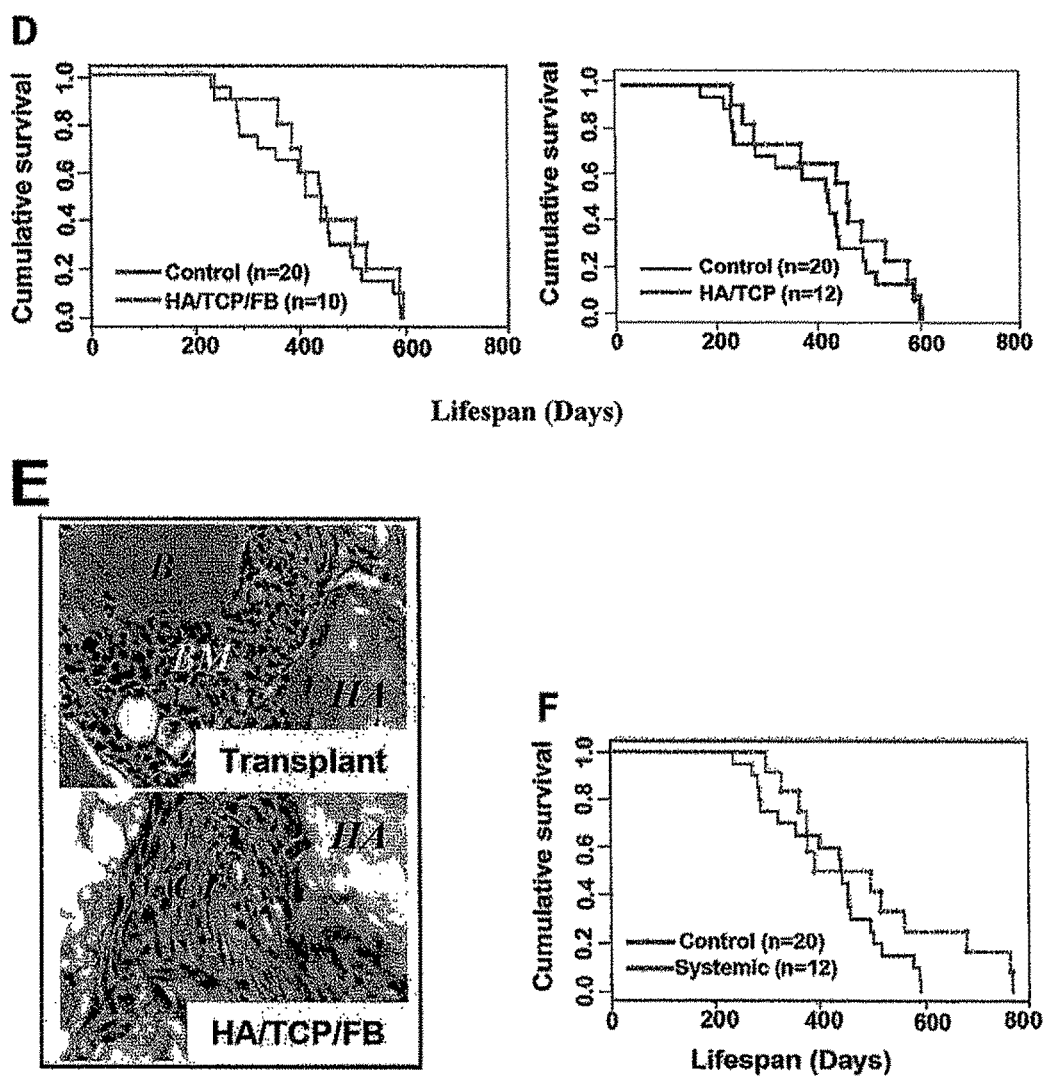
Figure 1D – F

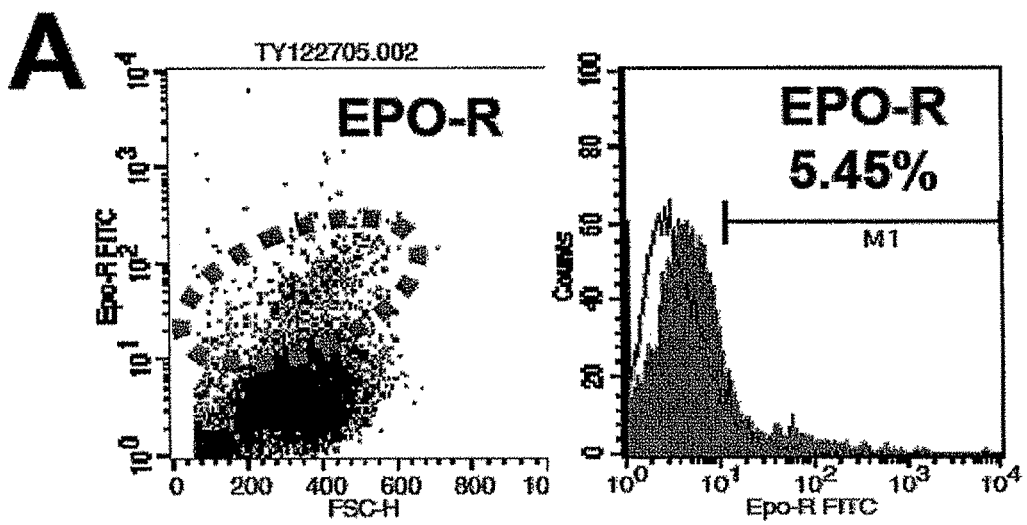
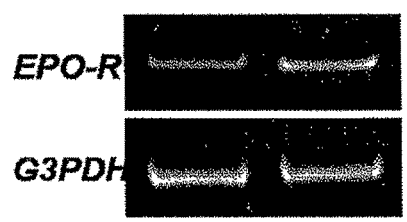
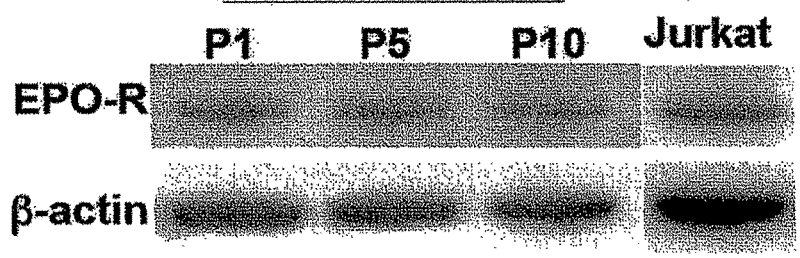
Figure 2A – C

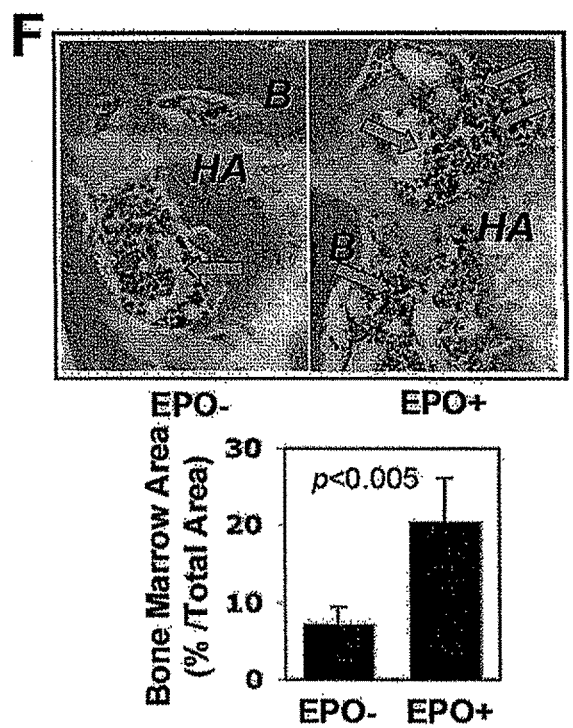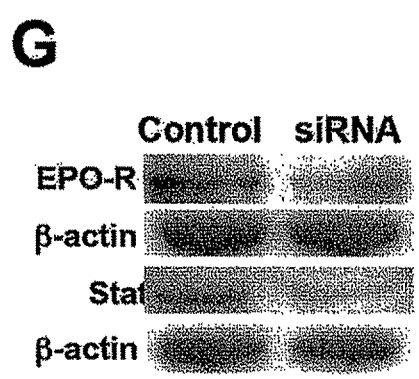
Figure 2F – G

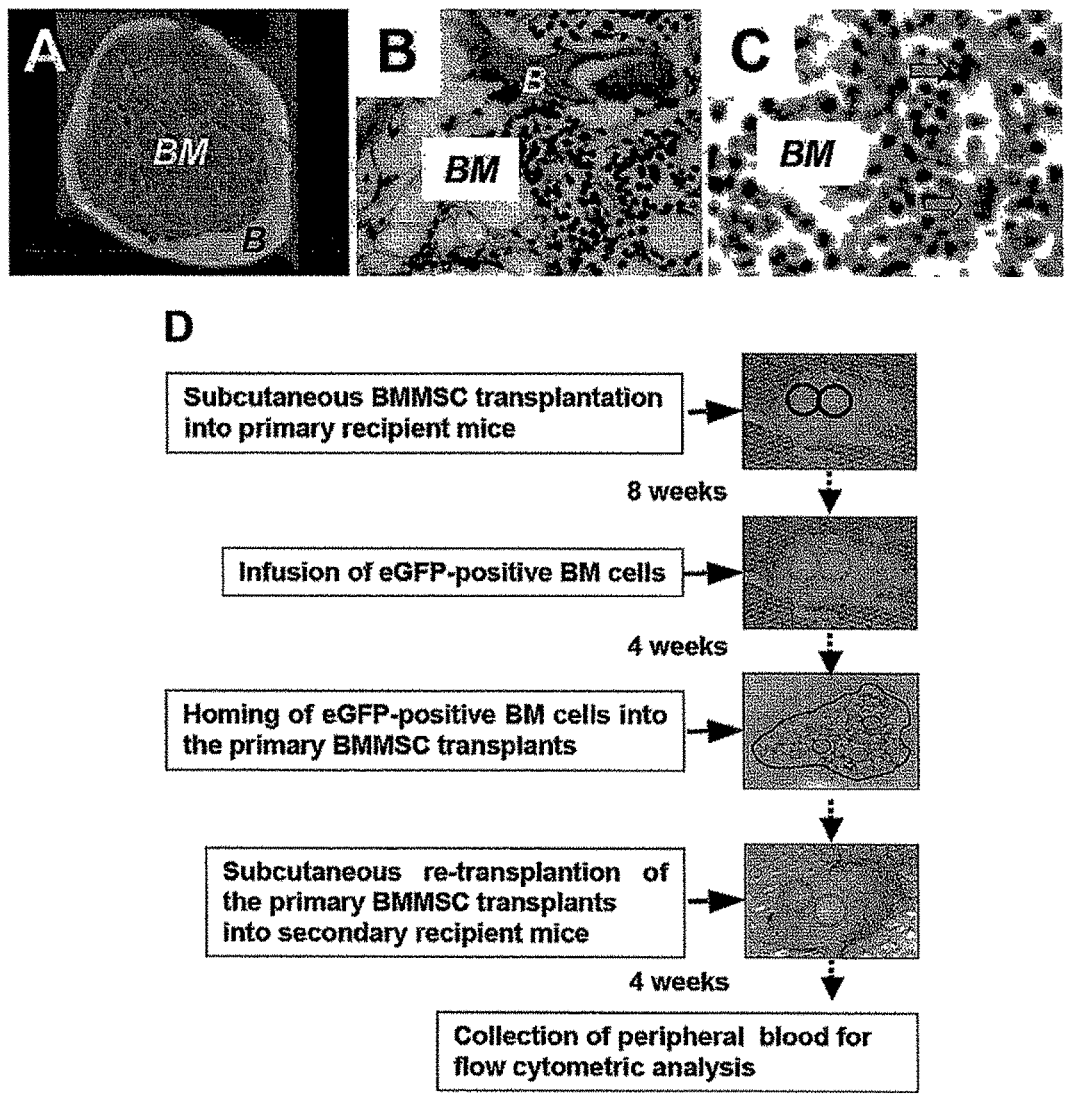
Figure 3A – D

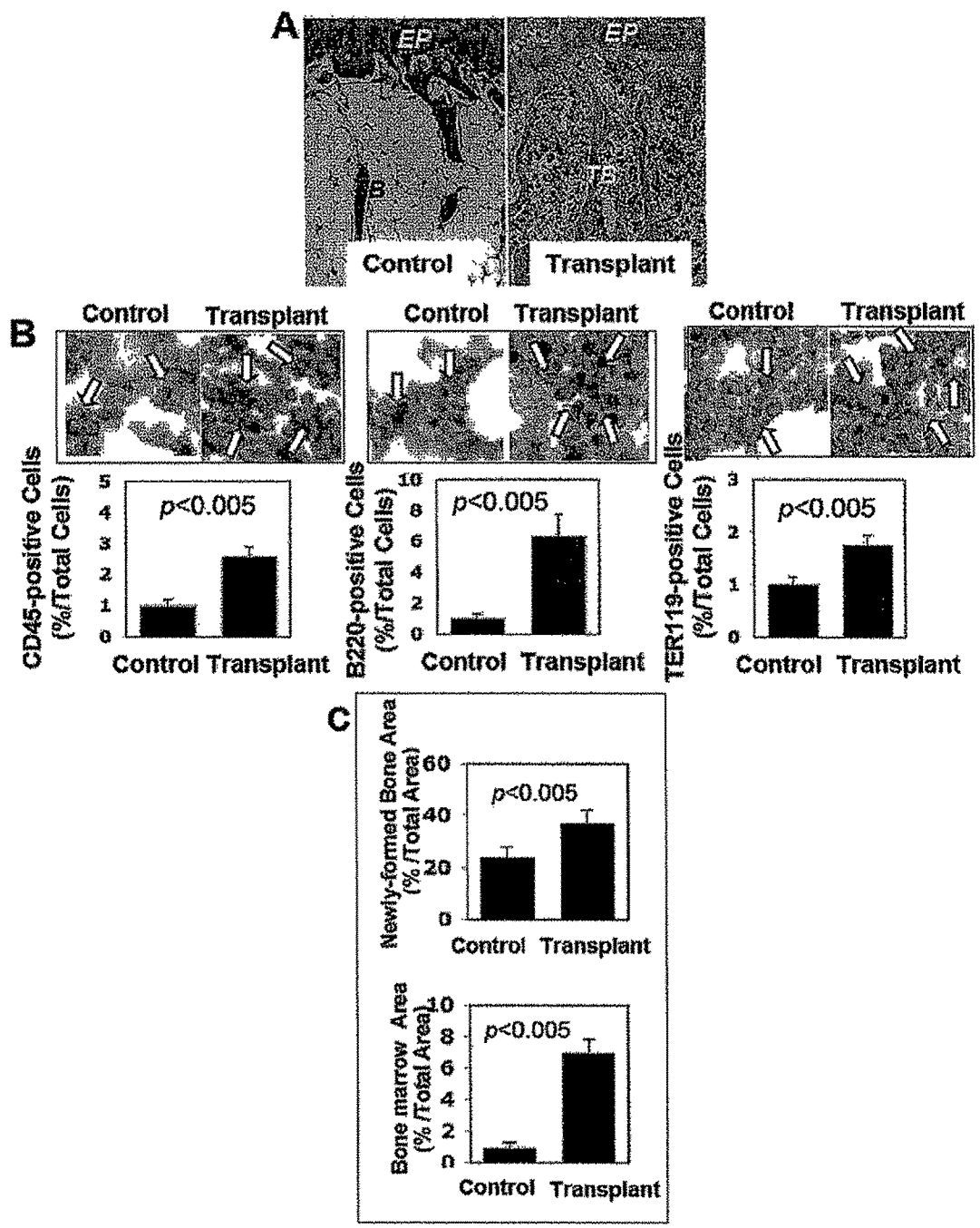
Figure 4A – C

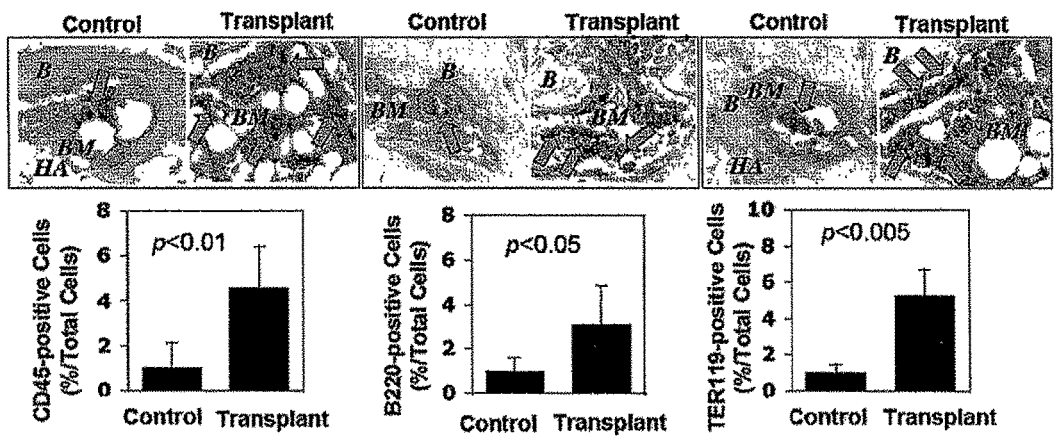
Figure 4D
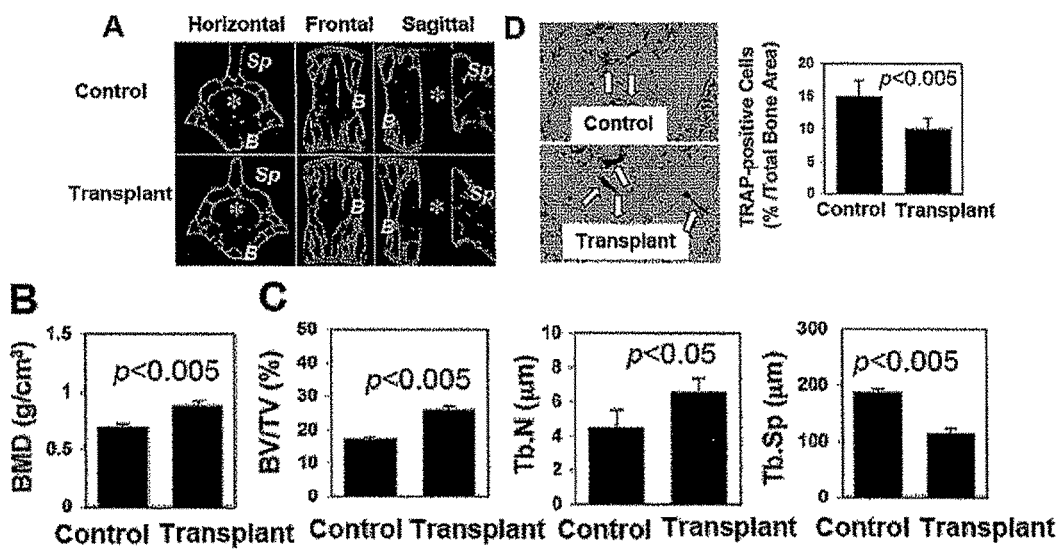
Figure 5 A - D

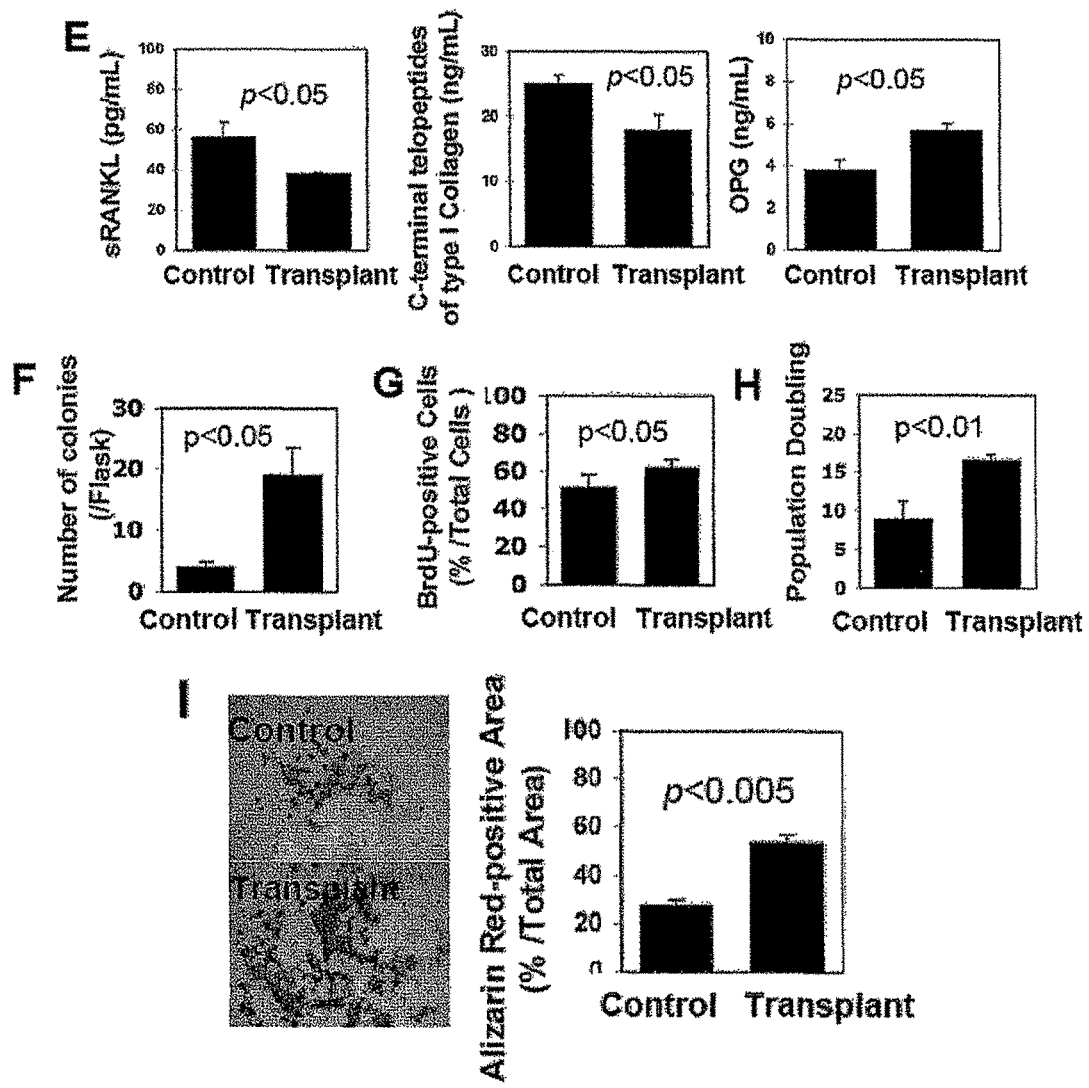
Figure 5E-I

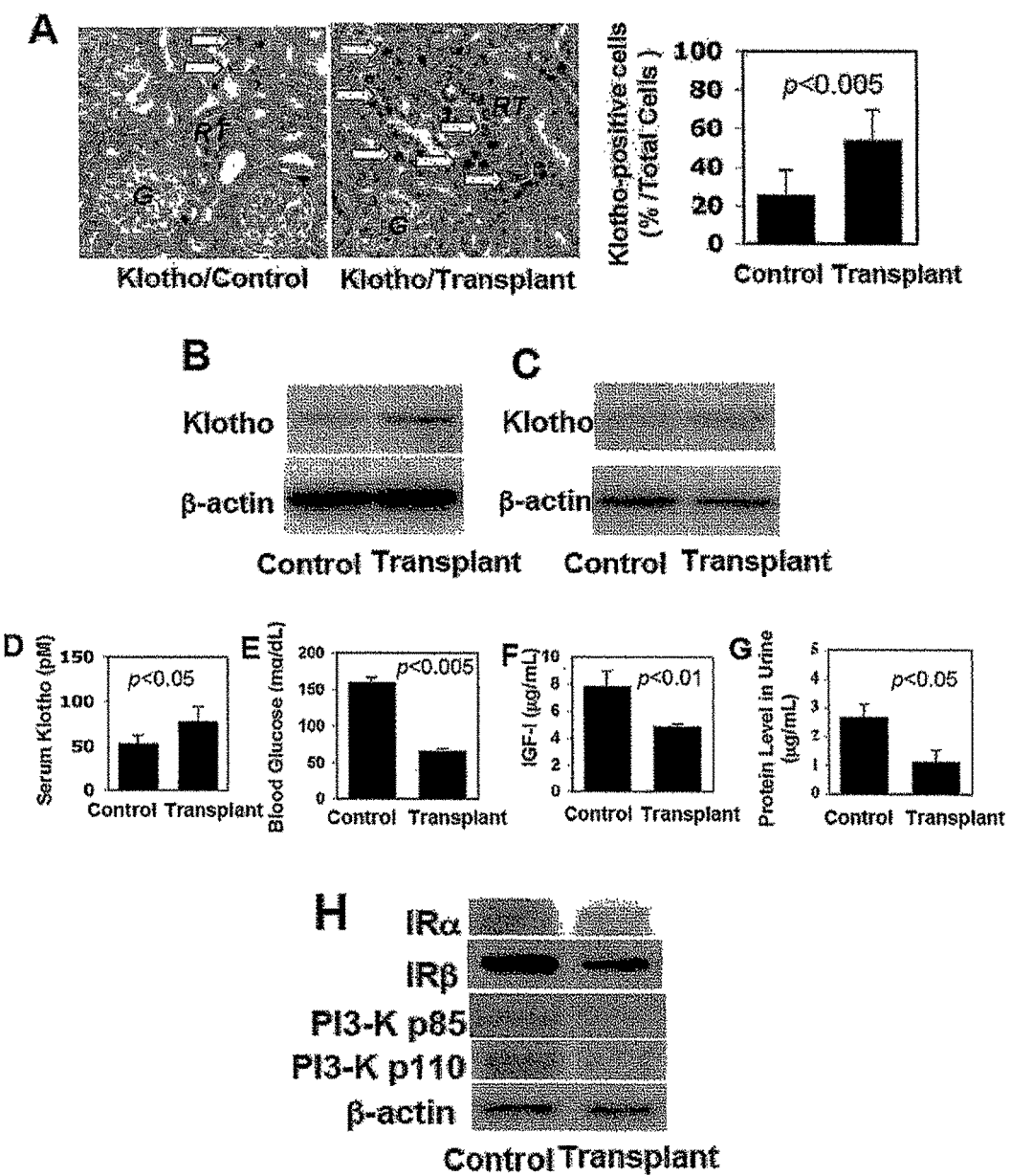
Figure 6A – H

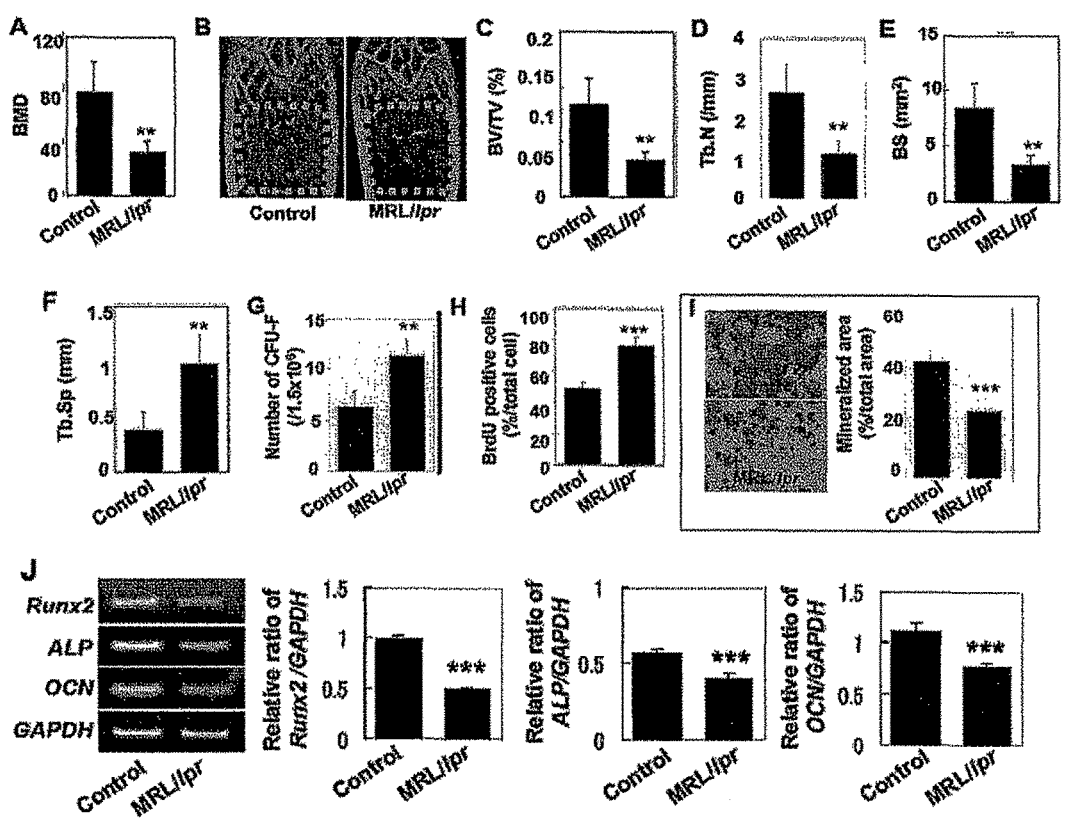
Figure 7A - J

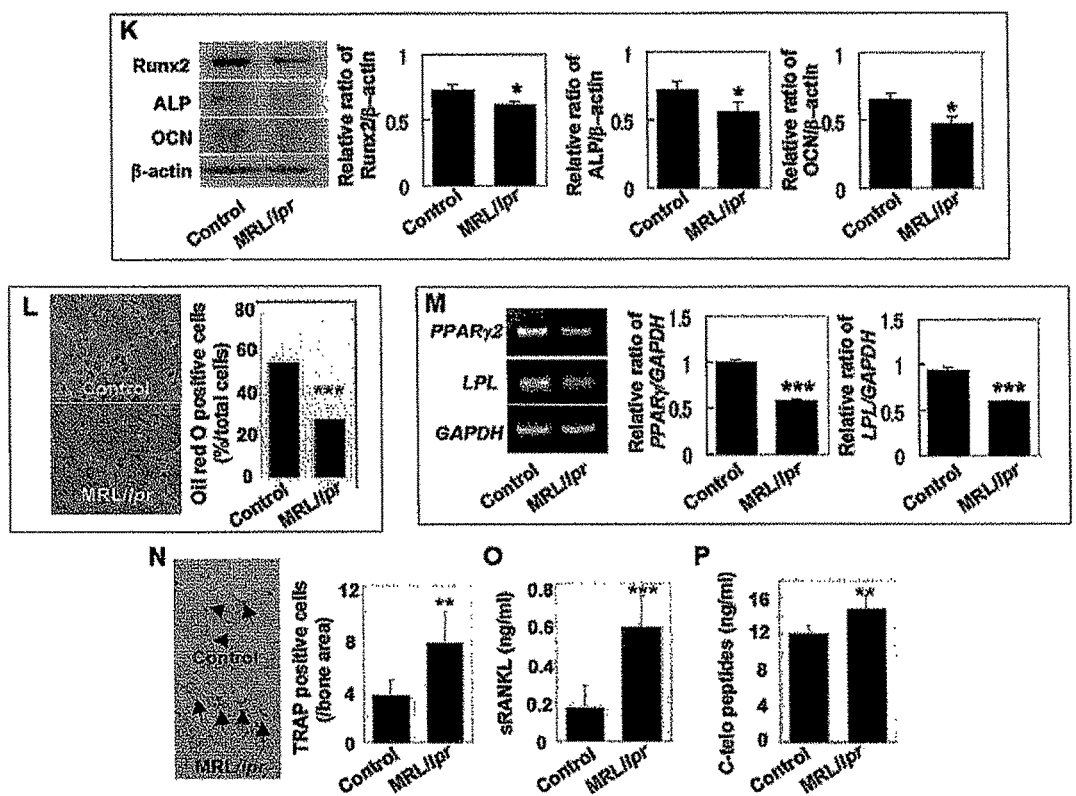
Figure 7K - P

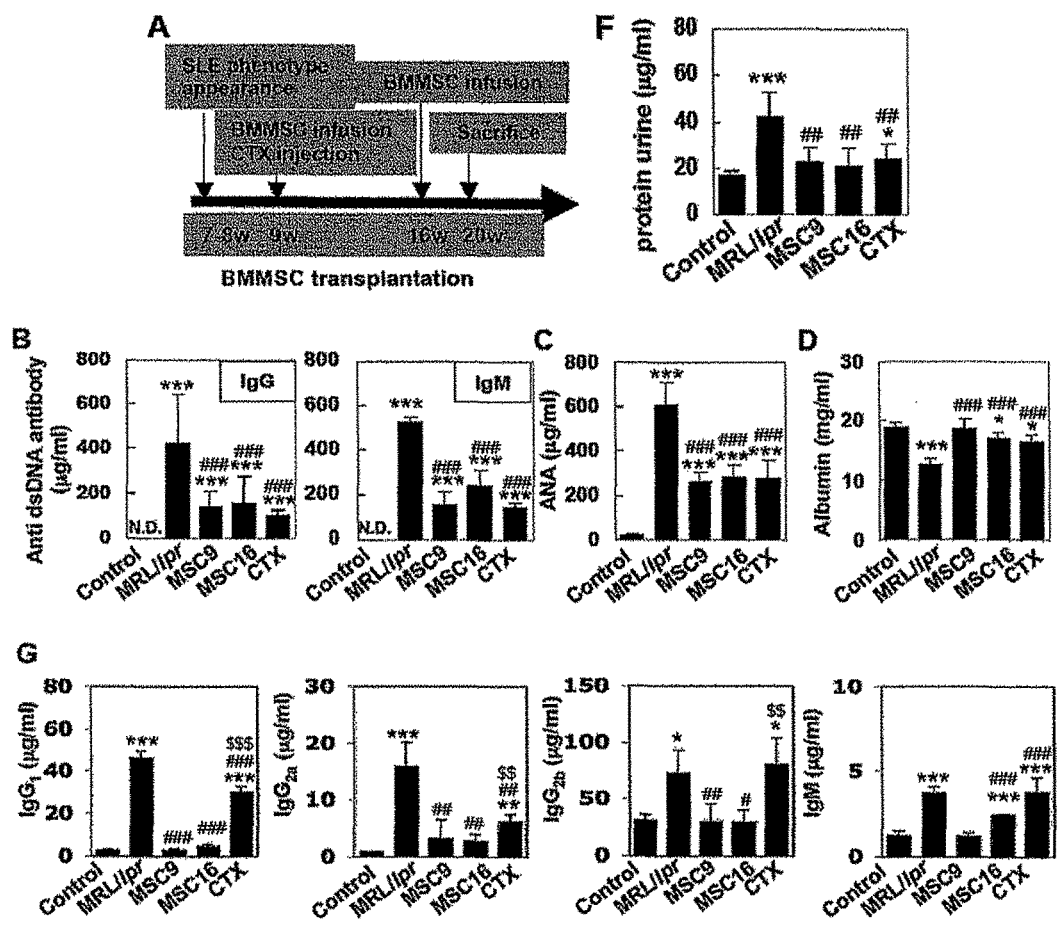
Figure 8A –D and F – G

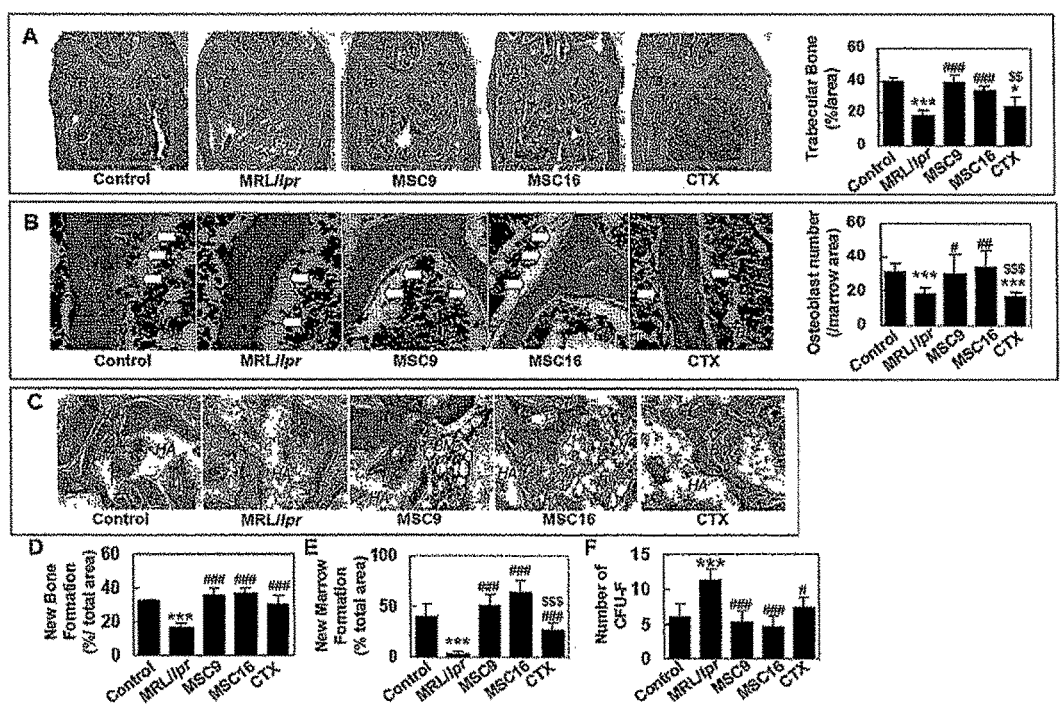
Figure 9A - F

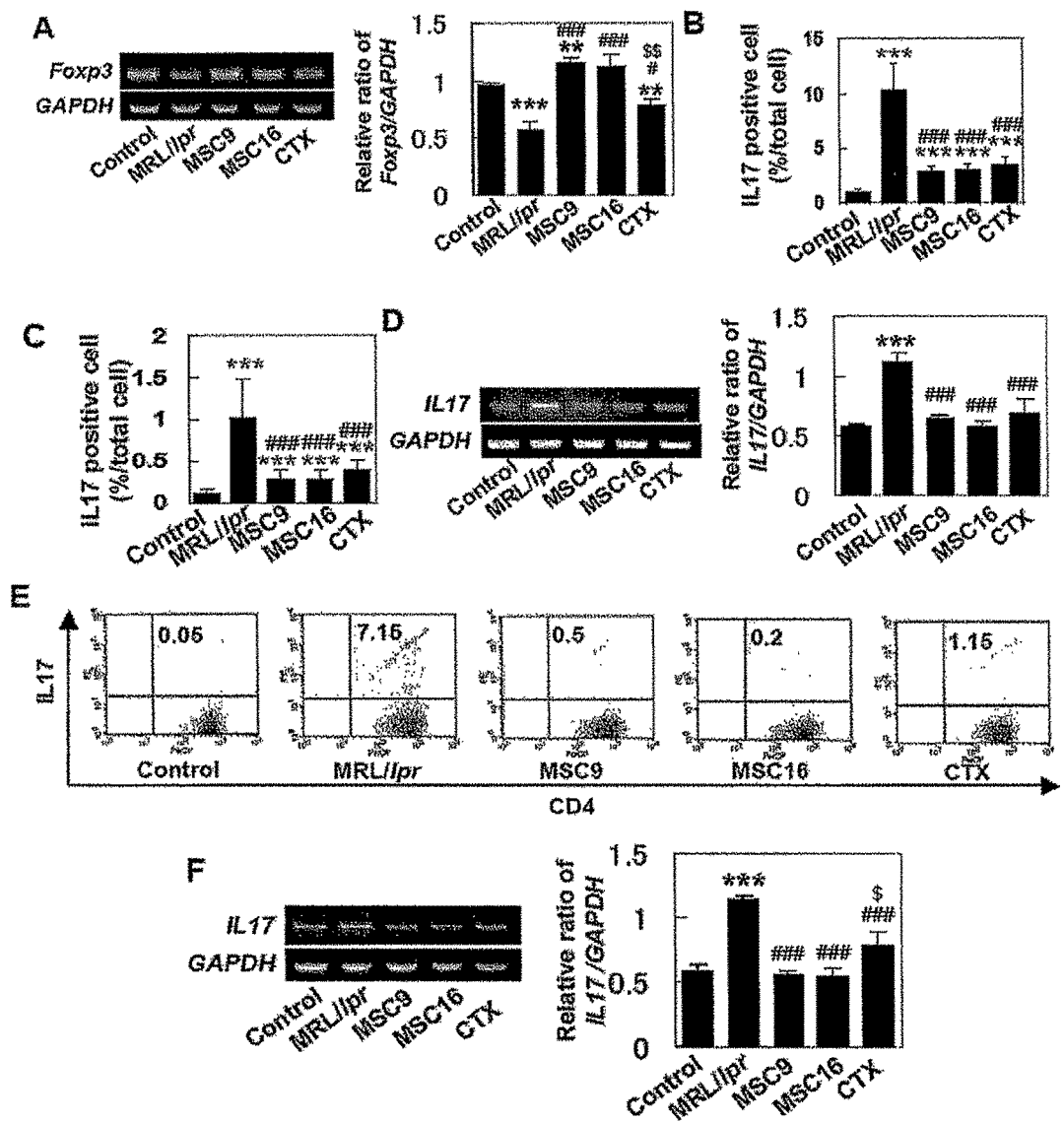
Figure 10A - F

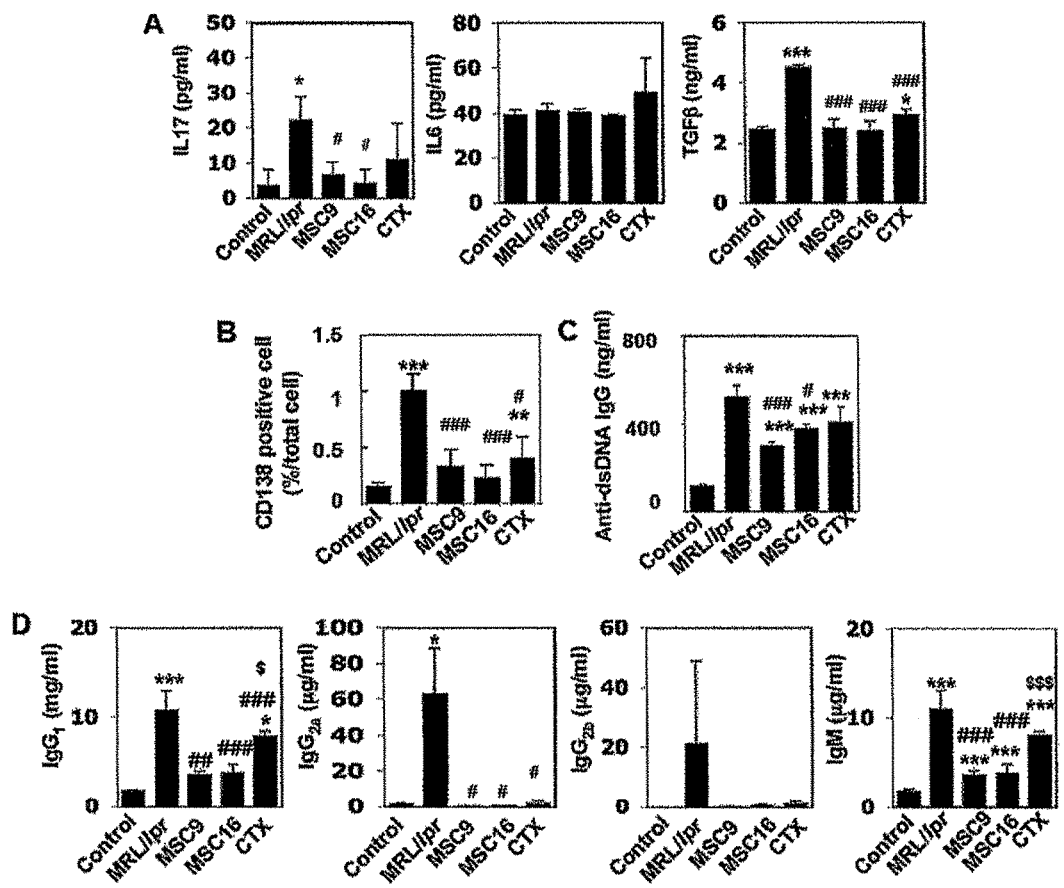
Figure 11A - D

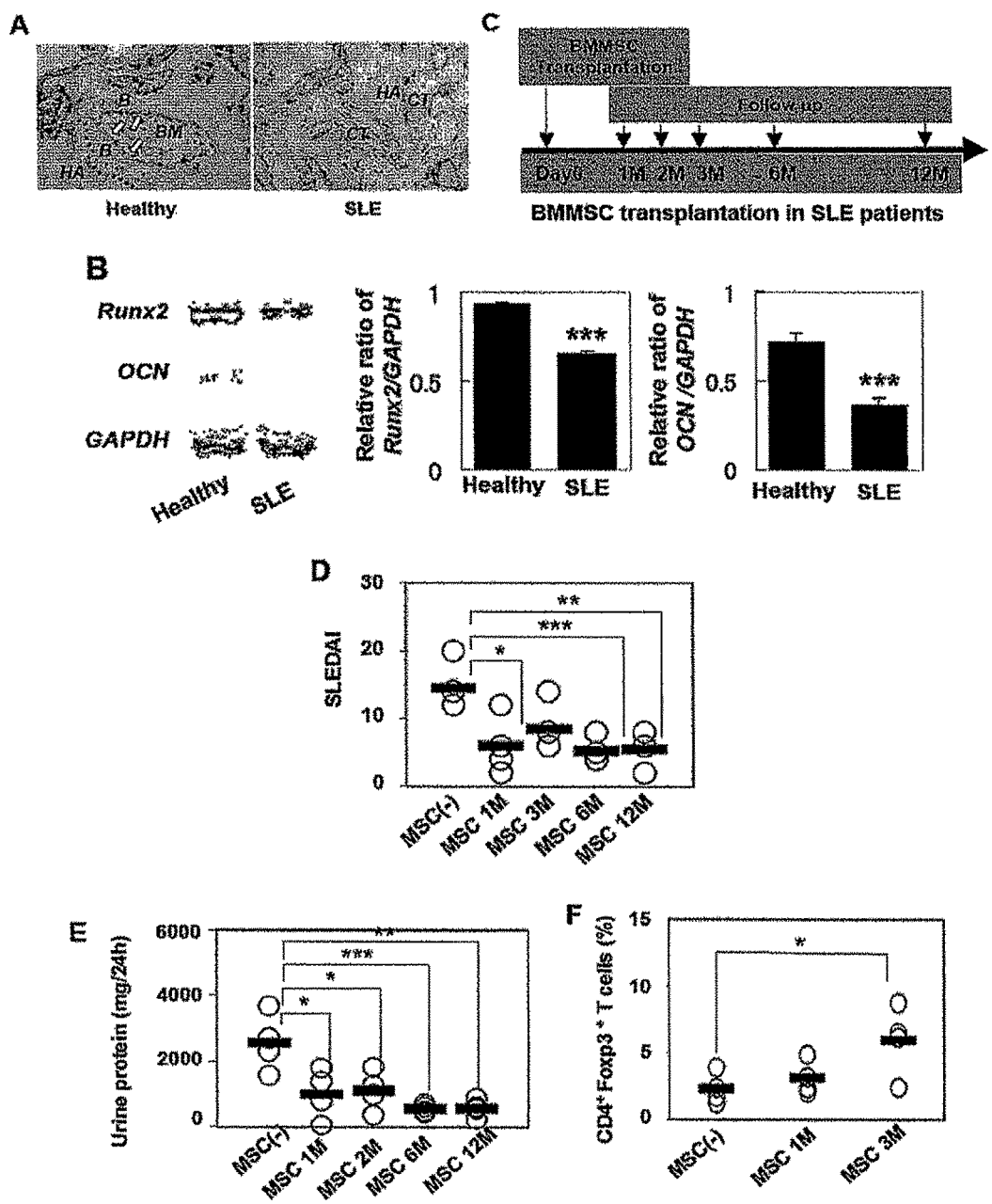
Figure 12A - F

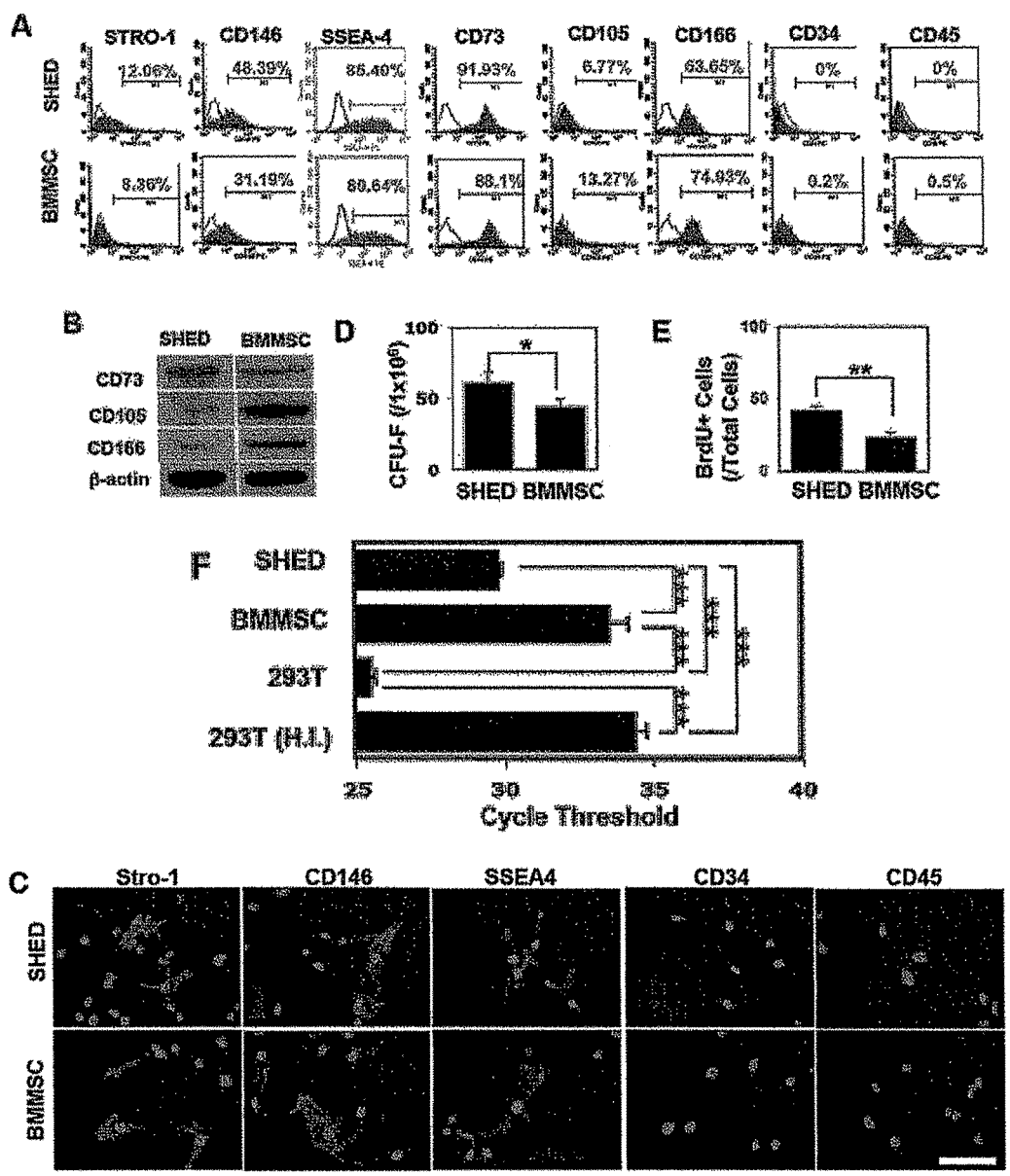
Figure 13A - F

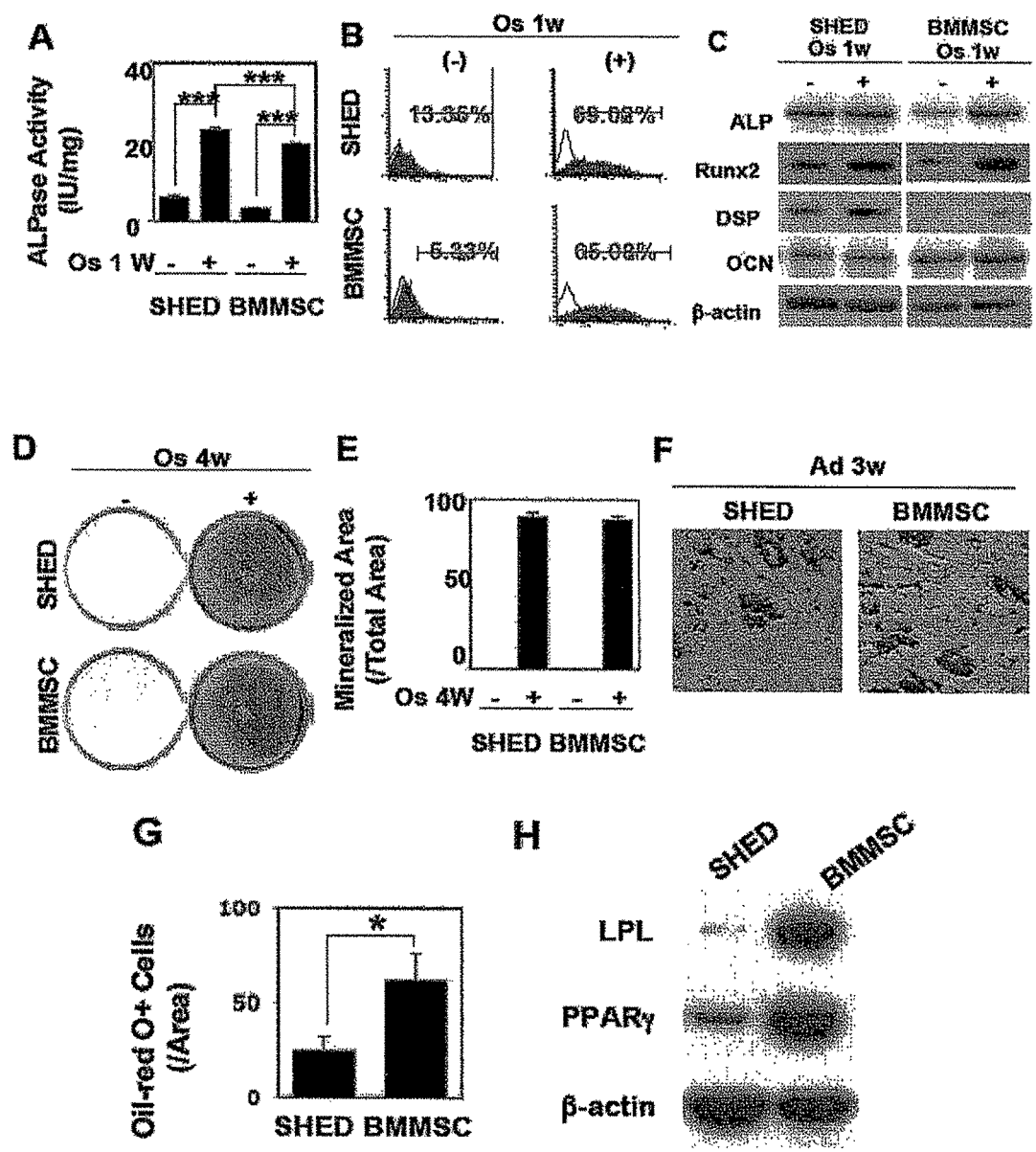
Figure 14A – H

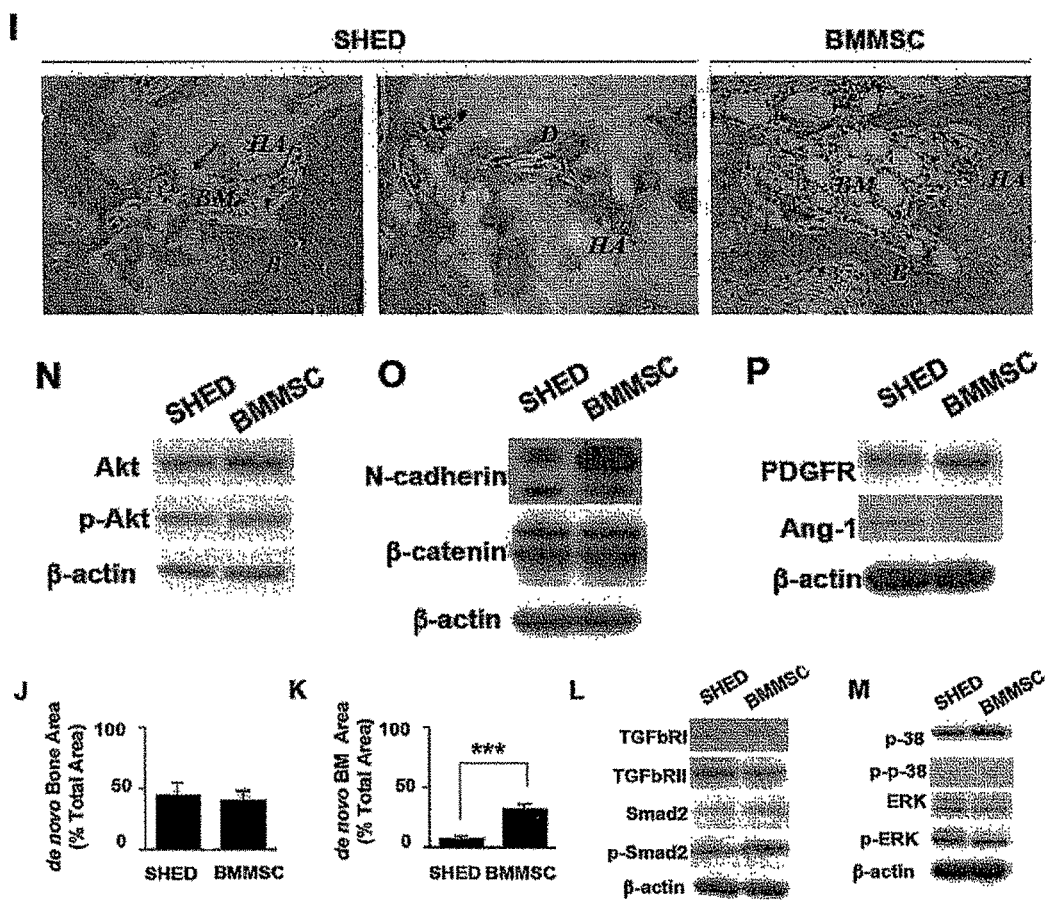
Figure 14 I-P

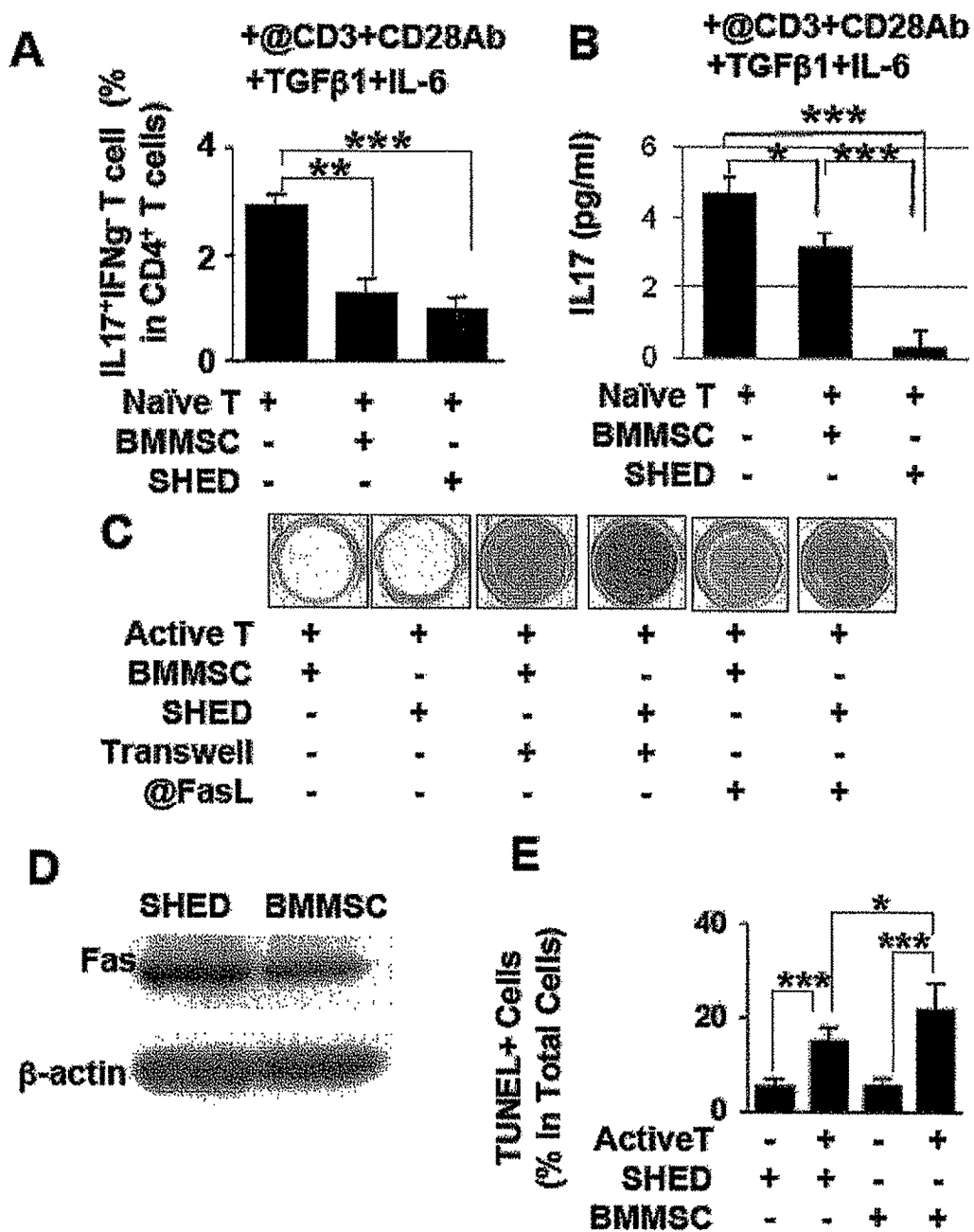
Figure 15A - E

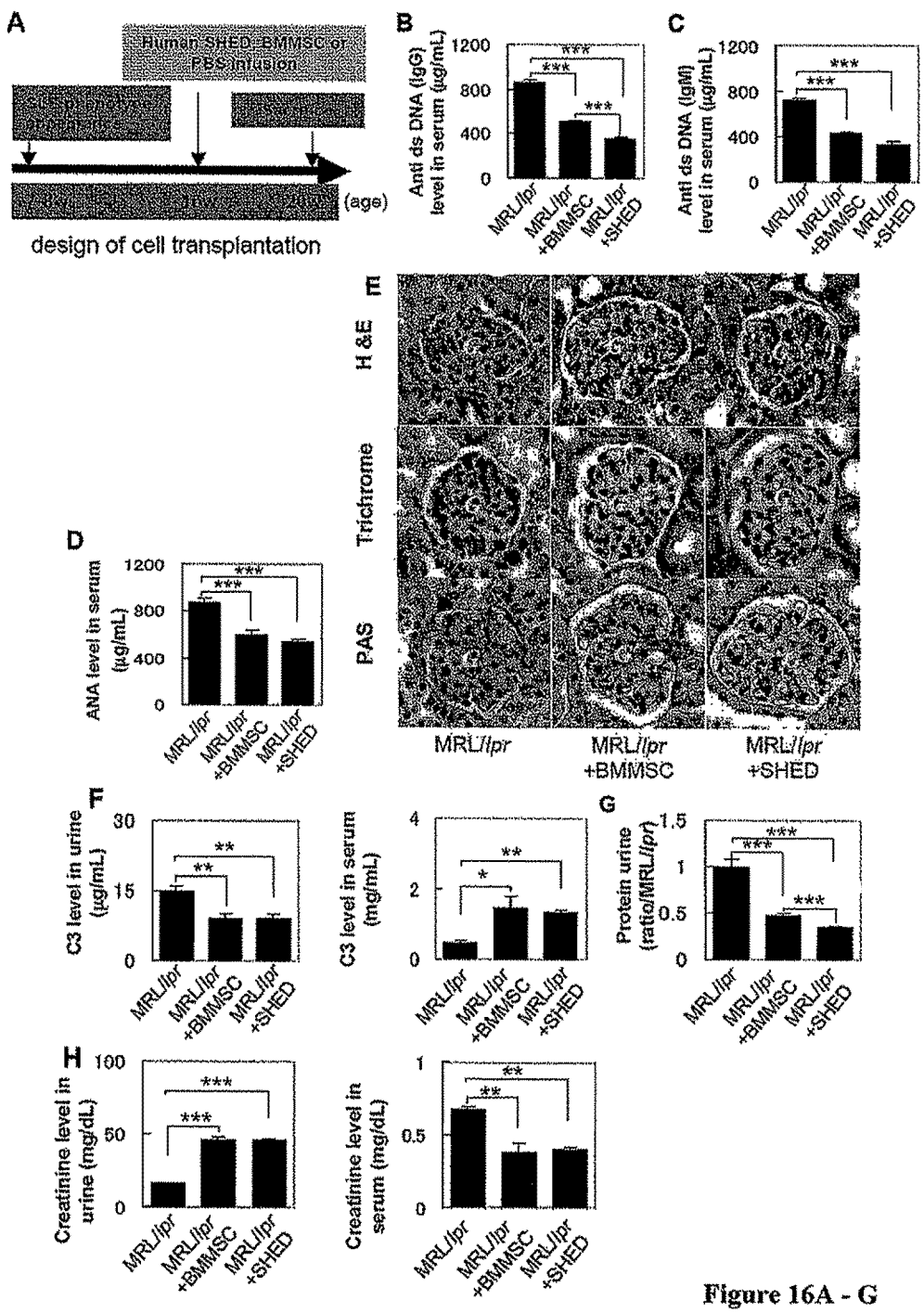
Figure 16A - G

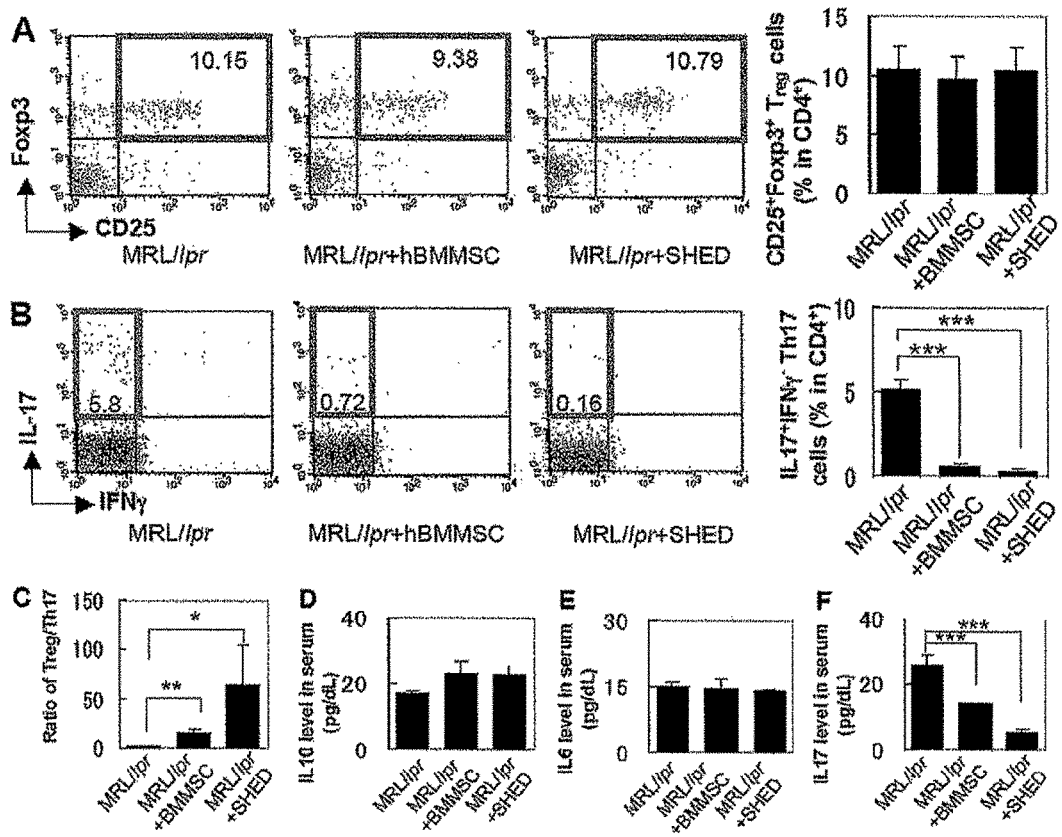
Figure 17A - F

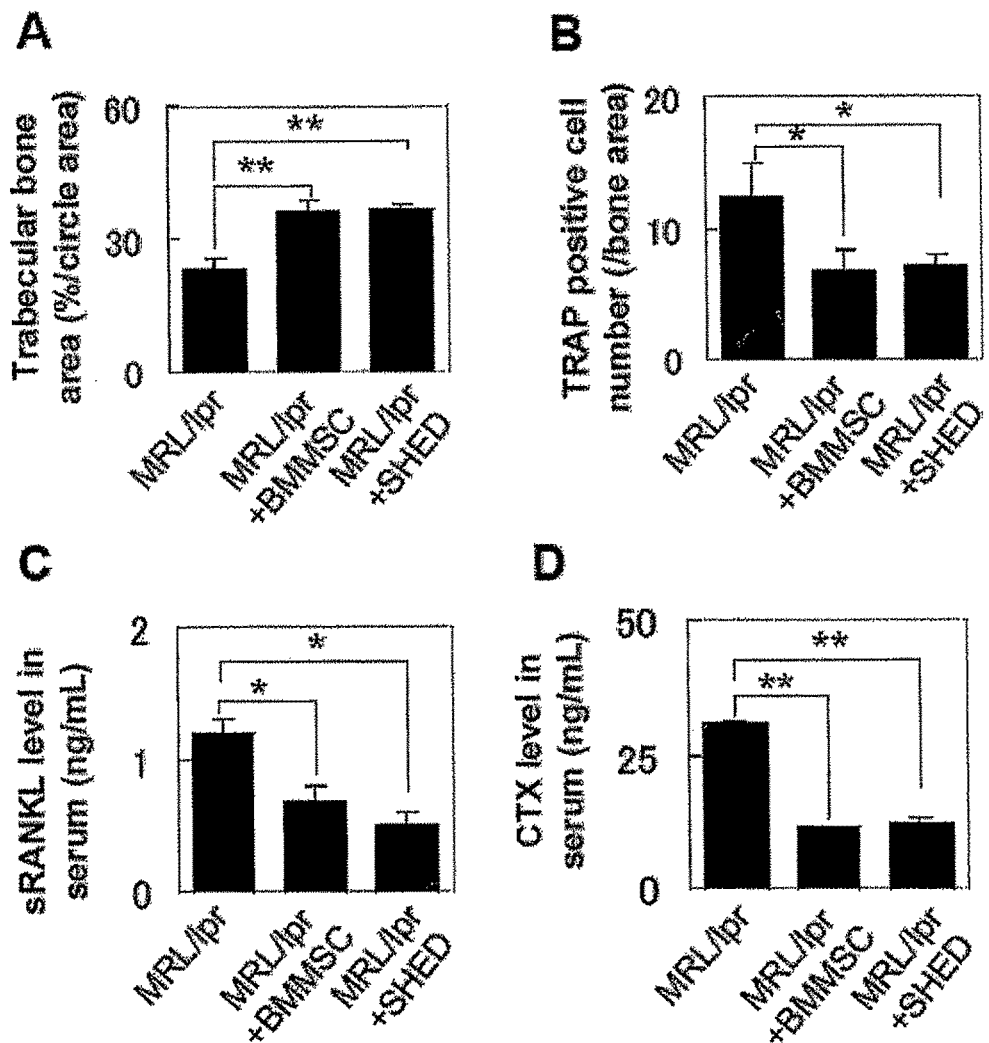
Figure 18A - D

```
                        SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
tactcaaagc tggcagcaga                                              20

<210> SEQ ID NO 2
<211> LENGTH: 20
<212> TYPE: DNA
<213> ORGANISM: Homo sapiens

<400> SEQUENCE: 2
tactcaaagc tggcagcaga                                              20

<210> SEQ ID NO 3
<211> LENGTH: 20
<212> TYPE: DNA
<213> ORGANISM: Homo sapiens

<400> SEQUENCE: 3
ctggcctcca gctacatctc                                              20

<210> SEQ ID NO 4
<211> LENGTH: 21
<212> TYPE: DNA
<213> ORGANISM: Homo sapiens

<400> SEQUENCE: 4
tcatatttgg caggtttttc t                                            21
```

METHOD FOR TREATING AN SLE-LIKE AUTOIMMUNE DISEASE IN A HUMAN SUBJECT CONSISTING OF ADMINISTERING STEM CELLS FROM HUMAN EXFOLIATED DECIDUOUS TEETH (SHED) AND ERYTHROPOIETIN (EPO) TO SAID HUMAN SUBJECT

CROSS-REFERENCE TO RELATED APPLICATIONS

This application claims the benefit of U.S. Provisional Application No. 61/121,081, filed on Dec. 9, 2009, 61/180, 042, filed on May 20, 2009, and 61/228,905, filed on Jul. 27, 2009. These applications are incorporated herein by reference.

STATEMENT REGARDING FEDERALLY SPONSORED RESEARCH OR DEVELOPMENT

This invention was made with government support under Contract No. RO1DE17449 and 1R01DE019413 awarded by National Institutes of Health and RN1-00572 awarded by the California Institute for Regenerative Medicine. The government has certain rights in the invention.

FIELD OF THE INVENTION

The present invention relates generally to the field of stem cell therapy and therapeutics. In particular, this invention pertains to a novel stem cell modified animal model for aging-related degenerations. This invention also relates to stem cell based methods and compositions for extending lifespan, improving quality of life, and treating autoimmune diseases such as systemic lupus erythematosus (SLE) using bone marrow mesenchymal stein cells (BMMSCs) and stem cells from human exfoliated deciduous teeth (SHED).

SEQUENCE LISTING

A Sequence Listing, comprising SEQ ID NO: 1 to SEQ ID NO 4, are included as a Table titled "sequence listing."

BACKGROUND OF THE INVENTION

Stem cells are cells found in most, if not all, multi-cellular organisms. They are characterized by the ability to renew themselves through mitotic cell division and differentiating into diverse range of specialized cell types. The two broad types of mammalian stem cells are embryonic stem cells that are isolated from the inner cell mass of blastocytes, and adult stem cells that are found in adult tissues. In a developing embryo, stem cells can differentiate into all of the specialized embryonic tissues. In adult organisms, stem cells and progenitor cells act as a repair system for the body, replenishing specialized cells and also maintaining the normal turnover of regenerative organs such as blood, skin or intestinal tissues.

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending on various influences from bioactive factors, such as cytokines. Functionally speaking, stem cells have the ability to regenerate tissue over a lifetime. For example, the "gold standard" test for a bone marrow or hematopoietic stem cell (HSC) is the ability of the subject cell to rescue an individual who is without HSCs when the subject cell is transplanted to the individual. In this case, a stem cell must be able to produce new blood cells and immune cells over a long term, demonstrating potency. It should also be possible to isolate stem cells from the transplanted individual, which can themselves be transplanted into another individual without HSCs, demonstrating that the stem cell was able to self-renew.

Properties of stem cells can be illustrated in vitro using methods such as clonogenic assays where single cells are characterized by their ability to differentiate and self-renew. However, such methods are time consuming and cumbersome. Methods based on a distinct set of cell surface markers have been adopted. Markers that are associated with identifiable cell characteristics are valuable tools.

Medical researchers believe that stem cell therapy has the potential to dramatically change the treatment of human diseases. A number of adult stem cell therapies already exist, particularly bone marrow transplants for treating leukemia. In the future, researchers imagine being able to use technologies derived from stem cell research to treat a wide variety of diseases including cancer, Parkinson's disease, spinal cord injuries, amyotrophic lateral sclerosis, multiple sclerosis, and muscle damages, just to name a few. However, there still exists a great deal of scientific and technical uncertainties surrounding stem cell research.

Therefore, there still exists a need for research tools and methods that can be used to elucidate the disease mechanisms and advance the field of stem cell therapy and therapeutics.

SUMMARY OF THE INVENTION

One aspect of this invention is the inventors' unexpected discoveries concerning the medicinal properties of certain types of stem cells including BMMSCs and SHED. In particular, the inventors have unexpectedly found that mesenchymal stem cells, when transplanted subcutaneously to a subject, will ameliorate or reverse aging-related degenerations across multiple organ systems. These mesenchymal stem cells are distinguished by their ability to generate functional bone or marrow elements in the subject. The inventors also discovered that erythropoietin receptor (EPO-R) is an early marker for the subpopulation of BMMSCs that bear this distinguishing property.

Another aspect of this invention is the discovery that BMMSC and SHED both have immune-modulation properties, thus, are useful as therapeutics in treating autoimmune diseases such as SLE.

Disclosed are various tools, methods, and compositions to take advantage of the hitherto unknown properties of the stem cells.

Accordingly, in a first embodiment, this invention provides a novel artificially modified animal useful as a research tool for studying aging-related degeneration. Animals in accordance with this aspect of the invention generally have a plurality of mesenchymal stem cells subcutaneously transplanted thereto.

In a second embodiment, this invention also provides a composition for creating an animal as described above. Compositions in accordance with this aspect of the invention generally include a plurality of mesenchymal stem cells that are capable of generating a functional bone or marrow element when subcutaneously transplanted to the animal.

In a third embodiment, this invention provides a composition for ameliorating or revering aging-related degenerations in a subject. Compositions in accordance with this aspect of the invention generally include a plurality of mesenchymal stem cells that are capable of generating a functional bone or marrow element when subcutaneously transplanted to the subject.

In a fourth embodiment, this invention provides a method for extending the lifespan and improving the quality of life of a subject. Methods in accordance with this aspect of the invention generally include the step of transplanting subcutaneously a plurality of mesenchymal stem cells to the subject wherein the stem cells are capable of generating a functional bone or marrow element in the subject.

In a fifth embodiment, this invention also provides a method for ameliorating or reversing aging-related degenerations in a subject. Methods in accordance with this aspect of the invention generally include the step of transplanting a plurality of mesencymal stem cells cells to the subject wherein the stem cells are capable of generating a functional bone or marrow element in the subject.

In a sixth embodiment, this invention provides a method of identifying human BMMSCs for generating a functional marrow element in a subject. Methods in accordance with this aspect of the invention generally include the step of screening a human BMMSC for EPO-R. If a human BMMSC is found to express EPO-R, the cell is identified as a progenitor BMMSC.

In a seventh seventh embodiment, this invention provides a method for treating an autoimmune disease in a subject. Methods in accordance with this aspect of the invention generally include the step of administering systemically to the subject a composition containing a plurality of allogenic mesenchymal stem cells, wherein the stem cells are derived from BMMSC, SHED, or a combination thereof.

Other aspects and advantages of the invention will be apparent from the following description and the appended claims.

BRIEF DESCRIPTION OF THE DRAWINGS

FIG. 1 shows data demonstrating that subcutaneous transplantation of human BMMSCs extends lifespan in immunocompromised mice. (A) Kaplan-Meier analysis of survival. Recipient mice transplanted with subcutaneous human BMMSC using hydroxyapatite tricalcium phosphate (HA/TCP) as a carrier vehicle (Transplant, n=13) manifested a significantly increased lifespan compared to age-matched control immunocompromised mice (Control, n=20) ($p<0.05$). (B) The natural aging phenotype of human kyphosis was observed in six out of nine aging control mice, shown here as extreme curvature of the vertebrae and tail however, not observed in transplant mice (n=15). (C) Body weight at indicated months showed no significant difference between control and transplant recipients. Bars represented the means. (D) When human skin fibroblasts were transplanted subcutaneously using HA/TCP as a carrier (HA/TCP/FB), there is no increased lifespan in the recipients (n=10; P=0.391). Similarly, only HA/TCP was transplanted, there is also no increased lifespan in the recipients. (E) Newly formed bone (B) and bone marrow (BM) were found in the BMMSC transplants (Transplant) at eight weeks post transplantation. However, fibroblast group (HA/TCP/FB) failed to form new tissue and only showed connective tissue (CT) around HA/TCP particles (HA) by H&E staining. (F) When human BMMSCs ($1\times10^6$) were infused into immunocompromised mice (n=12) via tail vein, there was no consistent increase in lifespan extension ($P>0.05$) as compared to the control group.

FIG. 4 shows data demonstrating that subcutaneous transplantation of human BMMSCs rescues bone marrow elements. (A) Representative femur sections showed increment of trabecular bone in three BMMSC transplant recipient mice at 16 months of age (Transplant) as compared to the untreated age-matched littermates (Control; n=3). Abundant red marrow elements, characteristic of increased hematopoietic cells, were observed in the transplant recipients as compared to the fatty, acellular marrow compartment in the control mice. EP: epiphyseal cartilage, TB: trabecular bone, asterisk: bone marrow. Original magnification: X200. (B) Immunohistochemical staining showed numerous CD45-, B220- and TER119-positive cells (open arrows) in the femur bone marrow of recipient mice (n=3) compared to the age-matched control mice (n=3). Bars showed standard deviation. (C) BMMSCs isolated from mice received subcutaneous BMMSC transplants (n=3) were transplanted into new immunocompromised recipients mice using HA/TCP as a carrier. At eight weeks post-transplantation, the transplants showed significantly increased bone (upper panel) and bone marrow (lower panel) fou nation compared to the BMMSC transplants from control mice (n=3). (D) Immunohistochemical staining showed an increased CD45-, B220- and TER119-positive cells (arrows) in the ectopic bone marrow compartment (BM) generated by BMMSCs from the mice received subcutaneous BMMSC transplants (n=3) as compared to the ectopic bone marrow compartment generated by BMMSCs from regular mice (n=3). B: bone, HA: HA/TCP.

FIG. 5 shows data demonstrating that subcutaneous transplantation of human BMMSCs rescues bone loss. (A) MicroCT analysis revealed that the third lumbar vertebra in transplant recipient mice (Transplant, lower panels) at 10 months post transplantation showed increase in trabecular bone volume compared to that of age-matched control mice (Control, upper panels). B: vertebral body, Sp: spinosus process of vertebra, asterisk: vertebral foramen. (B) Bone mineral density (BMD) of femurs in recipient mice (n=3) was significantly improved compared to age-matched controls (n=3), as assessed by dual X-ray absorptiometry (DEXA) analysis. Bars showed standard deviation. (C) Bone morphological analysis demonstrated increase in bone volume vs. total volume (BV/TV) and trabecular number (Tb.N), and decrease in trabecular separation (Tb.Sp) in recipient mice (n=3) compared to the controls (n=3). (D) The number of tartrate-resistant acid phosphatase (TRAP)-positive cells (arrows) decreased in the vertebral body of recipient mice (n=3) compared to control mice (n=3). Original magnification: X400. Bars showed standard deviation. (E) Enzyme-linked immunosorbent assay (ELISA) revealed that serum soluble receptor activator NF-κB ligand (sRANKL) and C-terminal telopeptides type I collagen were decreased in recipient mice (n=3) compared to control mice (n=3). However, osteoprotegrin (OPG) was markedly increased in the recipient mice. (F) The number of colony forming unit-fibroblasts (CFU-F) of BMMSCs derived from the recipient mice (Transplant, n=3) increased compared to the age-matched control (n=3). (G) The proliferation of recipient BMMSCs (n=3) was significantly increased as compared to the control group (n=3), as deteunined by BrdU incorporation assay. (II) The population doublings of BMMSCs from recipient mice (n=3) was significantly increased compared to control mice (n=3). (I) Alizarin red staining showed that BMMSCs derived from recipient mice (n=3) had higher calcium accumulation than that from control mice (n=3) under osteogenic conditions.

FIG. 6 shows data demonstrating that subcutaneous human BMMSC transplantation up-regulated Klotho expression in immunocompromised mice. (A) Immunohistochemical staining with anti-Klotho antibody showed that transplant recipient mice (Transplant) expressed higher level of Klotho (arrows) in the epithelial cells, of the renal tubules (RT) than those of age-matched controls (Control). G: glomerulus. Original magnification: X200. Bars showed standard deviation. (B) Western blot analysis confirmed that Klotho was elevated in kidney of transplant recipient (n=3) as compared to non-treated littermates (n=3). (C) Likewise, Western blot analysis showed elevated Klotho in brain of transplant recipient mice (n=3) as compared to the Control, n=3). (D) ELISA further confirms elevated serum Klotho level in transplant recipient mice (n=3) as compared to the control group (n=3). Bars showed standard deviation. (E) Random blood glucose measurement showed decreased serum glucose in recipient mice (n=3) in comparison to control mice (n=3). (F) Similarly, serum insulin growth factor 1 (IGF-I) level was lower in recipient mice (n=3) compared to control mice (n=3). (G) Urine protein level was significantly decreased in recipient mice (n=3) compared to control mice (n=3). (H) Western blot analysis showed that expression of insulin receptor (IR) α, IRβ, phosphatidylinositol 3-kinase (PI3-K) p85, and PI3-K p110 was down-regulated in kidney tissues of transplant recipient mice (n=3) compared to control mice (n=3). β-actin was used as protein loading control.

FIG. 7 shows data demonstrating BMMSC deficiency in MRL/lpr mice. (A-F) MicroQCT analysis of the trabecular bone structure of the distal femoral metaphysis at 20-week-old MRL/lpr mice. MRL/lpr mice (MRL/lpr) exhibited significantly decreased BMD (A). Representative microQCT images of the trabecular bone structure in MRL/lpr mice (n=5) exhibited a significant decrease in bone formation (yellow circle areas, B), bone volume relative to tissue volume (BV/TV, C), trabecular number (Tb.N, D), and bone surface area (BS, E) along with significantly increased trabecular separation (Tb.Sp, F) when compared to the control C3H/HeJ group (Control, n=5; mean±SD; [I]P<0.01). (G) The number of CFU-F (mean±SD) in MRL/lpr mice (n=5) increased significantly as compared to the control group (n=5, [I]P<0.01). (H) BMMSCs derived from MRL/lpr mice (n=5) showed significantly elevated BrdU-uptake rate. (mean±SD; Control, n=5; [III]P<0.001). (I) Representative images of alizarin red staining of BMMSC cultures under the osteogenic conditions. BMMSCs derived from MRL/lpr mice (n=5) showed significantly decreased calcium accumulation (mean±SD; Control, n=5; [III]P<0.001). (J, K) Semi-quantitative RT-PCR (J) and Western blot (K) analysis showed that MRL/lpr-derived BMMSCs presented significant decrease in the expression of runt-related transcription factor 2 (Runx2), alkaline phosphatase (ALP), and osteocalcin (OCN). Glycerinaldehyd-3-phosphat-dehydrogenase (GAPDH) and β-actin were used as loading controls in RT-PCR and Western blot, respectively. Five repeated tests per group showed similar results ($^{III}P<0.001$; $^{I}(P<0.05)$. (L) Representative images of Oil red O staining of BMMSC cultures under the adipogenic conditions. BMMSCs derived from MRL/lpr mice (n=5) showed a significant decreased number of adipocytes (mean±SD; Control, n=5; $^{III}P<0.001$). (M) Semi-quantitative RT-PCR analysis indicated that MRL/lpr-derived BMMSCs had significant decrease in gene expression of peroxisome proliferator-activated receptors gamma 2 (PPARγ2) and lipoprotein lipase (LPL) compared to loading control GAPDH. Five repeated tests per group showed similar results ($^{III}P<0.001$). (N) TRAP staining indicated the increased number of TRAP positive cells (mean±SD) in epiphysis of the distal femurs of MRL/lpr mice (n=5) as compared to the control (Control, n=5; $^{II}P<0.01$). (O, P) ELISA revealed that MRL/lpr mice (n=5) have increased levels (mean±SD) of sRANKL (O, $^{III}P<0.001$) and C-terminal telopeptides of type I collagen (C-telopeptides, P, $^{II}P<0.01$) in serum as compared to the controls (n=5).

FIG. 9 shows data demonstrating that allogenic MSCT reconstructed trabecular bone and osteoblastic niche in MRL/lpr mice. (A) MRL/lpr mice (n=6) showed decreased trabecular bone (TB) formation (yellow circle area, mea.n±SD) when compared to control mice (n=6). MSCT (MSC9, n=6; MSC16, n=6) exhibited a significant increase in the trabecular bone volume. However, CTX treatment failed to recover trabecular bone. [$^{III}P<0.001$ vs. Control; $^{I}P<0.05$ vs. Control; $^{\#\#\#}P<0.001$ vs. MRL/lpr; $^{\$\$}P<0.01$ vs. MSCT (MSC9 and MSC16)]. (B) The number of osteoblasts (open arrows) per bone marrow area (mean±SD) in the distal femoral metaphysis was significantly decreased in MRL/lpr mice (n=6) compared to controls (n=6). MSCT (MSC9, n=6; MSC16, n=6) were able to significantly recover osteoblast numbers in MRL/lpr mice, but CTX treatment (n=6) was not capable of recovering the number. [E$^{II}P<0.01$ vs. Control; $^{III}P<0.001$ vs. Control; #P<0.05 vs. MRL/lpr; $^{\#\#}P<0.01$ vs. MRL/lpr; $^{\$\$\$}P<0.001$ vs. MSCT (MSC9 and MSC16)]. BM: bone marrow. (C-E) In vivo osteogenic assay showed that newly bone (B) and hematopoietic marrow (BM) formation (mean-ESD) were significantly decreased in MRL/lpr-BMMSC transplants (n=6) compared to the control group (n=6). MSCT (MSC9, n=6, and MSC16, n=6), as well as CTX treatment (n=6), can significantly improve BMMSC-mediated newly bone and hematopoietic marrow formation in vivo. CT: connective tissue, HA: HA/TCP. H&E staining. Original magnification; X200. [$^{III}P<0.001$ vs. Control; $^{\#\#\#}P<0.0051$ vs. MRL/lpr; $^{\$\$\$}P<0.001$ vs. MSCT (MSC9 and MSC16)]. (F) The number of CFU-F (mean±SD) in MRL/lpr mice (n=6) increased significantly as compared to control group (n=6). All treatments (MSC9, n=6; MSC16, n=6; CTX, n=6) significantly reduced the number of CFU-F to the control level. ($^{III}P<0.001$ vs. Control, #P<0.05 vs. MRL/lpr, $^{\#\#\#}P<0.001$ vs. MRL/lpr).

FIG. 10 shows data demonstrating that the numbers of forkhead box P3 positive (Foxp3$^+$) cells and interleukin 17 (IL17)-secreting helper T cells (Th17 cells) contributed to pathological process in MRL/lpr mice. (A) Semi-quantitative RT-PCR confirmed decreased forkhead box P3 (Foxp3) gene expression in bone marrow of MRL/lpr mice and increased Foxp3 expression in the treatment groups. The results were representative of five independent experiments ($^{III}P<0.001$ vs. control; $^{II}P<0.01$ vs. control; $^{\#\#\#}P<0.001$ vs. MRL/lpr; #P<0.05 vs. MRL/lpr; $^{\$\$}P<0.01$ vs. MSCT). (B) Immunohistochemical staining with anti-IL17 antibody indicated that number of IL17 positive cells (mean±SD, arrows) was significantly increased in bone marrow (BM) of MRL/lpr mice (n=6). MSCT (MSC9, n=6; MSC16, n=6), as well as CTX treatment (n=6), significantly reduced IL17-positive cells in MRL/lpr bone marrow, but still showed higher level than that in control group ($^{III}P<0.001$ vs. Control, $^{\#\#\#}P<0.001$ vs. MRLapr). (C) Immunohistochemical staining using anti-IL17 antibody showed that number of IL17 positive cells (mean±SD, arrows) was significantly increased in spleen of MRL/lpr (n=6) compare to control group (n=6) and treatment group (MSC9; n=6, MSC16; n=6, CTX; n=6) ($^{III}P<0.001$ vs. Control; $^{\#\#\#}P<0.001$ vs. MRL/lpr). (D) Semi-quantitative RT-PCR revealed high expression of IL17 in bone marrow of MRL/lpr and this increased level of IL17 was decreased in MSCT and CTX treatment groups. The results were representative of five independent experiments ($^{III}P<0.001$ vs. control; $^{\#\#\#}P<0.001$ vs. MRL/lpr). (E) Flow cytometry revealed that MRL/lpr mice had significantly increased level of CD4$^+$IL17$^+$ T lymphocytes in spleen compared to control group. The CD4$^+$IL17$^+$ cells were markedly decreased in MSCT and CTX groups. (F) Semi-quantitative RT-PCR confirmed increased IL17 expression in spleen of MRL/lpr and reduced IL17 expression in the treatment groups. The results were representative of five independent experiments ($^{III}P<0.001$ vs. control; $^{\#\#\#}P<0.001$ vs. MRL/lpr; $^{\$}P<0.05$ vs. MSCT).

FIG. 11 shows data demonstrating that allogenic MSCT reduced number of CD138 positive plasma cells and the capability of autoantibodies and immunoglobulins. (A) ELISA confirmed the decreased levels of IL17 following MSCT (right panel: MSC9, n=5; MSC16, n=5) compared to MRL/lpr mice (n=5). However, CTX treatment (CTX, n=5) failed to show the efficiency. On the other hand, IL6 levels showed no changes, but the levels of total TGFβ were changed similar to that of IL17. rP<0.005 vs. Control (n=5), $^{I}P<0.05$ vs. Control, $^{\#\#\#}P<0.005$ vs. MRL/lpr, $^{\#}P<0.05$ vs. MRL/lpr]. (B) Immunohistochemical staining revealed that MRL/lpr mice (n=6) had increased number of CD138 positive plasma cells (mean±SD, arrows) in bone marrow as compared to control mice (n=6). MSCT (MSC9, n=6; MSC16, n=6) and CTX treatment (n=6) resulted in a significantly decreased number of CD positive plasma cells in the bone marrow. ($^{II}P<0.01$ vs. Control; $^{III}P<0.001$ vs. Control; $^{\#}P<0.05$ vs. MRL/lpr; $^{\#\#\#}P<0.001$ vs. MRL/lpr). (C) ELISA quantified that levels of anti dsDNA IgG antibodies (mean±SD) were significantly increased in spleen of MRL/lpr mice (n=5) when compared to that of controls (n=5), MSCT at 9 weeks (MSC9, n=5) and at 16 weeks (MSC16, n=5) and CTX treatment (CTX, n=5) treatment were able to reduce levels of anti dsDNA IgG, but not significant against CTX group. $^{III}P<0.001$ vs. Control, $^{\#\#\#}P<0.005$ vs. MRL/lpr, $^{\#}P<0.05$ vs. MRL/lpr. (D) ELISA showed MSCT (MSC9, n=5; MSC16, n=5) reduced immunoglobulins (IgG$_1$, IgG$_{2a}$, IgG$_{2b}$ and IgM) levels (mean±SD) in MRL/lpr mice (n=5). CTX treatment (CTX, n=5) also showed efficient effect on IgG$_1$, IgG$_{2a}$, and IgG$_{2b}$, but not for IgM. [$^{III}P<0.005$ vs. Control, $^{II}P<0.01$ vs. Control, $^{I}P<0.05$ vs. Control, $^{\#\#\#}P<0.005$ vs. MRL/lpr, $^{\#\#}P<0.01$ vs. MRL/lpr, $^{\#}P<0.05$ vs. MRL/lpr, $^{\$\$\$}P<0.005$ vs. MSCT (MSC9 and MSC16), $^{\$}P<0.05$ vs. MSCT (MSC9 and MSC16)].

FIG. 12 shows data demonstrating that allogenic MSCT was an effective treatment for treatment-refractory SLE patients. (A) In vivo osteogenic assay revealed that newly bone formation and bone marrow reconstruction were diminished in SLE patients' BMMSC transplants (SLE, n=2) as compared to normal BMMSC transplants (Control, n=2). Arrows indicate osteoblasts lining on the bone surface, B; bone, BM; bone marrow, CT; connective tissue, HA; HA/TCP. H&E staining. Original magnification; X200. (B) Semi-quantitative RT-PCR analysis revealed that SLE patients' BMMSCs showed a decrease in the expression of osteogenic genes Runx2 and OCN as compared to BMMSCs from healthy donor controls. GAPDH was used as a loading control ($^{III}P<0.001$ vs. control). M: months. (C) The scheme of MSCT and CTX treatment in treatment-refractory SLE patients. (D) MSCT led significant decrement of the score of SLEDAI in the recipients at one ($^{I}P<0.05$), six (ERP<0.005), and twelve ($^{II}P<0.01$) months post-transplantation compared to the original indexes prior to MSCT. (E) MSCT showed capable of maintaining reduced urine protein levels in SLE patients at one ($^{I}P<0.05$), two ($^{I}P<0.05$), six ($^{II}P<0.005$) and twelve ($^{III}P<0.005$) months after MSCT compared to the original levels. (F) CD4$^+$Foxp3$^+$ cells in the peripheral blood were significantly elevated in the patients three months post-transplantation (n=4) (EP<0.05) compared to the initial levels (n=4), but not in one-month post-MSCT.

FIG. 13 shows data comparing the characteristics of SHED to BMMSCs.

Figure 2D:
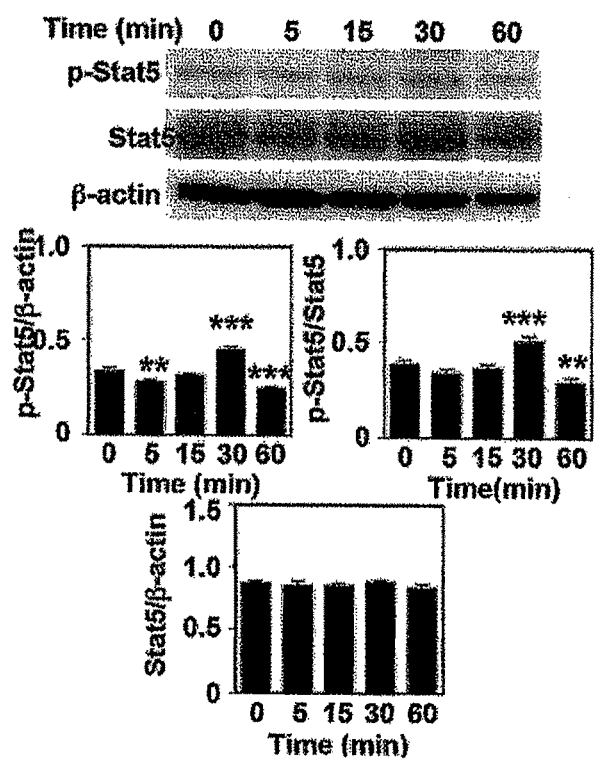
FIG. 2 shows data demonstrating that EPO-R is a progenitor marker of human BMMSCs and mediates bone marrow organization in vivo. (A) Flow cytometric analysis revealed that a small percentage (5.54%) of BMMSCs expressed EPO-R. (B) Reverse transcription polymerase chain reaction (RT-PCR) analysis confirmed EPO-R gene expression in BMMSCs. Jurkat cells were used as a positive control for EPO-R expression. G3PDH: glycerinaldehyd-3-phosphat-dehydrogenase. (C) Western blot analysis further confirmed that BMMSCs express EPO-R at passage 1, 5, and 10 (P1, P5, and P10). (D) recombinant human EPO (rhEPO) treatment (0.1 U/ml) for indicated time (minutes; min) induced a significantly up-regulated expression of phospho-Stat5 in BMMSCs at 30 minutes compared to either β-actin or Stat5 (n=3). However, expression level of Stat5 showed no significantly change (n=3). (E) STRO-1, CD146, and CD166 positive BMMSCs were significantly increased in the rhEPO treatment group (EPO+) as compared to the un-treated group (EPO-) (n=3). (F) rhEPO (0.1 U/ml) treated BMMSCs (EPO+) were capable of inducing active hematopoietic marrow formation (arrows) when transplanted into immunocompromised mice with HA/TCP (HA) as assessed by H&E staining. B: bone. Original magnification: X400. Bars showed standard deviation (EPO+: EPO-: n=3). Semi-quantitative analysis showed that EPO treatment resulted in a significantly increased bone marrow formation in the BMMSC transplants compared to un-treated control BMMSCs. (G) Western blotting analysis confirmed a significant inhibition of EPO-R and signal transducer and activator of transcription 5 (Stat5) expression in BMMSCs transfected with small interfering RNA (siRNA) targeting EPO-R and Stat5, respectively. (H) Loss-of-function of EPO-R and Stat5 resulted in inhibition of bone marrow (arrow) formation in 8-week-old BMMSC transplants as compared to the nonspecific siRNA-transfected transplant (Control). Original magnification: X200; Bars showed standard deviation (Control: EPO-R: n=3, Stat5: n=3; ***: $p<0.005$ vs. Control; #: $p<0.05$ vs. EPO-R; ###: $p<0.005$ vs. EPO-R).

(A) Flow cytometric analysis of cultured SHED at passage 3 revealed expression of STRO-1 (12.06%), CD146 (48.33%), stage specific embryonic antigen 4 (SSEA4) (85.40%), CD73 (91.93%), CD105 (6.77%), CD166 (63.65%), but was negative for surface molecules CD34 and CD45. SHED express high levels of STRO-1 and CD146 (n=5; P<0.05) and low level of CD105 (n=5; P<0.01) compared to expression levels of STRO-1 (8.36%), CD146 (31.19%), and CD105 (13.27%) in BMMSCs. These signals were shown as red area. Solid lines indicated signals for isotype matched control antibodies. MI window showed the positive expression defined as the level of fluorescence greater than 99% of the corresponding isoype-matched control antibodies. Representative histogram were shown among 5 donors. (B) Immunoblot analysis confirmed expression of CD73, CD105 and CD166 in SHED and BMMSCs. Representative images of n=5 donors were presented as results. (C) Immunofluoresence confirmed that SHED express STRO-1, CD146, and SSEA4 along with negative for CD34 and CD45. Red fluorescence indicated the expression of cell surface markers. Blue cell nuclei were stained by 4',6-diamidino-2-phenylindole (DAPI). Images were representative data of independent experiment (n=5) with consistent results (Bar=50 μm). (D) SHED were able to form significantly high number of single colonies than BMMSCs when 1×10$^6$ cells were plated at a low density (*P<0.05) and cultured for 10 days. (E) The proliferation rates of SHED and BMMSCs were assessed by co-culture with BrdU for 18 hours. The number of BrdU-positive cells was presented as a percentage of the total number of cells counted from five replicate cultures. SHED showed a significantly higher proliferation rate in comparison to BMMSCs (P<0.01). (F) SHED showed a high activity of telomerase compared to BMMSCs assessed by real time PCR. HEK293T cells (239T) were used as a positive control and heat inactivated 293T (H.I.) cells were used as a negative control. The activity was indicated by a PCR cycle threshold and averaged from three replicated cultures (*P<0.001).

FIG. 14 shows data demonstrating the mesenchymal stem cell properties of SHED. (A-E) SHED showed a similar osteogenic differentiation potential to BMMSCs, After 1 week culture induction under osteogenic conditions, ALP activity and numbers of ALP positive cells in SHED and BMMSCs were significant higher than that of control SHED and BMMSCs, respectively, by ALP staining (Representative of n=5) (A) and flow cytometric analysis (Representative of n=3) (B). Meanwhile, immunoblot analysis showed that the osteogenic induction elevates expression levels of ALP, Runx2, dentin sialoprotein (DSP), and OCN in SHED and BMMSCs (C) (***P<0.001, n=5). β-actin was used as an internal control. After 4 weeks culture induction in osteogenic medium, SHED showed increased capacity of forming mineralized nodules as assessed by alizarin red staining (Representative of n=5) (D). Alizarin red-positive area corresponding to total area was averaged from five independent groups (E). (F-H) SHED showed reduced potential of differentiating into adipocytes compared to BMMSCs. Three weeks post adipogenic induction, lipid accumulation in SHED was less than that in BMMSCs by oil-red O staining (Representative of n=5) (F). Number of oil-red O-positive (Oil-Red-O+) cells was calculated as a percentage to total cells and averaged from five independent cultures (G) (*P<0.05). Immunoblot assay indicated that SHED expressed lower levels of adipocyte-specific molecules LPL and PPARγ than BMMSCs at 3 weeks post adipogenic culture (H). Three independent assays showed the similar results. (I-K) SHED were capable of forming mineralized tissue when transplanted subcutaneously into immunocompromised mice using HA/TCP as carrier (Representative of n=3) (I). It appeared that SHED form similar amount of mineralized tissue as seen in BMMSC transplant (Representative of n=3) (I, J), but they generated significantly less bone marrow elements than BMMSCs (K). Newly formed mineralized tissue and bone marrow area was calculated as a percentage of total area and averaged from three independent transplant assays (***P<0.001). B: bone, BM: bone marrow, CT: connective tissue, HA: hydroxyapatite and tricalcium carrier. (L-P) SHED and BMMSCs express multiple signaling pathways during culture expansion at passage 3. SHED and BMMSCs expressed transforming growth factor beta (TGFβ) receptor I and II, Smad 2 and phosphorylated Smad 2 (L); P38, phosphorylated P38, extracellular signal-regulated kinases (ERK), and phosphorylated ERK (M); Akt and phosphorylated Akt (N); N-cadherin and β-catenin (O); platelet-derived growth factor (PDGF) receptor and Ang-1 (P). Representative image of n=5.

FIG. 15 shows data illustrating the interplay between SHED interplay and T-lymphocytes. (A, B) Under the anti-CD3 and CD28 antibody along with TGFβ1 and IL-2 stimulation, SHED showed a significant effect in reducing Th17 cell levels as seen in BMMSCs (A), however, SHED exhibited a significant capacity of inhibiting IL17 levels than BMMSCs (B) (n=3, P<0.05,P<0.001). (C) Peripheral blood mononuclear cells (PBMNCs) activated by anti-CD3 antibody (@CD3Ab, 1 μg/ml) were capable of inducing significant SHED and BMMSC death (black arrow) as shown by toulidin blue staining. When culture in an indirect co-culture system using Transwell, activated slenocytes failed to induce SHED and BMMSC death. Neutralization with anti-Fas ligad (FasL) antibody (@FasLAb, 1 μg/ml) blocked PBMNC-induced SHED and BMMSC death. Representative of n=3. (D) SHED express higher level of Fas in compared to that in BMMSCs by immunoblotting. Three independent experiments showed similar results. Representative of n=3. (E) SHED death caused by active PBMNCs is through an apoptotic pathway according to the terminal deoxynucleotidyl transferase dUTP nick end labeling (TUNEL) staining. The SHED death rate was similar to BMMSCs. The percentage of TUNEL-positive (TUNEL+) nuclei was indicated to the total number of MSCs and averaged from 5 replicated cultures (*P<0.005).

FIG. 16 shows data demonstrating that SHED transplantation reduced levels of autoantibodies and improved renal function in MRL/lpr mice. (A) The scheme of SHED and BMMSC transplantation procedures. (B-D) ELISA quantified that levels of anti dsDNA IgG (B), IgM (C) and nuclear (D) antibodies (ANA) (mean±SD) were significantly reduced in the peripheral blood of SHED and BMMSC treated MRL/lpr mice (n=6) when compared to untreated MRL/lpr mice c (n=6) (***P<0.001). It appeared that SHED transplantation resulted in a more significant reduction in anti IgG when compared to BMMSC transplantation (B). (E) MRL/lpr mice showed renal disorders such as nephritis with glomerular basal membrane disorder and mesangium cell over-growth. SHED and BMSSC transplantation resulted in a reduced basal membrane disorder and mesangium cell over-growth in glomerular (G) (upper panels, H&E staining; middle panels, trichrome staining; lower panels, periodic acid-schiff staining). Representative images of untreated, SHED and BMMSC MRL/lpr (n=6). (F) ELISA analysis showed that SHED transplantation has the same effect as seen in BMMSC transplantation in significantly reducing C3 level in urine and elevating C3 level in serum (n=6, *P<0.05, **P<0.01). (G) SHED transplantation significantly reduced urine protein levels (mean±SD) compared to BMMSC transplanted MRL/lpr mice (n=6). (EEEP<0.001). (H) Markedly increased urine creatinine and reduced serum creatinine were observed in SHED and BMMSC transplanted MRL/lpr mice (n=6) compared to un-treated MRL/lpr mice (n=6, [[[P<0.001, [[P<0.01).

FIG. 17 shows data demonstrating that the ratio of regulatory T cells (Tregs) and Th17 cells may contributes to SHED mediated treatment in MRL/lpr mice. (A-C) Flow cytometric analysis showed that the number of CD25+ Foxp3+ Tregs in CD4+ T lymphocytes of MRL/lpr spleen was not significantly changes in SHED and BMMSC transplantation (A). In contrast, SHED and BMMSC transplantation were capable of significantly reduced levels of CD4+ IL17+ cells in spleen as compared to un-treated MRL/lpr mice (B). SHED transplantation significantly increased the ratio of Tregs and Th17 cells when compared to BMMSC transplantation group (C) ([[[P<0.001, [[P<0.01, [P<0.05). Results were shown as means±SD from un-treated, SHED and BMMSC MRL/lpr (n=6). (D-F) Although SHED and BMMSC transplantations failed to alter IL10 (D) and IL6 (E) levels in serum of MRL/lpr mice, IL17 levels were significantly down-regulated in SHED and BMMSC transplanted group compared to un-treated MRL/lpr mice (F). Results were shown as means±SD from un-treated, SHED and BMMSC MRL/lpr (n=6).

FIG. 18 shows data demonstrating that SHED transplantation reconstructed trabecular bone and inhibited osteoclast activity. (A) SHED transplantation showed same effect in regenerating trabecular bone as seen in BMMSC transplanted MRL/lpr mice (n=6) ([[P<0.01). (13) TRAP staining showed that the number of TRAP positive osteoclasts was significantly reduced in SHED and BMMSC transplanted mice (n=6, [P<0.05). (C, D) ELISA revealed that SHED and BMMSC transplantations were capable of significantly reducing the levels (meandSD) of soluble RANKL (sRANKL) (C) and C-terminal telopeptides of type I collagen (CTX) (D) in serum of MRL/lpr mice (n=6) (*P<0.05, **P<0.01).

DETAILED DESCRIPTION

Having summarized the various aspects of the invention, a detailed explanation and description of the invention will now be provided with reference to the following specific embodiments, experiments, and illustrations.

Although the present invention are described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims Life Extending Properties Related to Subcutaneous Transplantation of Mesenchymal Stem Cells and Establishment of a Novel Animal Model for Aging-Related Degenerations Previous studies have identified that ectopically generated bone/marrow structures contain functional HSCs capable of rescuing impaired hematopoietic function in irradiated mice. Here the inventors demonstrate that subcutaneous transplantation of hydroxyapatite tricalcium phosphate (HAITCP) with human BMMSCs, but not fibroblasts, can restore active hematopoiesis in immunocompromised mice. These evidences show that hematopoiesis, a fully active process which occurs in all marrow throughout the skeleton during early development, can be re-initiated at the ectopic site, and presumably other bones, in this case the femurs and vertebrae, with increase in both myeloid and lymphoid components in adult immunocompromised mice.

The inventors also found that EPO-R is an early marker of BMMSCs and that EPO-R/Stat5 pathway is essential in the regulation of ectopic bone marrow formation in BMMSC transplants. Very recent studies also suggested that EPO enhanced BMMSC-mediated cardiac tissue regeneration in a murine model of myocardial infarction, which corroborated the inventors' findings.

More importantly, the inventors uncovered a potential clinical application in delaying the aging process for the innate physiological process of bone marrow mediated stem cell renewal and differentiation. As will be illustrated in the experiments below, subcutaneous transplantation of BMMSC using a carrier provides a long-term engraftment of BMMSCs at the ectopic site at least 18 months. These BMMSCs can be transferred to new hosts by secondary transplantation. The establishment of the functional ectopic hematopoietic organ is unique to subcutaneous transplantation, not standard BMMSC infusion approach. This result suggests a link between the presence of an organized BMMSC-hematopoietic organ, hematopoietic regeneration, and lifespan extension in mice. Stem cell homing to the primary BMMSC transplants, and subsequently engrafting in secondary transplants are reflected in the low percentile of eGFP positive HSCs. While not intending to be bound by any particular theory, the inventors theorize that the anti-aging effect was likely attributed to the newly developed or reconstituted bone marrow organizing systems in recipients with capabilities to restore systemic immune functions, enhance tissue regeneration, and reverse aging-related degenerative changes at both cellular and organ levels.

The process of active generation of new hematopoietic marrow components which mimics marrow-genesis observed in the early bone developmental stage, seen here at the ectopic subcutaneous hematopoietic organ in BMMSC/HA/TCP transplant mice, as well as other skeletal bones, appears to slow down as the animal ages and is an important aging-related degenerative phenotype with a broad systemic effect, and therefore understandably affects the longevity of the transplant recipient. Although it has been suggested that regulating immune function is a potential approach in the manipulation of lifespan in lower organism model, up-to date, there is no such study in the vertebrate species. The establishment of the animal model of this invention (e.g. subcutaneous transplantation of BMMSC in immunocompromised mice) provides a novel research tool to unfold the effect of BMMSC-mediated hematopoiesis restoration on lifespan enhancement and delayed degenerative changes in aging mice.

For example, using the animal model of this invention, the inventors demonstrated that BMMSC transplant resulted in elevated Klotho expression and suppression of insulin-like growth factor I signaling in recipient mice. Since BMMSCs do not express Klotho in the system, the inventors reasoned that BMMSC-mediated hematopoiesis may be partly link to Klotho expression. Recently, the over-expression of Klotho, a circulating hormone that inhibits intracellular insulin and IGF-I signaling, has been implied in lifespan extension in mice. Although it is known that regulating immune function may manipulate lifespan, it is unknown how BMMSC transplant resulted in elevated expression of Klotho. Until now, the identification of longevity associated genes appears to involve the insulin receptor/IGF-I receptor pathway, by regulating cellular stress and caloric restriction in mice. In contrast, reduced IGF-I activity in humans is not associated with longevity. In humans, low IGF-I activity has been associated with an increased risk of developing cardiovascular disease and diabetes. In contrast, high IGF-I activity in human is associated with an increased risk of developing cancer of the breast, prostate, lung and colon. These findings suggest that multiple pathways contribute to the anti-aging effects and the prolongation of life in complex organisms.

Extending lifespan by BMMSC-organized hematopoietic marrow elements is physiologically complex and uniquely distinct from previously reported lifespan alteration caused by single gene or signaling pathway. The approach, based on BMMSC-mediated reconstitution of the hematopoietic system resembling developmental marrow-genesis, allows further investigation in the broader systemic effects on multiple bone marrow related cellular and organ systems without the need for genetic manipulation.

Accordingly, based on the discoveries described herein, this invention provides an animal model useful as a research tool for studying aging-related degeneration. Animal models of this invention may be created by subcutaneously transplanting a plurality of mesenchymal stem cells to a test animal. The test animal is preferably a mammal, more preferably, a rodent. The test animal is also preferably immunocomprised. In one embodiment, the test animal is a beige nude XidIII (nu/nu) mutant mouse.

The mesenchymal stem cells can be allogenic or autologous. They can also be obtained from a variety of sources, including, BMMSCs, SHED, but are not limited thereto.

The mesenchymal stem cells are preferably delivered on a substrate (also referred to herein as a carrier) suitable for bone grafting. Exemplary substrate may include HA/TCP or any other suitable substrates known in the art such as bioactive glass and/or calcium carbonate. In a preferred embodiment, the substrate is RA/TCP.

It is noted that previous attempts using allogenic BMMSCs to generate ectopic bone/marrow structure in regular mice were not successful due to the strong immune response in the subcutaneous area. Currently, isolation of autologous BMMSCs from mice remains a challenged task, partly due to lethality secondary to the small body size of the animal. Therefore, the following exemplary experiment utilized beige Nude XidIII (nu/nu) mutant mice, the immunocompromised strain caused by a triple constitutive gene mutation (see Harlan Laboratories' website at URL: www.harlan.com/models/beigenude.asp), in which BMMSCs can be transplanted to generate ectopic bone and hematopoietic marrow. This animal model represents an advancement in in vivo system than the most widely used in vivo models such as Caenorhabditis elegans and provides a testable paradigm for alleviating common age-related degenerations in several organ systems and enhancing survival in adult immunocompromised mice.

Insofar as implantation of mesenchymal stem cells have been demonstrated herein to show reproducible results in ameliorating and reversing aging-related degenerations, this invention also provides methods that utilize this finding to extend the lifespan, improve the quality of life of a subject. As used herein, quality of life refers to the physical health state of the subject. For healthy subjects, methods of this invention resists the aging process and allows the subject's body to maintain in a more youthful state of health for an longer time span than otherwise possible.

For subject who already suffers aging-related degeneration in one or more organs, this invention also provides methods for ameliorating and reversing such aging-related degenerations.

The above methods may be implemented with various practical differences depending on the environment, conditions, and other relevant factors, but they all share the same common step of transplanting subcutaneously a plurality of mesenchymal stem cells to the subject.

The mesenchymal stem cells may be derived from a variety of sources, including autologous BMMSCs, autologous SHED, allogenic BMMSCs, allogenic SHED, or a combination thereof, but not limited thereto. The key defining factor of a mesenchymal stem that is suitable for use with methods of the invention is that it is capable of generating a functional bone or marrow element. As used herein, a functional bone or marrow element refers to organized hematopoietic stem/progenitor cells and their lineage cells surrounded by mineralized tissue.

The mesenchymal stem cells may be delivered via a variety of carriers, but preferably on a substrate suitable for bone grafting as described above. In a preferred embodiment, the carrier is HA/TCP.

In some embodiments, the transplanted mesenchymal stem cells may be further stimulated or activated by EPO. Thus, in these embodiments, there will be an additional step of administering a predetermined dosage of EPO to the subject after the transplanting step.

Determination of a suitable dosage will include considerations such as the subject's physical make up, state of health, desired effects, etc., and is within the skill of the art.

Applications of Allogenic BMMSCs and SHED in Treating SLE-Like Autoimmune Diseases In addition to the aging-related properties, the inventors have also discovered that allogenic mesenchymal stem cells exhibit unexpected immune-modulation properties in SLE-like autoimmune diseases.

SLE is a common and potentially fatal autoimmune disease characterized by antibodies associated multi-organ injuries including renal, cardiovascular, neural, musculoskeletal, and cutaneous systems. The pathology of SLE involves the destruction of targeted organ tissues and accumulation of auto-reactive lymphocytes and immune complexes. Although disease severity and organ involvement vary significantly among SLE patients, abnormalities of T and B lymphocytes are universal. Moreover, SLE manifests multifaceted immune modulation, including both deficiency and hyperactivity of the immune system. Other autoimmune disease that show similar pathology as SLE include rheumatoid ahthritis, systemic screlosis, dermatomyositis complex, polymyositis, and/or polyarteritis nodosa, but not limited thereto. These diseases are referred to herein as SLE-like autoimmune diseases.

Despite advances in immunosuppressive medical therapies, SLE remains potentially fatal in some patients, especially in treatment-refractory patients. As will be demonstrated below, the inventors have discovered that impairment of BMMSCs and their associated osteoblastic niche deficiency contribute in part to the pathogenesis of SLE-like disease in MRL/lpr mice. Based on this discovery, the inventors have also shown that allogenic BMMSC transplantation (MSCT) is capable of reconstructing the bone marrow osteoblastic niche and more effectively reverses multi-organ dysfunction as compared to medical immunosuppression with cyclophosphamide (CTX). At the cellular level, MSCT, not CTX treatment, was capable to induce osteoblastic niche reconstruction, possibly contributing to the recovery of regulatory T cells and re-establishment of the immune homeostasis. Based on the premising clinical outcomes in SLE mice, 4 CTX/glucocorticoid treatment-refractory SLE patients were treated using allogenic MSCT and showed a stable 12-18 months disease remission in all treated patients. The patients benefited an amelioration of disease activity, improvement in serologic markers and renal function.

Accordingly, this invention also provides methods for treating SLE-like autoimmune diseases which generally includes the step of administering to a patient in need of the treatment a composition comprising a plurality of allogenic mesenchymal stem cells. The allogenic stem cells may be derived from a variety of sources, including but not limited to BMMSC, SHED, or a combination thereof.

The stem cells are preferably provided as a non-attached suspension, but may also be provided as particle-attached or a combination thereof.

Exemplary SLE-like autoimmune diseases may include systemic sclerosis and rheumatoid arthritis. In a preferred embodiment, the SLE-like autoimmune disease is CTX/glucocorticoid treatment-refractory SLE.

The composition may be administered to the subject via intravenous injection, intraperitoneal injection, intramuscular injection, or a combination thereof.

Experiment 1

1.1 Ectopic BMMSC Transplant Extends Lifespan in Immunocompromised Mice

In this study, the inventors revealed that transplantation of BMMSCs with HA/TCP as a carrier subcutaneously into 6 month-old immunocompromised mice significantly extends lifespan, as compared to age-matched control mice (FIG. 1A).

The inventors analyzed survival using the Mantel-Haenszel test and found significantly greater overall survival of transplant recipient mice when compared to their littermates. The mean time to death was 355.7±74.5 days in 50% of control mice and 461.0±137.8 days in 50% of transplant recipients. The longevity of the recipient mice transplanted with BMMSC was significantly improved with an average extension of lifespan by 33.4% ($p<0.01$). Notably, the inventors observed an alleviation of a common natural aging process, shown here in 6 out of 9 control mice at 16 months of age, as a reduction in the vertebral curvature of the backs and the tails (FIG. 1B). These aging phenotypes were absent in all survived BMMSC transplanted mice (FIG. 1B).

Since caloric restriction is known to be associated with increased longevity, the inventors monitored food intake and oxygen consumption in both groups (data not shown). No significant differences in body weight between BMMSC transplanted and control mice were observed (FIG. 1C), indicating that the lifespan extension may be independent of food intake and weight.

To confirm the specific effect of transplantation of BMMSC/HA/TCP in lifespan extension in immunocompromised mice, the inventors transplanted HA/TCP particle both with and without skin fibroblasts. These carrier-only, and fibroblast-carrier transplanted mice showed no significant differences in lifespan as compared to control immunocompromised mice (FIG. 1D). HA/TCP carrier with and without fibroblast transplants showed absence of ectopic bone/marrow organization as compared to BMMSC/HA/TCP transplants (FIG. 1E), thus, confirming that the ectopic bone/marrow organization was not due to the implantation of BMMSC.

To further confirm that the effect on lifespan extension was associated with an organized BMMSC-hematopoietic organ, the inventors treated mice with the intravenous infusion of BMMSCs. The BMMSC infused mice failed to generate an organized hematopoietic organ and did not benefit a significant increase in survival seen in the subcutaneous BMMSC/HA/TCP transplant group (FIG. IF). These findings indicate that subcutaneous transplantation of BMMSC/HA/TCP is capable of establishing an organized hematopoietic marrow organ that may contribute to the physiological process leading to lifespan extension in immunocompromised mice.

1.2 EPO-R/Stat5 Axis Regulates BMMSC-Organized Ectopic Hematopoietic Marrow Formation Since the generation of an organized bone/hematopoietic marrow organ appears to be essential in the survival benefits conferred by BMMSC/HA/TCP transplantation, the inventors endeavored to uncover the mechanisms underlying BMMSC-mediated recipient hematopoietic marrow formation.

In this endeavor, the inventors unexpectedly discovered that 5.45% of the culture expanded BMMSCs expressed EPO-R by flow cytometric analysis (FIG. 2A). The EPO-R positive BMMSCs may represent a small subset of the heterogenous population of BMMSC. This is in agreement with previous reports that heterogeneity is an inherent feature of mesenchymal stem cells. BMMSCs expression of EPO-R was subsequently confirmed by reverse transcription polymerase chain reaction (RT-PCR) and Western blot analysis (FIGS. 2B, 2C).

Figure 2E:
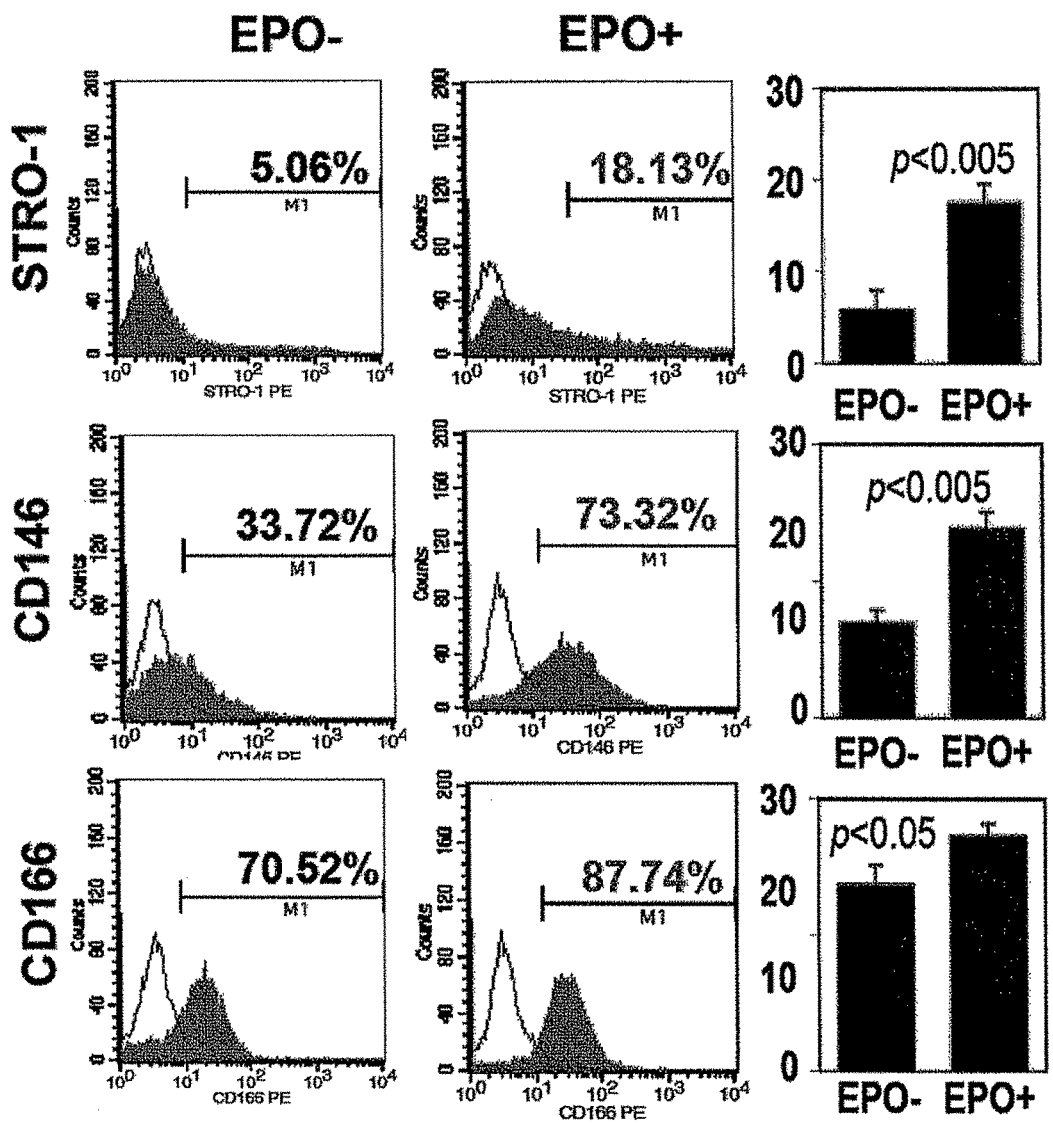

When treated with EPO, BMMSCs showed a significant activation of Stat5 phosphorylation at 30 minutes induction, representing a conservation of the traditional EPO/EPO-R/Stat5 pathway in BMMSCs (FIG. 2C). However, expression of Stat5 in BMMSCs was not altered by EPO (FIG. 2D). Treatment with EPO led to the up-regulated expression of mesenchymal stem cell markers STRO-1, CD146, and CD166 (FIG. 2E), suggesting a possible role of EPO-R in the regulation of stem cell markers in BMMSCs.

Figure 2H:
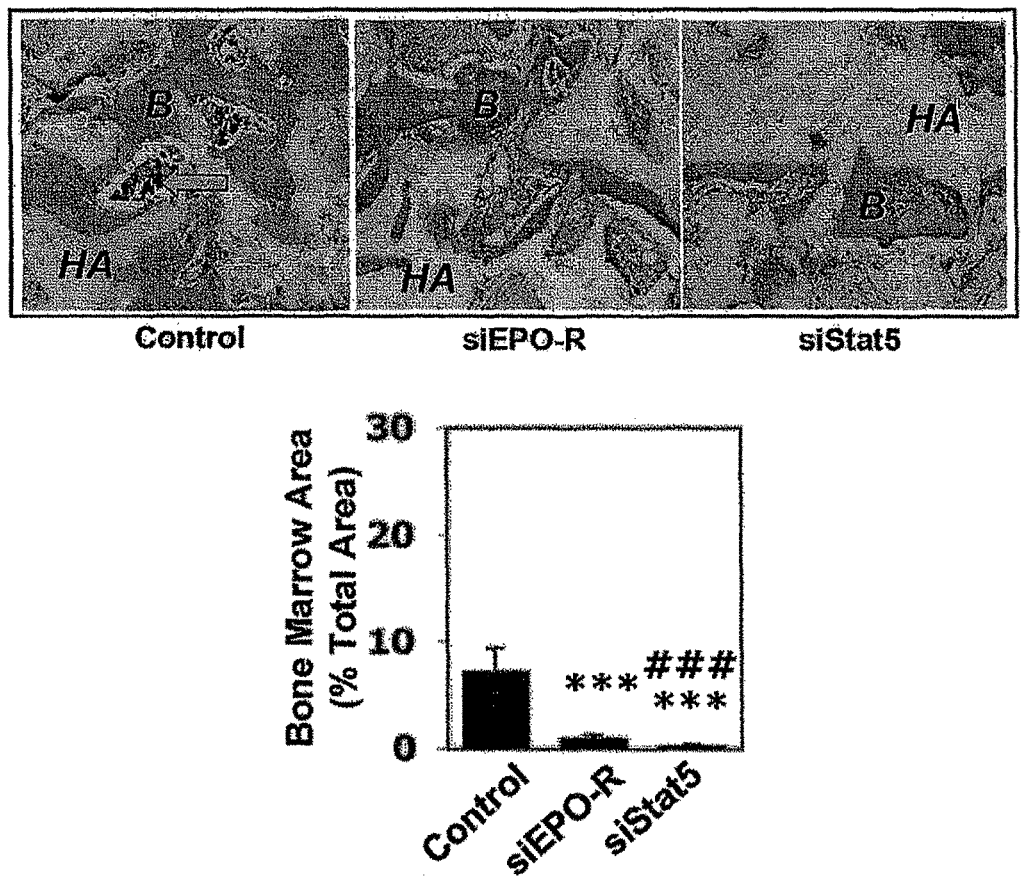

More importantly, using the in vivo transplantation approach, the inventors found that EPO-treated BMMSCs showed a 2- to 3-fold increased capacity of organizing recipient bone marrow elements (FIG. 2F). When EPO-R or signal transducer and activator of transcription 5 (Stat5) were knocked-down using small interfering RNA (siRNA) approach (FIG. 2G), the capacity of organizing hematopoietic bone marrow was significantly decreased, approximately 8- and 25-fold reduction in the percentage of bone marrow area, respectively (FIG. 2H). Given that the EPO and EPO-R system is known to have diverse biological functions in hematopoietic and non-hematopoietic systems, the data provided further supporting evidences that EPO receptor is an early marker of BMMSCs and the EPO/EPO-R/Stat5 signaling pathway contributes in part to mechanisms underlying transplanted BMMSC-organizing hematopoiesis.

1.3 Reconstitution of Active Hematopoiesis in Immunocompromised Mice

Inspired by the observation that subcutaneous transplantation of human skin fibroblasts using HA/TCP as a carrier failed to extend lifespan in immunocompromised mice, the inventors hypothesized that BMMSC-mediated ectopic bone/marrow organization can restore active hematopoiesis and alleviate age-related degeneration in recipient mice.

First, ex vivo expanded BMMSCs were transplanted into the dorsal surface of immunocompromised mice. At eight weeks post transplantation, bone/marrow organ-like structures were generated (FIG. 3A). Newly formed bone/hematopoietic marrow components persisted as long as 18 months as assessed by H&E staining (FIG. 3B) and presence of long term retaining (14 weeks) bromodeoxyuridine (BrdU) positive cells in the marrow compartment (FIG. 3C), indicating that the transplanted BMMSC-organized bone/marrow system is capable to persist throughout the whole course of the post-transplantation period and may contribute, to some extent, to the immediate niche of stem/progenitor cell populations.

Figure 3E:
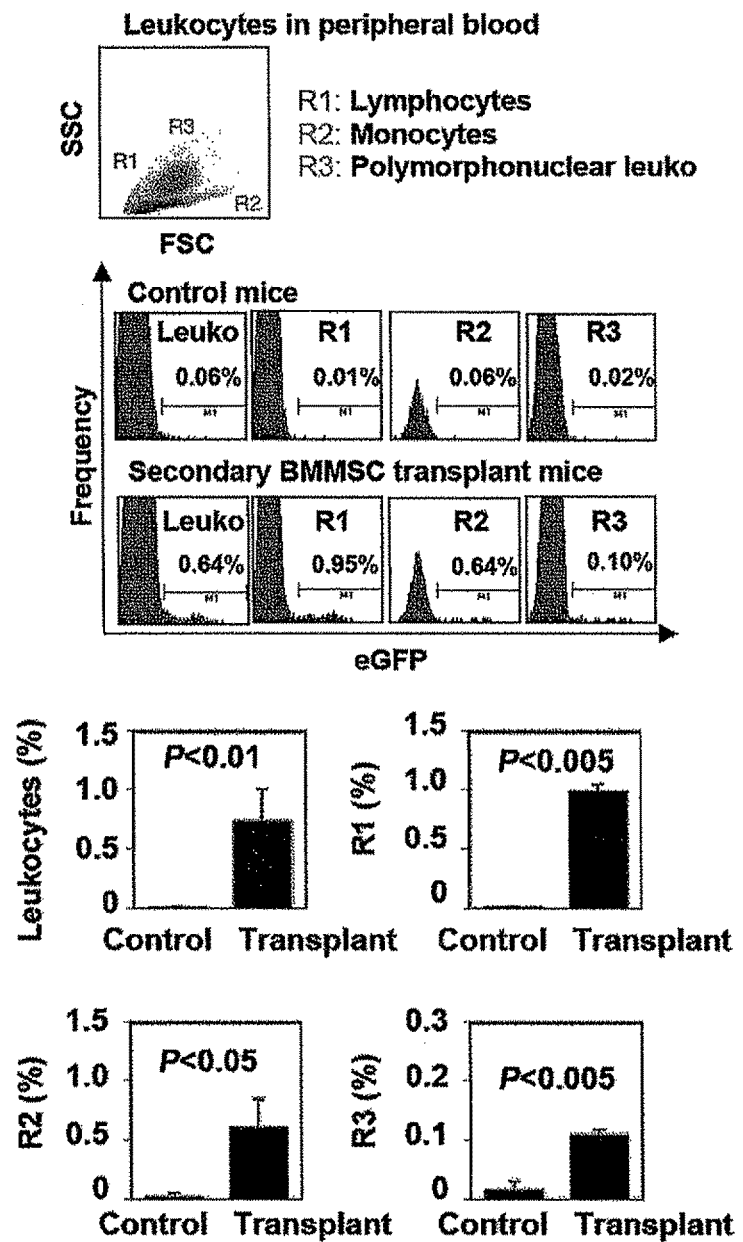
FIG. 3 shows data demonstrating that subcutaneous transplantation of human BMMSCs reconstitutes active hematopoiesis in adult immunocompromised mice. (A) MicroCT analysis revealed that bone (B) and bone marrow elements (BM) regenerated in eight-week BMMSC transplants. Original magnification: X200. (B, C) Long-term (12 months) engraftment of BMMSC-mediated bone/marrow formation in subcutaneous transplants showing organized bone and bone marrow components by H&E staining (B) and BrdU label retaining assay showing bromodeoxyuridine (5-bromo-2-deoxyuridine (BrdU)-positive cells (arrows) in the bone marrow compartment for 14 weeks post-labeling (C). Original magnification: X200. (D) A scheme of enhanced green fluorescent protein (eGFP) positive mouse bone marrow cells (BM cells) homed to the BMMSC-generated bone/marrow organs. BMMSCs were transplanted subcutaneously into immunocompromised mice (top panel). Eight weeks post-transplantation, eGFP positive BM cells were injected through the tail vein of the primary transplant recipient (second top panel). The eGFP positive BM cells homed to the bone marrow niche in the primary BMMSC transplants (third top panel). Four weeks later the primary BMMSC transplants were removed as donor transplants for secondary transplantation (fourth top panel). Four weeks post-secondary transplantation, peripheral blood was collected for flow cytometric analysis (bottom panel). (E) The secondary transplants were capable of supplying hematopoietic cells in the circulation of the recipients (n=3) at 4-week post transplantation. Flow cytometric analysis revealed existence of eGFP lymphocytes, monocytes and polymorphonuclear leukocytes in peripheral blood leukocytes (PBLs). PBLs of the non-transplanted mice were used as negative controls. An average of 3 mice per group was used in the analysis of each cell subset. Comparative analysis of each cell subset was determined and statistically analyzed (Control: n=3, Transplant: n=3; leukocyte %: p<0.01; R1: p<0.005; R2: p<0.05; R3: p<0.005). Data is representative of 3 independent experiments.

To further examine the homing and long-term engraftment of BMMSC transplantation in the system, whole bone marrow cells derived from enhanced green fluorescent protein (eGFP) transgenic mice were administered through the tail vein of primary recipient mice at eight weeks post subcutaneous BMMSC transplantation (FIG. 3D). The primary BMMSC transplants generated in immunocompromised recipients, capable of homing eGFP bone marrow cells, were re-implanted into the dorsal surface of secondary immunocompromised recipient mice (FIG. 3D). Four weeks later, leukocytes in the peripheral blood of the secondary recipient mice were analyzed. Flow cytometric analysis revealed a 75-fold increase in eGFP positive leukocytes (0.64%) in the peripheral blood consisting of both lymphoid (R1, 0.95%) and myeloid cells (monocytes, R2, 0.64% in eGFP-positive leukocytes; polymorphonuclear cells, R3, 0.10% in eGFP-positive leukocytes) in secondary transplant as compared to control mice (FIG. 3E). The marked systemic leukocytic elevation was consistent with similar increase in both lymphoid and myeloid components (FIG. 3E). These results demonstrate that transplanted BMMSCs could yield long-term engrafting mesenchymal stem cells with capability to organize marrow elements, reconstitute active hematopoiesis and mobilize functional hematopoietic components in the recipients.

To determine whether active hematopoiesis occurs in other bones where the activity presumably slows down after the growth spurt period, the inventors examined the femurs and vertebrae in three mice from each group at age 16 months. In 12 out of 15 sections of three BMMSC transplant recipients, the inventors found that the femur showed distinct red and cellular marrow compartment in transplant recipient mice versus the expected yellow and fatty marrow in the normal aging control mice (FIG. 4A). The red marrow component is enriched in CD45 positive hematopoietic cells (2-3 fold increase), B220 positive B cells (6-7 folds), and TER119 positive erythroid cells (~2 folds) (FIG. 4B). Moreover, the inventors found that BMMSCs derived from the primary transplant recipient mice showed an elevated bone (~2 folds) and bone marrow formation (7-8 folds) when subcutaneously transplanted into secondary recipient immunocompromised mice (FIG. 4C). Bone marrow section of the secondary recipient mouse showed an increase in CD45 positive hematopoietic cells (4-5 folds), B220 positive B cells (3-4 folds), and TER119 positive erythroid cells (5-6 folds) as compared to those in controls (FIG. 4D).

These data suggest that BMMSCs are capable of re-organizing functional hematopoietic marrow elements and reconstituting active medullary hematopoiesis at the transplant site, and possibly, other bones, in this case the femur.

Taken together, the reestablishment of active hematopoiesis in adult mice, an early developmental process that slows down or diminishes in the aging process, reveals a practical approach of utilizing BMMSC-mediated reconstitution of active hematopoiesis to boost the immune system or rescue the inherent immunological impairment in immunocompromised mice.

1.4 Alleviating Aging-Like Phenotypes in Multiple Organ Systems

Given that BMMSC-mediated hematopoietic marrow formation participates in the immune system, the inventors hypothesized that subcutaneous BMMSC transplantation may contribute to lifespan extension by retarding the age-related degenerative processes in multiple organs in transplant recipients. The inventors first examine the bone/marrow system using histological and functional analyses. Increased trabecular bone volume (~2 folds) and bone mineral density (BMD) were observed in both vertebrae and femurs of three transplant recipient mice as assessed by μCT and dual X-ray absorptiometry (DEXA) analysis, respectively (FIG. 5A-C). Additionally, the inventors observed an overall suppression of osteoclastic activity in the vertebra of the transplant mice evidenced by a decreased tartrate-resistant acid phosphatase (TRAP) positive osteoclasts (~0.5 fold) (FIG. 5D), reduced levels of soluble receptor activator of nuclear factor κB ligand (sRANKL) (~0.5 fold) and C-terminal telopeptides of type I collagen (~0.5 fold) in peripheral blood, and increased level of osteoprotegrin (OPG) (~2 folds) as compared to the control litteunates (FIG. 5E). These data suggest that BMMSC transplantation may slow down aging-related osteoporosis process by enhancing osteogenesis and suppressing osteoclast activity.

Next, the inventors examined whether BMMSC transplantation affected mesenchymal stem cell functions of the recipients. By examining the colony forming unit-fibroblasts (CFU-F) efficiency of BMMSCs from three recipients, an assay representing the number of clonogenic mesenchymal progenitors, the inventors found a significantly increased number of CFU-F in three recipient mice compared to the un-treated control mice (4 folds) (FIG. 5F). In addition, the proliferation and population doublings of BMMSCs from the recipient mice was also dramatically increased compared to the control group, as assessed by BrdU incorporation (~1.5 fold) and ex vivo proliferation analysis (~2 folds) (FIGS. 5G and 5H). Moreover, the inventors showed that subcutaneous BMMSC transplantation led to advanced osteogenic differentiation of the recipient BMMSCs, as shown by increased mineralization in osteogenic inductive cultures (~2 folds) (FIG. 5I).

Taken together, these data demonstrated that subcutaneous transplantation of BMMSC could enhance stem cell functions in the recipients.

The data demonstrated that subcutaneous BMMSC transplantation effected a delay in aging-related degenerative changes in multiple organ systems of the recipients as compared to their age-matched control mice.

1.5 Upregulation of Klotho in BMMSC Transplanted Mice

In order to determine the mechanism that may contribute to the lifespan extension by BMMSC transplantation, the inventors examined expression level of Klotho, a circulating hormone capable of extending the lifespan of mice via regulation of IGF-I signaling pathway (18). In the study, the inventors found that Klotho was significantly up-regulated (~2 folds) in multiple organs of three BMMSCtransplanted mice, including epithelial cells lining the renal tubules (FIG. 6A), kidney and brain tissues (FIG. 6B, 6C), and peripheral blood (~1.5 folds) (FIG. 6D). Systemically, three recipient mice that received BMMSC transplantation manifested significantly decreased serum glucose (~0.5 fold) and IGF-I levels (~0.5 fold) as well as a decreased urine protein level (~0.5 fold) when compared to control littermates (FIG. 6E, 6F, 6G). Moreover, the inventors found that several IGF-I signaling associated molecules including insulin receptors α and β and phosphatidylinositol 3-kinase (PI3-K) subunits p85 and p110 were down-regulated in kidney tissues of these recipient mice (FIG. 6H).

These results demonstrated that subcutaneous BMMSC transplantation is capable of up-regulating Klotho expression. While not intending to be bound by any particular theory, the inventors theorize that these effects may contribute, at least in part, to the underlying altered anti-aging physiology for the extended lifespan in the treated mice.

Materials and Methods

Mice.

Littermate female Beige Nude XidIII (nu/nu) immunocompromised mice (8-12 week-old), and eGFP transgenic mice (female, 6-7 week-old) were purchased from Harlan. C3H/HeJ mice (female, 6-7 week-old) were from Jackson Laboratories. Animal experiments were performed under the research protocol approved by the Institutional Animal Care and Use Committee (University of Southern California, protocol #10874). All animals were maintained in a temperature-controlled room with a 12-h alternating light-dark cycle and fed sufficient diet and water, ad libitum throughout the experimental period.

Antibodies.

Antiserum against STRO-1 was treated as reported previously (Shi et al., Nat Biotechnal. 2002 20(6):587-591). Mouse monoclonal antibodies anti mouse mitochondria and ATPase were purchased from Abeam Inc. and Chemicon International, respectively. Rabbit polyclonal antibodies for anti human erythropoietin (EPO) receptor, and phosphatidylinositol 3 kinase subunit p85 or p110 were purchased from Santa Cruz Biotechnology. Rabbit polyclonal and rat monoclonal antibodies for anti mouse Klotho were purchased from Alpha Diagnostic Inc. and R&D Systems, respectively. Rabbit anti-human Stat5 and phospho-Stat5 antibodies were from Cell Signaling Technology. R-Phycoerythrin (PE)-conjugated mouse anti-human CD146 and CD166, PE-conjugated and purified rat anti-mouse CD3 and anti-mouse CD45R (B220), APC-conjugated rat anti-mouse IgM, anti-mouse CD4 and anti-mouse CD8, and subclass matched control antibodies were from BD Bioscience. Mouse anti-human β-actin antibody was purchased from Sigma-Aldrich.

Isolation and Culture of Human Bone Marrow Mesenchymal Stem Cells (hBMMSCs).

BMMSCs were isolated from human whole bone marrow aspirates and cultured as described previously (Shi et al., Nat Biotechnol. 2002 20(6):587-91; Miura et al., Proc Natl Acad Sci USA. 2005; 102: 14022-14027). Human whole bone marrow aspirates from healthy adult volunteers (22-29 years old of age) (AllCells LLC) were separated using a density gradient media Ficoll-Plaque™PLUS (GE Healthcare Bioscience). Lymphocyte fraction was collected as human bone marrow mononuclear cells (MNCs). Single-cell suspension of MNCs ($1 \times 10^6$) was seeded on 150-mm culture dishes (Corning), and cultured at 37° C. for 3 h. After non-adherent cells were removed by washing with PBS, the adherent cells were cultured with advanced minimum essential medium (AdMEM) (Invitrogen) containing 5% fetal bovine serum (FBS) (Equitech-Bio), 100 μM L-ascorbic acid 2-phosphate (Wako Pure Chemicals), 2 mM L-glutamine (Biosource) and 100 U/ml penicillin/100 μg/ml streptomycin (Biosource). The medium was changed at days 7 and 14. Colonies forming cells were used as BMMSCs. The cells were passaged and sub-cultured. Passage 3-5 cells were used for this study.

Isolation and Culture of Human Skin Fibroblasts (FBs).

Human skin samples were obtained as discarded biological samples from individuals (20-50 years of age) at Harbor-UCLA/King Drew Medical Center following the approved IRB guidelines at both University of Southern California and Harbor-UCLA/King Drew Medical Center. The samples were treated aseptically and the dermal portion was digested in 4 mg/ml collagenase I (Worthington Biochemical Corporation) in sterile PBS, filtered through a 70 μm cell strainer (Falcon), and the isolated cells were cultured with AdMEM containing 5% FBS, 100 μM L-ascorbic acid 2-phosphate, 2 mM L-glutamine and 100 U/ml penicillin/100 μg/ml streptomycin. The medium was changed twice a week. The cells were passaged and sub-cultured. Passage 3-5 cells were used for this study.

Transplantation of BMMSCs and Human Skin Fibroblasts into Immunocompromised Mice.

Before subcutaneous transplantation of hBMMSCs, all of six-month-old immunocompromised mice were screened their immunodeficient condition of T and B lymphocytes and natural killer cells by flow cytometry as follows; the peripheral blood was collected from retro-orbital plexus, and stained for cell surface markers, CD45R B220 vs. IgM, CD3 vs. CD4, CD3 vs. CD8, CD3 vs. NK1.1. Subcutaneous transplantation of BMMSCs was performed on six-month-old immunocompromised mice as described previously (Shi et al., *Nat Biotechnol.* 2002 20(6):587-91; Miura et al., *Proc Natl Acad Sci USA.* 2005; 102: 14022-14027). Approximately $2.0 \times 10^6$ of BMMSCs were mixed with 40 mg of hydroxyapatite/tricalcium phosphate (HA/TCP) ceramic powder (Zimmer), and incubated at 37° C. for 90 min. The mixture was implanted subcutaneously into the dorsal surface of six-month-old immunocompromised mice. Each mouse received four BMMSC transplants. Age matched-immunocompromised mice were used as experimental controls. Additional control groups included subcutaneous transplantation of HA/TCP carrier in the presence or absence of human skin fibroblasts (FBs) ($2.0 \times 10^6$). The inventors also included a control of bone marrow transplant group using the standard intravenous infusion approach. Briefly, Mice were separately housed and routinely monitored for daily activities and health status. All mice were maintained under routine monitor until spontaneous death. Eight weeks after the transplantation, BMMSC (n=3) and FB (n=3) transplanted immunocompromised mice were harvested to collect transplants. Fourteen-month-old immunocompromised mice with BMMSC transplants (n=3) were randomly selected for BrdU-label-retaining assay. At sixteen months of age, BMMSC transplanted (n=3) and the age-matched control (n=3) immunocompromised mice were selected randomly and harvested of organ tissues, cells, peripheral blood and urine, and measurement of biomarkers. These mice were not counted for survival analysis.

Recombinant Human EPO (rhEPO) Treatment.

BMMSCs ($0.5 \times 10^6$) were seeded on a 100-mm tissue culture dished and cultured. After reaching optimal condition, rhEPO (0.1 U/ml, R&D Systems) was added. Total protein was collected at indicated times. EPO-treated (EPO+) and non-treated (EPO−) BMMSCs were harvested for flow cytometric analysis and subcutaneous transplantation with HA/TCP as a carrier into 8 week-old immunocompromised mice. Eight weeks post transplantation, three transplants from each group were harvested and analyzed.

Small Interfering RNA (siRNA) Transfection.

Human EPO-R, Stat5 and control siRNAs (Santa Cruz Biotechnology) were transfected into BMMSCs as described below. hBMMSCs ($0.5 \times 10^6$) were plated on a 100-mm tissue culture plates, and cultured for 1-2 days until the cells were reached 60-80% confluence. Human Stat5, EPO-R and control siRNAs (Santa Cruz Biotechnology) were transfected according to the manufacturer's instruction. hBMMSCs were incubated with 53 nM siRNA in a transfection medium (Santa Cruz Biotechnology) for 6 h at 37° C. and then continued to be cultured in the regular medium for 24 h. The transfected cells were harvested for further experiments. Total protein was extracted for Western blot analysis. siRNA-treated BMMSCs were transplanted with HA/TCP as a carrier into 8 week-old immunocompromised mice. Eight weeks post transplantation, three transplant tissues were harvested from each group.

BrdU-Label-Retaining Assay.

BrdU (Sigma-Aldrich, 50 mg per g body weight) was injected intraperitoneally twice daily for three days into 14 month-old immunocompromised mice which received BMMSC transplants at six month-old age. Fourteen weeks after the injection, the transplants were harvested. BrdU-labeled cells were detected on the paraffin-embedded sections using a BrdU Staining Kit (Invitrogen) according to the manufacturer's instruction.

Hematopoietic Stem Cell (HSC) Homing and Releasing Assay.

Bone marrow cells were collected from femurs and tibias of eGFP mice. The cells ($1 \times 10^6$) were intravenously injected into 8-week-old female immunocompromised mice (n=3) that initially received BMMSC transplants for eight weeks. Four weeks post-injection, BMMSC-transplants were removed and re-transplanted subcutaneously into secondary recipient 8-wee-old female immunocompromised mice (n=3). Age-matched non-transplanted mice (n=3) were used as negative controls. The peripheral blood was collected four weeks post secondary transplantation for analysis of eGFP-positive leukocytes by flow cytometry.

Micro-Computed Tomography (mieroCT) and Peripheral Quantitative CT (pQCT) Analyses.

MicroCT and pQCT analyses were performed using lumbar vertebra of 16-month-old immunocompromised mice as reported previously (Miura et al., *J Clin Invest* 2004 114 (12): 1704-1713). The bone samples were analyzed by microCT (μCT-20; SCANCO USA, Inc.). Scanning regions were confined to secondary spongiosa and were ~0.30 mm in thickness. Using 2-dimensional images, a region of interest was manually drawn near the endocortical surface. Cancellous bone morphometric indices were assessed using 3-dimensional image reconstructions including bone volume relative to tissue volume (BV/TV, %), trabecular number (Tb.N) and trabecular separation (Tb.Sp). pQCT analysis of the distal femora was performed using a XCT Research M (Stratec; Norland Co.). Briefly, scans were obtained at 2.25 and 2.75 mm from the distal condyles and cancellous BMD. Machine cancellous BMD precision (based on manufacturer data) is ±3 mg/cm3 while the coefficient of variation in the laboratory based on repeat scans was 2.26%.

Histology, Immunohistochemistry, Histochemistry and Histometry.

Brain, bone (femur, tibia and lumbar vertebra), liver and skin tissues were harvested from 16 month-old immunocompromised mice. Transplant tissues were harvested at the indicated period. All samples were fixed with 4% PFA. Bone and transplant samples were decalcified with 10% ethyl enediaminetetraacetic acid (EDTA). All samples were dehydrated and embedded in paraffin. Six-μm sections were cut and dewaxed. Sections were stained with hematoxylin and eosin (H&E). Some sections were used for immunostaining, or TRAP. Histometric analysis and quantitation of area (new bone area, bone marrow/niche area, alizarin red-positive area, total area) and cell number (immunopositive cell number, TRAP-positive cell number, total cell number) were determined using NIH Image J from five to seven images per each sample (Shi et al., *Nat Biatechnol*, 2002 20(6):587-91), followed by the mean calculation. The data were averaged in each experimental group. The intraexperimental group differences were calculated as mean values.

Immunostaining.

Sections were treated with 0.3% hydrogen peroxide and 0.1% sodium azide in PBS for 30 min, and incubated with primary antibodies overnight at 4° C. After washing with PBS, the sections were immunostained using SuperPicTure™ Polymer Detection kit (Invitrogen) according to the manufacturer's instructions. Finally, samples were lightly counterstained with hematoxylin.

Trap Staining.

The dewaxed bone sections were re-fixed with a mixture of 50% ethanol and 50% acetone for 10 min. Two TRAP-staining solutions was freshly made and mixed: 9.6 mg of naphthol AS-BI phosphate (Sigma-Aldrich) in 0.6 ml of N,N-dimethylformamide (Sigma-Aldrich) and 84 mg of fast red-violet LB diazonium salt (Sigma-Aldrich), 58.2 mg of tartaric acid (Sigma-Aldrich), and 240 µl of 10% $MgCl_2$ in 60 ml of 0.2 M sodium acetate buffer (pH 5.0). The sections were incubated for 10 min at 37° C. under shield and lightly counterstained with toluidine blue. Air-dried sections were covered to observe under a light microscope.

Blood Glucose, Serum and Urine Assay.

Glucose level in the peripheral blood was determined using a commercial blood glucose meter, Asensio. ELITE™ XL (Bayer) equipped with a blood glucose test strip, Asentia ELITE™ (Bayer) according to the manufacturer's instructions. The inventors obtained blood serum by centrifugation of peripheral blood after retro-orbital bleeding. Serum levels of IGF-I, C-terminal telopeptides of type I collagen, OPG and sRANKL were measured using commercial available kits (IGF-I, ACTIVE® Mouse/Rat IGF-I EIA, Diagnostic Systems Laboratories, TX; C-terminal telopeptides of type I collagen, RatLap ELISA kit, Nordic Bioscience Diagnostics AIS; OPG, mouse osteoprotegrin/TNFSF11B R&D Systems; RANKL, mouse TRANS/RANKUTNFSP11 Quantikine ELISA kits, R&D Systems). For measurement of Klotho level, blood serum samples and gradient mouse Klotho protein were added on 96-well multi plates at 4° C. overnight. After several washes with PBS containing 0.2% Tween 20 (PBS-T), the wells were blocked with 0.5% BSA in PBS at 4° C. overnight, followed by incubation with rat monoclonal antibody to mouse Klotho. The wells were washed with PBS-T and treated with HRP-conjugated goat anti-rat IgG (R&D Systems) at 4° C. overnight. Following another wash with PBS-T, the wells were analyzed using Mouse MonoAB ID/SP Kit (Invitrogen) and measured at 405 nm using a color photometer. Urine protein was measured by Bradford method using Bio-Rad Protein Assay (Bio-Rad Laboratories) according to the manufacturer's instruction. Each assay was measured in triplicate per each subject. The results were averaged in each group. The intra-group differences were calculated as mean values.

Isolation and Culture of Mouse BMMSCs.

mBMMSCs were isolated and cultured as previously reported (Miura et al., *J. Clin. Invest.* 2004 114(12): 1704-1713; Miura et al., *Proc Natl Acad Sci USA*. 2005; 102: 14022-14027). Single-cell suspension of all nuclear cells (ANCs) were isolated from the bone marrow of long bones by flushing with a syringe, seeded at $10\text{-}15\times10^6$ on 100-mm culture dishes (Corning) and incubated for 3 h at 37° C. ANCs ($10\text{-}15\times10^6$) from long bones of guinea pigs were added as feeder cells. To prevent proliferation in the culture the feeder cells were g-irradiated (Caesium-137) with 6,000 cGy by a Gammacell-1000 Irradiator (Atomic Energy of Canada Ltd.) before seeding. After 2 washes with PBS to remove non-adherent cells, mBMMSCs were cultured for 16 days in alpha minimum essential medium (αMEM) (Invitrogen) containing 20% FBS, 2 mM L-glutamine, 55 mM 2-mercaptoethanol (Invitrogen), 10 nM dexamethasone (Sigma-Aldrich) and 100 U/ml penicillin/100 mg/ml streptomycin. Colonies formed by mBMMSCs were passaged and sub-cultured until they reach confluence, Total protein was also extracted from passage 1 mBMMSCs.

Cfu-F Assay.

The inventors performed CFU-F assay as described previously (Miura et al., *Proc Natl Acad Sci USA*. 2005; 102: 14022-14027). Cell clusters containing >50 cells were counted as a colony under light microscopy according to the previous study (Miura et al., *Proc Natl Acad Sci USA*. 2005; 102: 14022-14027). ANCs ($1.5\times10^6$) were isolated from bone marrow, seeded on T-25 flasks (Nulge Nunc) and incubated at 37° C. After 3 h, the flasks were washed with PBS and cultured in the above medium for 16 days. After washing with PBS, cells were treated with 2% PFA and 1% toluidine blue solution. Cell clusters containing >50 cells were recognized as a colony under light microscopy. Total colony numbers were counted per flask. The CFU-F number was assayed in five experiments. The results were averaged in each group.

Cell Proliferation Assay.

The inventors performed CFU-F assay as described previously (Miura et al., *Proc Natl Acad Sci USA*. 2005; 102: 14022-14027). hBMMSCs ($1\times10^3$) and mBMMSCs ($10\times10^3$) were seeded on each well on 2-well chamber slides (Nunc) and cultured for 2-3 days. The cultures were incubated with BrdU solution (1:100) (Invitrogen) for 20 hours, and stained with a BrdU staining kit (Invitrogen) according to the manufacturer's instructions. BrdU-positive numbers were counted in ten random images. The number of BrdU-positive cells was expressed as a percentage of the total counted BMMSCs. The results were averaged in each group.

Population Doubling (PD) Assay.

The inventors performed PD assay according to previous report (Miura et al., *Proc Natl Acad Sci USA*. 2005; 102: 14022-14027). Single cell-derived colonies were trypsinized and seeded at 200-500×103 on T-75 flasks (Corning) at the first passage. At confluence, cells were removed and seeded at the same number. The PD was calculated at every passage according to the equation: PD=log 2 (number of harvested cells/number of seeded cells). The finite PDs were determined by cumulative addition of total numbers generated from each passage until cells ceased dividing. Total PD numbers were calculated in triplicate, and the results were averaged in each group.

In Vitro Osteogenic Assay.

BMMSCs were cultured for osteogenic induction as previously reported (Miura et al., *Proc Nall Acad Sci USA*. 2005; 102: 14022-14027). BMMSCs were cultured in α-MEM containing 20% FBS, 2 mM β-glycerophosphate, (Sigma-Aldrich), 100 mM L-ascorbic acid phosphate, 10 nM dexamethasone, 2 mM L-glutamine, 55 mM 2-mercaptoethanol, 100 U/ml penicillin/100 µg/ml streptomycin for 6 weeks. The calcium deposits were identified using alizarin red staining. Alizarin red positive and total area was measured using an NIH image J from five to seven images per each sample, followed by the mean calculation. Cells were analyzed in three to five experiments. The data were averaged in each experimental group (Shi et al., *Nat Biotechnol.* 2002 20(6):587-91; Miura et al., *Proc Natl Acad Sci USA.* 2005; 102: 14022-14027). The intra-experimental group differences were calculated as mean values.

In Vivo Osteogenic Assay.

mBMMSCs ($2.0 \times 10^6$) were implanted subcutaneously with HA/TCP as a carrier into eight-week-old immunocompromised mice. Eight weeks post-transplantation, the transplants were harvested.

Flow Cytometric Analysis.

The inventors immunostained cells for flow cytometry as described previously (Shi et al., *Nat Biotechnol.* 2002 20(6): 587-91), and analyzed by using a FACScalibur flow cytometer (BD Bioscience).

Single cell suspension ($2 \times 10^5/100$ μl/tube) in a wash buffer containing 5% heat-inactivated FBS in PBS was used for immunostaining. For indirect immunostaining, cells were incubated with 100 μl of antiserum or 1 μg of each antibody or isotype-matched immunoglobulin for 45 min on ice. After washing with a wash buffer at 4° C., they were incubated with R-PE conjugated secondary antibody for 30 min on ice. For direct immunostaining, cells were treated with 1 μg of each R-PE conjugated antibody for 45 min on ice. After washing, cells were sorted on a FACSCalibur flow cytometer (BD Bioscience). Cell counts were calculated in triplicate and the results were averaged in each group.

Rt-PCR Analysis.

cDNA was obtained from total RNA extracted from cultured cells, and amplified.

Total RNA was extracted from cultured cells using TRIizol® regaent (Invitrogen) following the manufacturer's instructions, and treated with DNase I to remove genome DNA contamination. cDNA was obtained from total RNA using SuperScript™ II (Invitrogen), and mixed with a specific primer pair in Platinum® Blue PCR SuperMix (Invitrogen). PCR products were amplified under the following condition; denature: 94° C. for 30 sec, annealing: 55° C. for 30 sec, extension: 72° C. for 1 min. The products were analyzed by gel electrophoresis and stained with ethidium bromide. The specific primer pairs for human EPO-R and glyceraldehyde 3 phosphate dehydrogenase (G3PDH) were as follows; EPO-R (GenBank accession no. NM_000121), sense: 5'-GAGCATGCCCAGGATACCTA-3' (nucleotides 1220-1239) (SEQ ID: 1), anti-sense: 5'-TACT-CAAAGCTGGCAGCAGA-3' (nucleotides 1394-1413) (SEQ ID: 2): G3PDH (GenBank accession no. BK000280), sense: 5'-CTGGCCTCCAGCTACATCTC-3' (nucleotides 12-31) (SEQ ID: 3), anti-sense: 5'-TCATATTTGGCAG-GTTTTTCT-3' (nucleotides 807-827) (SEQ ID: 4).

Western Blot Analysis.

Western blot analysis was followed as in previous study (Shi et al., *Nat Bioteehnol.* 2002 20(6):587-91). Cells and tissue samples were lysed in M-PER extraction reagent (Pierce). Ten μg of total protein per well was applied onto NuPAGE gel (Invitrogen). The separated proteins were transferred on to Immobilon membranes (Millipore), and treated with a blocking buffer consisting of 4% bovine serum albumin (BSA), 1% non-fat dry milk, 154 mM NaCl, 0.05% Tween 20 in 10 mM Tris-HCl (pH 7.5) for 60 min. After washing, the membranes were incubated with primary antibodies in an incubation buffer consisting of 0.5% BSA, 154 mM NaCl, 0.05% Tween 20 in 10 mM Tris-HCl (pH 7.5) at 4° C. for overnight. After incubated with horseradish peroxidase (HRP)-conjugated goat anti-rabbit antibody (Santa Cruz Biotechnology) in the incubation buffer for 60 min, the membranes were treated with a HRP substrate with West-Pico (Pierce) to enhance the reaction. Membranes were stripped using stripping buffer (Pierce) and re-probed with ®-actin, followed by incubation with HRPconjugated rabbit anti-mouse antibody (Santa Cruz Biotechnology) to quantity the amount of protein loading. Western blotting was performed in three independent experiments. Band intensity was measured using NIH Image J, and calculated the means in each group.

Statistical Analysis.

Student t-test and Mantel-Haenszel test were used to analyze significance between two groups. P<0.05 was considered significant. Kaplan-Meier was used for survival curve analysis.

Experiment 2

2.1 Systemic Lupus Erythematosus (SLE) Model MRL/Lpr Mice Showed BMMSC Impairment and Osteoblastic Niche Deficiency.

Osteoporosis is commonly reported in SLE patients secondary to long-term use of glucocorticoids and cyclophosphamide. We verified the osteoporotic changes in the skeletal structures of naïve CD95-mutant MRL/lpr mice by micro-radiographic and bone morphometric analyses. The femurs of MRL/lpr mice at age of 20 weeks showed remarkable reduction in BMD (FIG. 7A) and significant atrophy of trabecular bone (FIG. 7B) with reduced bone volume (FIG. 7C), trabecular number (FIG. 7D) and bone surface area (FIG. 7E) and increased trabecular separation (FIG. 7F). These findings indicated that the skeletal system of naïve MRL/lpr mice undergoes changes typical of osteoporosis phenotype.

Since T-lymphocyte over-activation has been associated with BMMSC impairment and osteoporosis, we next examined whether T-lymphocytes are over-activated in MRL/lpr mice and their effects on BMMSCs. We showed that BMMSCs derived from MRL/lpr mice (MRL/lpr-BMMSCs) displayed an increase in the number of CFU-F, representing the number of clonogenic mesenchymal progenitors, as compared to control mice (FIG. 7G), and an elevated proliferation rate by BrdU incorporation assay (FIG. 7H). MRL/lpr-BMMSCs also showed impairment of osteogenic differentiation, shown here as a decreased mineralization in osteo-inductive cultures (FIG. 7I), and decreased levels of osteogenic gene expression, including runt-related transcription factor 2 (Runx2), alkaline phosphatase (ALP), and osteocalcin (OCN) assessed by both semiquantitative RT-PCR (FIG. 7J) and Western blot analyses (FIG. 7K). The in vitro findings were further confirmed with in vivo studies in immunocompromised mice (FIG. 9D), showing reduced bone (It seems that the term of nodule is not adequate to show bone formation in vivo) formation when subcutaneously transplanted using HA/TCP as a carrier. Additionally, MRL/lpr-BMMSCs demonstrated impairment of adipo genic differentiation as shown by decreased numbers of lipid-specific Oil red O-positive cells (FIG. 7L) and reduced expression of adipocytespecific genes, peroxisome proliferator-activated receptor gamma 2 (PPARγ2) and lipoprotein lipase (LPL) by semi-quantitative RT-PCR (FIG. 7M). These findings suggest that BMMSCs derived from MRL/lpr mice were functionally impaired compared to control mice. In contrast to BMMSC/osteoblast lineage, osteoclasts play a significant role in the maintenance of bone homeostasis by their bone resorption function. We examined osteoclast activity in MRL/lpr mice and found an increased number of TRAP positive osteoclasts in the distal femur epiphysis of MRL/lpr mice (FIG. 7N), elevated serum levels of sRANKL, a critical factor for osteoclastogenesis, (FIG.

7O) and bone resorption marker C-terminal telopeptides of type I collagen (FIG. 7P) as compared to control mice. These findings revealed that over-activated osteoclasts in MRL/lpr mice potentially contribute to bone loss in SLE-like disease.

2.2 Allogenic BMMSC Transplantation (MSCT) Improves Multiple Organ Function in MltUlpr Mice.

SLE-like multi-systemic autoimmune disorders usually appear at age 7-8 weeks in MRL/lpr mice. To explore the effects of early versus late treatment interventions, we infused allogenic BMMSCs into MRL/lpr mice either at an early stage of the SLE disorder (9 weeks of age, MSCT9), or at the matured stage (16 weeks of age, MSCT16) (FIG. 8A). Cyclophosphamide (CTX) treatment at 9 weeks of age was used as a conventional treatment control (FIG. 8A). It has been reported that autoantibodies play a crucial role in multiple organ impairment in SLE patients. Consistent with human findings, MRL/lpr mice showed a remarkable increase in circulating autoantibodies, specifically antidouble strand DNA (dsDNA) IgG and IgM antibodies (FIG. 8B), anti-nuclear antibody (ANA) (FIG. 8C), and immunoglobulins including $IgG_1$, $IgG_{2a}$, $IgG_{2b}$ and IgM (FIG. 8G) in the peripheral blood. Initiating MSCT at both early and matured stages, 9- and 16-week-olds, benefited a significantly reduction in serum levels of anti dsDNA antibody IgG and IgM, ANA, immunoglobulins $IgG_1$, $IgG_{2a}$, $IgG_{2b}$ and IgM (FIGS. 8B, C, and G). In addition, decreased serum albumin levels in MRL/lpr mice were observed after MSCT (FIG. 8D). When compared to MSCT, conventional CTX treatment only partially reduced levels of serum autoantibodies, immunoglobulin IgG2a and recovered albumin level in MRL/lpr mice (FIGS. 8B-D, and G). In addition, unlike MSCT, CTX treatment failed to reduce circulating immunoglobulins IgG1, IgG2b and IgM in MRL/lpr mice (FIG. 8G).

Figure 8E:
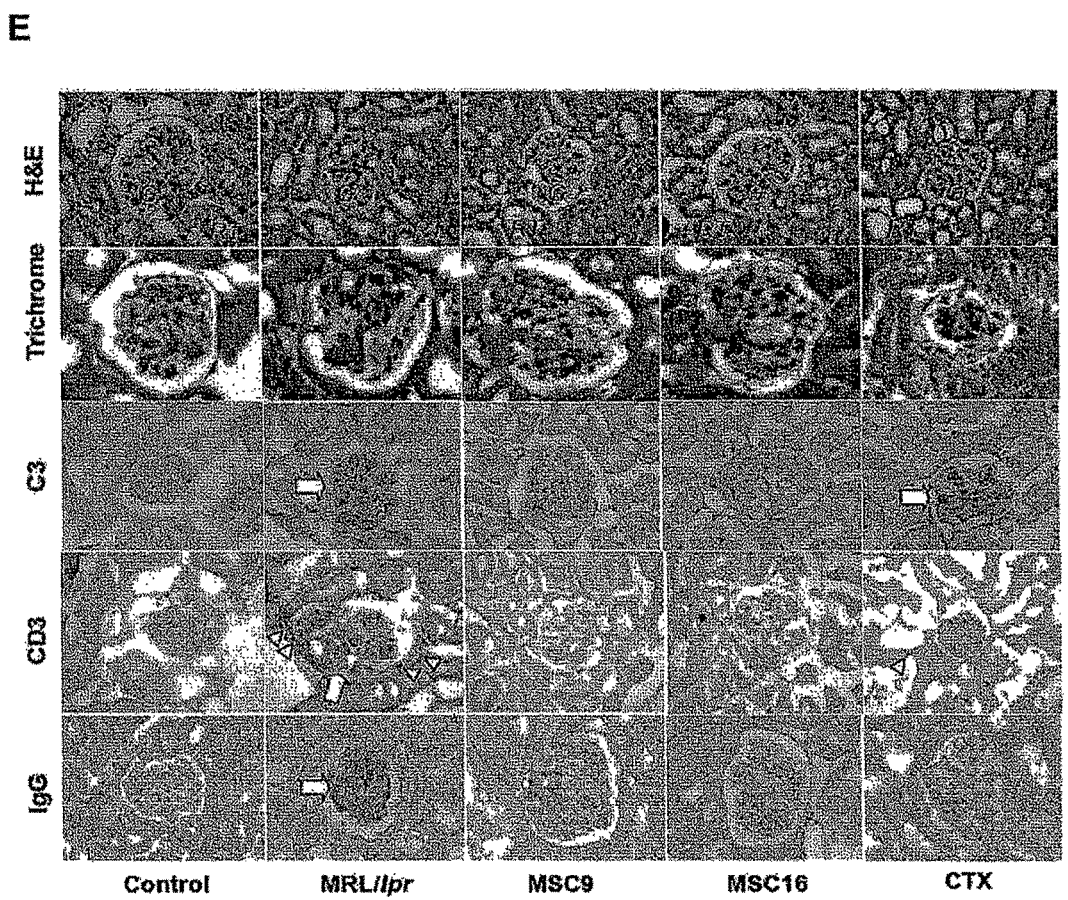
FIG. 8 shows data demonstrating that allogenic mesenchymal stem cell transplantation (MSCT) reduced levels of autoantibodies and improved renal function in MRL/lpr mice. (A) The scheme of allogenic MSCT and cyclophosphamide (CTX) treatment procedures. (B) ELISA quantified that levels of anti double strand DNA (dsDNA) IgG and IgM antibodies (mean±SD) were significantly increased in the peripheral blood of MRL/lpr mice (n=6) when compared to the undetectable level (N.D.) in controls (n=6). MSCT at 9 weeks (MSC9, n=6) and at 16 weeks (MSC16, n=6) and CTX treatment (CTX, n=6) were able to reduce levels of anti dsDNA IgG and IgM, but failed to reduce the levels of anti dsDNA IgG and IgM at the undetectable level as shown in controls. ($^{III}P<0.001$ vs. Control; $^{\#\#\#}P<0.001$ vs. MRL/lpr). (C) MSCT (MSC9, n=6, and MSC16, n=6) and CTX treatment (n=6) were able to significantly reduce anti nuclear antibody (ANA) (mean±SD) in MRL/lpr mice (n=6), which was significantly increased compared to the control (n=6). But the levels at the post treatments were higher than the control. ($^{III}P<0.001$ vs. Control; $^{\#\#\#}P<0.001$ vs. MRL/lpr). (D) MSC9 (n=6) appeared to increase albumin level (mean±SD) compared to the level in MRL/lpr mice (n=6), which were significantly decreased compared to the control (n=6). MSC16 (n=6) and CTX treatments (n=6) were also able to significantly elevate the levels, which were still significantly lower than the control. ($^{III}P<0.001$ vs. Control; $^{I}P<0.05$ vs. Control; $^{\#\#\#}P<0.001$ vs. MRL/lpr). (E) MSCT, as well as CTX treatment, reduced basal membrane disorder and mesangium cell over-growth in glomerular (G) (upper panels, H&E staining; upper second panels, trichrome staining). RT: renal tubule. Immunohistochemistry showed MSCT was able to diminish complement 3 (C3) deposition in glomerular (open arrow) of MRL/lpr group, however, CTX treatment failed to reduce C3 in glomerular (open arrow) (middle panels). All treatments were capable of infiltration of CD3-positve cells and reducing IgG deposition in glomerular of MRL/lpr group (lower panels). (F) All treatments (MSC9, n=6; MSC16, n=6; CTX, n=6) significantly reduced urine protein levels (mean±SD) in MRL/lpr mice, which significantly increased when compared to control mice (n=6). ($^{III}P<0.001$ vs. Control; $^{I}P<0.05$ vs. Control; $^{\#\#}P<0.01$ vs. MRL/lpr). (G) Markedly increased urine immunoglobulins (IgG$_1$, IgG$_{2a}$, IgG$_{2b}$, and IgM) (mean±SD) in MRL/lpr mice (n=6) were significantly reduced after allogenic MSCT (MSC9, n=6; MSC16, n=6). CTX treatment (n=6) was not effectively in reducing the immunoglobulins levels. [$^{III}P<0.005$ vs. Control; $^{I}P<0.05$ vs. Control; $^{\#\#\#}P<0.005$ vs. MRL/lpr; #P<0.05 vs. MRL/lpr; $^{\$\$\$}P<0.005$ vs. MSCT (MSC9 and MSC16); $^{\$}P<0.05$ vs. MSCT (MSC9 and MSC16)].

As expected, MRL/lpr mice showed renal disorders such as nephritis with glomerular basal membrane disorder, mesangial cell over-growth, deposition of complement component 3 (C3) and IgG, and infiltration of CD3-positive cells (FIG. 8E). In addition, we found presence of increments of urine protein (FIG. 8F) and immunoglobulins including $IgG_1$, $IgG_{2a}$, $IgG_{2b}$ and IgM in MRL/lpr mice (FIG. 8G). In general, MSCT at both early and matured stages was able to improve renal disorders (FIG. 8E-8G), specifically restoring kidney glomerular structure, and reducing C3 and glomerular IgG deposition (FIG. 8E). Although CTX treatment could reduce glomerular IgG deposition, it did not restore the glomerular structure and C3 accumulation as compared to MSCT (FIG. 8E). In response to either MSCT or CTX treatment, MRL/lpr mice showed reduced urine protein levels at 4 weeks post treatment (FIG. 8F). These experimental evidences indicated that MSCT is a superior therapeutic approach for treating nephritis in MRL/lpr mice and capable to restore renal function.

2.3 Allogenic MSCT Ameliorates Osteoporosis-Like Phenotype in MRL/Lpr Mice, and Improves the Osteoblastic Niche.

To examine whether MSCT is capable of recovering skeletal disorder in MRL/lpr mice, we analyzed the bone phenotype and BMMSC function in MSCT-treated MRL/lpr mice compared to CTX-treated and non-treated mice. Bone histomorphometric analysis with H&E revealed that MSCT at both early and matured stages was capable of promoting trabecular bone formation and inhibiting osteoclastogenesis (FIG. 9A). It has been recognized that osteoblasts, differentiated from their progenitor BMMSCs, contribute to niche organization for HSC in the bone marrow compartment. Consistent with this observation, we showed that MSCT significantly improved osteoblastic niche reconstruction in MRL/lpr mice (FIG. 9B) evidenced by an increase in new bone and marrow formation. However, CTX treatment was not able to improve bone volume and reconstruct osteoblastic niche (FIGS. 9A, 9B). BMMSCs derived from MSCT-treated MRL/lpr mice showed significantly increased new bone formation (FIG. 9C, 9D) and osteoblastic niche regeneration (FIG. 9C, 9E) when transplanted into immunocompromised. mice. In addition, MSCT appeared to suppress the high colony formation of BMMSCs derived from MRL/lpr shown as a significant reduction in number of CFU-F in treated mice (FIG. 9F). CTX treatment showed similar treatment effects to MSCT, however at a lower extent (FIG. 9C-F). These findings suggest that allogenic MSCT provided an optimal therapy for improving bone volume and BMMSC function in MRL/lpr mice as compared to conventional CTX.

2.4 Allogenic MSCT Restores the Immune System via $CD4^+$ $CD25^+$ Forkhead Box P3(Foxp3)$^+$ Cell, Interleukin 17 (IL17) Secreting Helper T Cells (Th17 Cells), and Plasma Cells.

It has been suggested that $CD4^+CD25^+Foxp3^+$ cells prevent pathogenic autoimmunity by suppressing proliferation and production of proinflammatory cytokines in effector immune cells, such as helper T-lymphocytes. In contrast, Th17 cells, an inflammatory IL17 producing cell, have been linked to the pathogenesis of autoimmune diseases and bone destruction. To explore whether MSCT affects the immune balance between $CD4^+CD25^+Foxp3^+$ cells and Th17 cells in SLE-like disorders, we studied Foxp3+ cells and Th17 cells in spleen and bone marrow of MRL/lpr mice. MSCT at both early and matured stages was able to restore Foxp3$^+$ cells in MRL/lpr mice (FIG. 10A). However, CTX treatment only slightly increased the level of Foxp3 (FIG. 10A). Immunohistochemical analysis showed that IL17-positive cells were significantly increased in bone marrow and spleen of MRL/lpr mice when compared to control mice, and were specifically suppressed by MSCT (FIG. 10B, 10C). Flow cytometry also demonstrated that the increased in $CD4^{+IL}17^+$ T-lymphocytes in bone marrow and spleen of MRLlpr mice was significantly reduced by MSCT at both early and matured stages, as compared to CTX treatment (FIG. 10E). Semi-quantitative RT-PCR analysis further confirmed the decreased IL17 gene expression in both bone marrow and spleen of MSCT mice (FIG. 10D, 10F). Likewise, CTX treatment also reduced IL17 levels in MRL/lpr mice (FIG. 10B-10F). Moreover, ELISA analysis showed that IL17 levels were remarkably increased in spleen of MRL/lpr mice and MSCT, but not CTX treatment, significantly suppressed the elevated IL17 levels (FIG. 11A).

Since MSCT is capable of suppressing the levels of autoantibodies in MRL/lpr mice, we examined whether MSCT regulates CD138-positive plasma cells, an immunoglobulin producing cell. In MRL/lpr mice, CD138-positive cells were significantly increased compared to control mice by immunohistochemistry (FIG. 11B). MSCT reduced the number of CD138-positive cells in MRL/lpr mice (FIG. 11B). ELISA also showed that allogenic MSCT was able to reduce the levels of anti-dsDNA IgG, and immunoglobulins, $IgG_1$, $IgG_{2a}$, $IgG_2$, and IgM, in spleen of MRL/lpr mice (FIG. 11C, 11D). Although CTX appeared capable of inhibiting the number of CD138-positive cells and the production of both autoantibodies and immunoglobulins, this conventional treatment was not as effective as MSCT (FIG. 11B, 11C). These results suggest that allogenic MSCT is a more improved therapy with a better treatment effect than conventional CTX in SLE-like MRL/lpr mice, possibly through the modulation of multiple immune cells.

2.5 BMMSCs Derived from SLE Patients Showed Osteogenic Impairment.

Previous study suggested that BMMSCs from SLE patients might show differentiation impairment similar to those observed in SLE mice. To verify the findings in humans, we isolated BMMSCs from two SLE patients and characterized their osteogenic differentiation properties in vivo using subcutaneous transplantation in immunocompromised mice. BMMSCs derived from SLE patients showed significantly decreased bone forming capacity and impaired reconstruction of bone marrow in vivo as compared to BMMSCs from matched normal healthy subjects (FIG. 12A). Furthermore, semi-quantitative RT-PCR analysis revealed decreased expression of osteogenic genes Runx2 and OCN in BMMSCs from SLE patients (FIG. 12B). Given the evidence that some advanced stage SLE patients may have experienced a suppression of $CD34^+$ bone marrow cells, it is postulated that the decrease in $CD34^+$ subset may correlate with the osteoblastic niche deficiency in the bone marrow of SLE patients. Allogic MSCT is a safe and feasible salvage therapy in patients with refractory SLE. Since our animal study showed that MSCT, but not CTX treatment, offered improved clinical outcomes and reversed multi-organ dysfunction in SLE, we hypothesized that MSCT may be capable of curing CTX-refractory SLE patients. To test this hypothesis, we conducted a pilot clinical study to assess the efficacy and safety of MSCT in a small cohort group of SLE patients. Three female and one male patients in the age range of 16 to 23 years old, with treatment-refractory SLE for duration of 12-51 months were enrolled for allogenic MSCT. All subjects met the revised criteria for SLE established by the American College of Rheumatology (ACR, 1997) and had been previously treated with CTX and high dose of prednisone (more than 20 mg/day). Patient eligibility criteria also included lupus glomerulonephritis (class III, IV, V) with severe elevation of increment of 24-hour urine protein levels and/or serum creatinine ≥1.5 mg/dl. Bone marrow was collected from patients' healthy family member and ex vivo expanded in culture under GLP/GMP protocols. MSCT were infused at ≥1×106 cells/kg body weight. Primary outcomes were overall survival and disease remission defined as requiring no further high dose of immunosuppressive medications except the low maintenance doses of corticosteroids and CTX. Post MSCT maintenance therapy includes a tapering dose of steroid and CTX, with 2 patients completely off CTX at 6 months, and 2 patients on low dose of CTX at 0.6 mg/every 2 months. Secondary outcomes included systemic lupus erythematosus disease activity index (SLEDAI), complement C3, and renal function monitored by 24-hour urine protein levels. Our short-term clinical outcome in 12-18 months follow up post-MSCT showed no allogenic MSCT-related complications including cardiovascular, pulmonary insufficiencies, infection, malignancy, and metabolic disturbances. Assessment of SLEDAI indicated the improvement of disease activity in all allogenic MSCT-treated patients at each follow-up period (FIG. 12D), All recipients were followed up for 12-18 months and showed recovery of kidney function with low baseline 24-hour urine protein levels (FIG. 12E). Serum C3 level improved at one-month post MSCT in all patients, from 0.4775±0.1134 g/L to 0.7750±0.0826 g/L. These early clinical data demonstrate safety and efficacy of MSCT in SLE patients and improvement of disease activities at post allogenic MSCT. Further longterm follow ups and additional patient enrollment are in progress.

Interestingly, we also found increased levels of $CD4^+$ $Foxp3^+$ cells followed allogenic MSCT in 3 SLE patients with statistical significance at three-month post MSCT (FIG. 12F). The MSCTassociated increased level of $CD4^+Foxp3^+$ cells in these treated patients correlates with similar findings of recovery of $Foxp3^+$ cells in MRL/lpr mice followed MSCT (FIG. 10A). Further studies are needed to uncover the underlying mechanisms of MSCT induced immune regulation in ameliorating SLE disease activities in refractory patients.

Materials and Methods

Mice.

Female C3MRL-Fas$^{lpr}$/J (MRL/lpr) (4-7 week-old) and background matched C3H/HeJ mice (4-7 week-old) were purchased from the Jackson Laboratory. Female immunocompromised mice (Beige Nude XIDIII (nu/nu), 8-12 week-old) were purchased from Harlan. All animal experiments were performed under an institutionally approved protocol for the use of animal research (USC #10874 and #10941). The mice were maintained in a temperature-controlled room with a 12-h alternating light-dark cycle and fed sufficient diet and water ad libitum throughout the experimental period.

Antibodies.

Purified anti-mouse IgG and anti-CD138 antibodies were purchased from R&D Systems. Purified anti-IL17 and anti-Runx2 antibodies were obtained from Santa Cruz and Oncogene, respectively. Purified C3 antibody was form GeneTex. Anti-CD3 antibody was purchased from abcam. Anti-ALP (LF47) and anti-OCN (LF32) were kindly provided by Dr. Larry Fisher (National Institute of Dental and Craniofacial Research, National Institutes of Health). Anti-β-actin antibody was purchased from Sigma. APC-conjugated and PerCP-conjugated anti-CD4, APC-conjugated anti-CD25, PE-conjugated anti-CD138 and PE-conjugated anti-IL17, were from BD Bioscience. PE-conjugated anti-Foxp3 antibody was obtained from Miltenyi Biotech. Antibodies for mouse immunoglobulins IgG, IgA and IgM were purchased from Invitrogen.

Bone Phenotype Analysis.

MicroCT and pQCT analyses were performed as previously described (Miura et al., *J Clin Invest* 2004; 114:1704-1713). Distal femoral metaphyses were harvested from 20-week-old mice. Distal femoral metaphyses were analyzed by μCT (ScanXmate-A100S; Comscantecno Co. Ltd., Kanagawa, Japan). Scanning regions were confined to secondary spongiosa and the thickness was approximately 1.0 mm. Using 2-dimensional images, a region of interest was manually drawn near the endocortical surface. Structual indices and BMD were calculated using 3-dimensional image analysis system (TRI/3D-Bon software; Ratoc System Enginerring Co. Ltd.). Structural indices are including bone volume/trabecular volume (BV/TV), bone surface area (BS, mm2), trabecular number (Tb.N, 1/mm), and trabecular separation (Tb.Sp, mm).

Mineralized Tissue Analysis.

Femurs and transplant tissue were fixed with 4% PFA in phosphate buffered saline (PBS), pH 7.2, overnight at 4° C., and decalcified with 5% EDTA (pH 7.4) in PBS, pH 7.2, for 10 days at 4° C. Bone samples were dehydrated with a graduate series of ethanol, cleaned with xylen, and immersed in paraffin. The samples were embedded in paraffin and cut into 8-μm-thick sections. The sections were deparaffinized, rehydrated and used for H&E staining and further histochemical staining.

Paraffin sections were used for histological analysis, including H&E staining, TRAP staining and immunohistochemistry.

Trap Staining.

Deparaffinized sections were re-fixed with a mixture of 50% ethanol and 50% acetone for 10 min. TRAP-staining solutions were freshly made (1.6% naphthol AS-BI phosphate in N, N-dimethylformamide and 0.14% fast red-violet LB diazonium salt, 0.097% tartaric acid and 0.04% $MgCl_2$ in 0.2 M sodium acetate buffer, pH 5.0) and mixed in 1:10. The sections were incubated in the solution for 10 min at 37° C. under shield and counterstained with toluidine blue. All regents for TRAP staining were purchased from Sigma.

Immunohistochemistry.

Sections were treated with 0.3% hydrogen peroxide and 0.1% sodium azide in PBS, pH 7.2, for 30 min, and incubated with indicated primary antibodies, overnight, at 4° C. After washing with PBS, the sections were immunostained using SuperPicTure™ Polymer Detection kit (Invitrogen) according to the manufacturer's instructions. Finally, samples were counterstained with hematoxylin.

Mouse BMMSC Isolation and Culture.

Bone marrow cells were flashed out from bone cavity of femurs and tibias with heat-inactivated 3% fetal bovine serum (FBS; Equitech-Bio) in PBS. All nuclear cells (ANCs) were seeded at $10\text{-}20 \times 10^6$ into 100 mm culture dishes (Corning) and initially incubated for 3 hours under 37° C. at 5% $CO_2$ condition. To eliminate the non-adherent cells, the cultures were washed with PBS twice. The attached cells were cultured for 14-16 days. Colonies-forming attached cells were passed once to use for further experiments. The BMMSCs were cultured with α-MEM (Invitrogen) supplemented with 20% FBS, 2 mM L-glutamine (Invitrogen), 55 μM 2-mercaptoethanol (Invitrogen) and antibiotics (100 U/ml penicillin and 100 μg/ml streptomycin; Biofluids).

Allogenic Mouse BMMSC Transplantation into MRL/Lpr Mice.

Under general anesthesia, C3H/HeJ-derived BMMSCs ($0.1 \times 10^6$ cells/10 g body weight) were infused into MRL/lpr mice via tail vein at different ages of 9 weeks (n=12) and 16 weeks (n=12). In control group, MRL/lpr mice (9-week-old) received PBS (n=12) or cyclophosphamide monohydrate (Sigma) (200 μg/g body weight) (n=12) and age-matched Mesenchymal stem cells and Systemic Lupus Erythematosus 3 C3H/HeJ mice (n=12) were used. All mice were sacrificed at 20 weeks of age for further analysis.

Sle Patients.

Four patients (three female and one male) at age 16, 17, 20, and 23 were treated with CTX (0.75 g/m² per month) and prednisone (≥20 mg/day) for more than six months. The treatment was ineffective in these patients as shown in the SLE disease activity index (SLEDAI) (more than 8) and lupus nephritis (24 h urine protein ≥1 g and/or serum creatinine ≥1.5 mg/dl) without end-stage renal failure. Four healthy patients' relatives, at age 19 (male), 42 (male), 43 (male) and 46 (female) were selected as donors. All of the recipients and donors gave informed consent to enroll in the clinical study. This clinical study was approved by the Ethics Committee of the Affiliated Drum Tower Hospital of Nanjing University Medical School and registered at ClinicalTrials.gov (Identifier: NCT00698191).

Culture and Expansion of Human BMMSCs.

Human bone marrow aspirates were collected from iliac of four donors and two SLE patients (Shi et al., *Nat Biotechnol.* 2002 20(6):587-91; Miura et al., *Proc Natl Acad Sci USA.* 2005; 102: 14022-14027). Human bone marrow aspirated from iliac of eight donors selected from relatives of the patients and two SLE patients were diluted with PBS containing heparin (1,250 U/ml) and separated using Ficoll-Hypaque (density 1.077 g/ml, TBD) by centrifuge at 2000 rpm for 30 minutes to obtain mononuclear cells. The single cell suspensions ($5 \times 10^6$/ml) were cultured in 25 cm² flasks (Corning) with DMEM supplemented with 10% FBS and antibiotics at 37° C. with medium change every 24-48 hours until the BMMSCs achieved required numbers at 3-4 passages. The BMMSCs were used for in vivo transplantation and in vitro osteogenic differentiation. For the allogenic MSCT, human SLE BMMSCs were cultured under non-serum-depleted condition for 12 hours prior to MSCT, and repeatedly washed with 0.25% trypsin and then mixed with 5% human albumin in physiological saline.

Allogenic Human BMMSC Transplantation in SLE Patients.

Donor BMMSCs from patients' family members were intravenously infused in eligible SLE recipients ($\geq 1 \times 10^6$/kg body weight). Prednisone 20-30 mg was administrated to recipient patients prior to the MSCT procedure. Post MSCT maintenance therapy includes a tapering dose of steroid and CTX, with 2 patients completely off CTX at 5-6 months. Specific maintenance therapy for all 4 patients are as followed: 1) patient#1: prednisone 10 mg/day and CTX 0.6 g/every 2 months for 6 months, then prednisone 5 mg/day and CTX 0.6 g/every 2 months for 12 months; 2) patients #2: prednisone 10 mg/day and CTX 0.6 g/every 2 months for 7 months, then prednisone 10 mg/day with no CTX for 5 months; 3) patients #3: prednisone 10 mg/day and CTX 0.6 g/every 2 months for 7 months, then prednisone 5 mg/day and CTX 0.6 g/every 2 months for 5 months; 4) patients #4: prednisone 10 mg/day and CTX 0.6 g/every 2 months for 6 months, then prednisone 10 mg/day with no CTX for 6 months.

Cfu-F Assay.

CFU-F assay was performed according to previous study (Miura et al., *J Clin Invest* 2004; 114:1704-1713). ANCs ($1.5 \times 10^6$/flask) were seeded on T-25 flasks (Nunc) and incubated at 37° C. After 3 hours, the flasks were washed with PBS and cultured for 16 days. After washing with PBS two times, the flasks were treated with 2% PFA and 1% toluidine blue solution in PBS. Cell clusters containing ≥50 cells were recognized as a colony under light microscopy. Total colony numbers were counted per flask. The CFU-F number was repeated in five or six independent samples per each experimental group.

Cell Proliferation Assay.

The proliferation of BMMSCs was evaluated by BrdU incorporation as previously described (Miura et al., *J Clin Invest* 2004; 114:1704-1713). Mouse BMMSCs ($10 \times 10^3$/well) were seeded on 2-well chamber slides (Nunc) and cultured for 2-3 days. The cultures were incubated with BrdU solution (1:100) (Invitrogen) for 20 hours, and stained with a BrdU staining kit (Invitrogen) according to the manufacturer's instructions. The samples were stained with hematoxylin. BrdU-positive and total cell numbers were counted in ten images per subject. The number of BrdU-positive cells was indicated as a percentage to the total cell number. The BrdU assay was repeated in five or six independent samples for each experimental group.

In Vitro Differentiation Assay.

In vitro osteogenic and adipogenic induction of mouse BMMSCs were performed as described previously (Miura et al., *J Clin Invest* 2004; 114:1704-1713). BMMSCs were cultured under osteogenic culture condition containing 2 mM β-glycerophosphate (Sigma), 100 µM L-ascorbic acid 2-phosphate (Wako Pure Chemicals) and 10 nM dexamethasone (Sigma). After the osteo-induction, the cultures were stained with alizarin red. For the adipo-induction in vitro, 500 nM isobutylmethylxanthin (Sigma), 60 µM indomethacin (Sigma), 500 nM hydrocortisone (Sigma), 10 µg/ml insulin (Sigma), 100 nM L-ascorbic acid phosphate were added into the medium. Two weeks after the adipo-induction, the cultures were stained with Oil Red-O. The mineralized area and Oil Red-O positive cells were quantified by using an NIH Image-J. Total RNA and total protein were isolated from the mouse BMMSC cultures after two weeks inductions. All experiments were repeated in five or six independent samples for each group.

In Vivo Bone Formation Assay.

BMMSCs were subcutaneously transplanted into immunocompromised mice using hydroxyapatite tricalcium phosphate (HAITCP) as a carrier (Shi et al., *Nat Biotechnol* 2002; 20:587-591). Approximately $4.0 \times 10^6$ of BMMSCs were mixed with 40 mg of HA/TCP ceramic powder (Zimmer) as a carrier and subcutaneously transplanted into the dorsal surface of 8-10 weeks old immunocompromised mice. Eight weeks post-transplantation, the transplants were harvested, fixed in 4% PFA and then decalcified with 10% EDTA (pH 8.0), followed by paraffin embedding. Paraffin sections were deparaffinized and stained with H&E.

Rt-PCR Analysis.

Total RNA was isolated from cultures. The cDNA was amplified with specific primers. The specific primers were listed on Table 1. Total RNA was isolated from the cultures using SV total RNA isolation kit (Promega) and digested with DNase I following the manufacture's protocols. The cDNA was synthesized from 100 ng of total RNA using Superscript III (Invitrogen). And then, PCR was performed using gene specific primers and Platinum PCR supermix (Invitrogen). The amplified PCR products were subjected to 2% agarose gels which contain ethidium bromide and visualized by UV fluorescent. The intensity of bands was measured by using NIH image-J soft ware and normalized to GAPDH. RT-PCR was repeated in five or six independent samples.

Western Blot Analysis.

Western blot analysis was performed as described previously (Shi et al., *Nat Biatechnol* 2002; 20:587-591). Total RNA was isolated from the cultures using SV total RNA isolation kit (Promega) and digested with DNase I following the manufacture's protocols. The cDNA was synthesized from 100 ng of total RNA using Superscript III (Invitrogen). And then, PCR was performed using gene specific primers and Platinum PCR supermix (Invitrogen). The amplified PCR products were subjected to 2% agarose gels which contain ethidium bromide and visualized by UV fluorescent. The intensity of bands was measured by using NIH image-J soft ware and normalized to GAPDH. RT-PCR was repeated in five or six independent samples.

Measurement of Biomarkers in Blood Serum, Urine and Spleen.

Peripheral blood serum, urine samples, and total protein from spleen were collected from mice. Autoantibodies, albumin, immunoglobulins, RANKL, C-terminal telopeptides of type I collagen, IL-6, IL-17 and TGFβ in the serum and spleen Mesenchymal stem cells and Systemic Lupus Erythematosus 4 were analyzed by ELISA. The protein concentration in urine was measured using Bio-Rad Protein Assay (Bio-Rad).

ELISA.

Peripheral blood were collected from the retro-orbital plexus, and centrifuged to obtain the blood serum. Urine was also collected. Tissue lysates were extracted from mouse spleen. The samples were centrifuged and used for ELISA. Anti-dsDNA IgG and IgM antibodies, ANA, albumin, C3, IL17, IL6, sRANKL and C-terminal telopeptides of type I collagen were measured using commercial available kits (anti-dsDNA antibodies, ANA, albumin, C3, alpha diagnostic; IL17, IL6 and sRANKL, R&D Systems; C-terminal telopeptides of type I collagen, Nordic Bioscience Diagnostics AIS) according to the manufactures' instructions. To measure total TGFβ, acid-treated samples were analyzed using a kit (Promega) according to the manufacture's instruction. For the analysis of immunoglobulins, the samples were incubated on wells coated with anti-mouse immunoglobulins antibody (10 µg/ml, Invitrogen), followed by the treatment using Mouse Mono-AB ID/SP kit (Invitrogen) according to the manufacture's protocols. The results were averaged in each group. The intra-group differences were calculated between the mean values.

Clinical Tests for Urine Protein.

Urine samples were collected from SLE patients and measured protein level in the urine in the Clinical Laboratory at the Drum Tower Hospital of Nanjing University Medical School.

Histological Analysis of Kidney, Liver and Spleen.

Kidney, liver and spleen were harvested from mice and fixed. The sections were used for further experiments. Samples were fixed with 4% PFA for 24 hours at 4° C., and embedded with paraffin or Tissue-Tek O.C.T. compound (Sakura). Paraffin Sections were used for fl&E staining, trichrome staining, Periodic Acid Schiff (PAS) staining and immunohistochemistry. Frozen sections were used for immunohistochemistry and Oil Red-O staining.

Histomorphometric analysis was quantified as described previously (Shi et al., *Nat Biotechnol* 2002; 20:587-591; Miura et al., *Proc Natl Acad Sci USA*. 2005; 102: 14022-14027). Area of trabecular bone and bone marrow was measured on H&E stained slides. To quantify osteoclast activity in the bones, number of mature osteoclasts was determined by TRAP positive cells that attached on the bone surface. Osteoblastic niche was quantified by the number of osteoblasts lining on the bone surface per bone marrow area with H&E staining. Quantification of newly-formed bone and marrow area was measured on transplant sections with H&E staining. The number of cells and the area were measured from five to seven representative images each sample using an NIH Image-J. The data were average the means in each experimental group. The results were shown as each indicated percentage.

CD4$^+$ T Lymphocyte Isolation.

CD4$^+$ T lymphocytes were isolated from mouse spleen using a magnetic sorter and mouse CD4$^+$ T lymphocyte isolation kit (Miltenyi Biotec) following manufacture's instruction. The purity of the CD4$^+$ T cells was >95%.

Flow Cytometric Analysis.

Flow cytometric staining and analysis were performed as previously reported (see above in Experiment 1). Mouse spleen cells and spleen-derived CD4$^+$T lymphocytes were used for cytometric analysis. For analysis in SLE patients (n=4), peripheral blood mononuclear cells were separated using 2 m peripheral blood samples by Ficoll-Hypaque density centrifugation. For Treg staining, cells ($1 \times 10^6$/ sample or subject) were stained with APC-conjugated anti-CD25 antibody in mouse samples and APC-conjugated anti-CD4 antibody in human samples for 30 minutes under the shield at 4° C., followed by staining with PE-conjugated anti-Foxp3 antibody using Foxp3 Staining Buffer Set (eBioscience) according to the manufacture's protocol for cell fixation and permeabilization. Cells isolated from spleen and bone marrow were stained with PE-conjugated anti-CD138 antibody. The samples were analyzed in a flow cytometer. For Th17 cell staining, cells ($1\times10^6$/sample) were incubated with PerCP-conjugated anti-CD4 antibody. After cell fixation and permeabilization, cells were stained with PE-conjugated anti-IL17 antibody.

Statistical Analysis.

Student's t-test was used to analyze significance between two groups. P value of less than 0.05 was considered as a significant difference.

Experiment 3

3.1 SHED Possess Mesenchymal Stem Cell Properties.

Although SHED are capable of differentiating into a variety of cell types, their detailed mesenchymal stem cell properties remain to be elucidated. Herein, we used flow cytometry, immunoblot analysis, and immunocytostaining analysis to demonstrate that SHED at passage 3 expressed many mesenchymal surface markers, including STRO-1, stage specific embryonic antigen 4 (SSEA4), CD73, CD105, CD146, and CD166 but were negative for CD34 and CD45 (FIGS. 13A-C). In comparison to BMMSCs, SHED expressed higher levels of STRO-1 and CD146, and lower levels of CD105 (FIG. 13A). Additionally, SHED showed significantly high numbers of CFU-F and an elevated cell proliferation rate compared to BMMSCs (FIGS. 13D and 13E). This elevated proliferative capacity may be associated with the significantly increased telomerase activity in SHED (FIG. 13F).

To compare osteogenic differentiation of SHED with BMMSCs, multiple colony-derived SHED at passage 3 were supplemented with L-ascorbate-2-phosphate, dexamethasone, and inorganic phosphate to induce mineralization in vitro as described previously (Shi et al., *Nat Biotechnol* 2002; 20:587-591). After 1 week of induction, SHED were similar to BMMSCs, showing significantly increased ALP activity (FIG. 14A) and the number of ALP-positive cells by flow cytometric analysis (FIG. 14B), and expression of elevated levels of ALP, Runt related transcription factor 2 (Runx2), dentin sialoprotein (DSP), and OCN by immunoblot analysis (FIG. 14C). Alizarin Red-positive nodule formation in SHED and BMSMC cultures was notified after 4 weeks of osteogenic induction, indicating calcium accumulation in vitro (FIGS. 14D and 14E). However, SHED suffered remarkable impairment of adipogenic differentiation, as shown by decreased numbers of lipid-specific Oil red O-positive cells and reduced expression of adipocyte-specific molecules, PPARγ2 and LPL when compared to BMMSCs (FIGS. 14F-H). To validate the capacity of forming mineralized tissue in vivo by SHED, ex vivo expanded-SHED were transplanted into immunocompromised mice with HA/TCP as a carrier. SHED formed a similar amount of mineralized tissue and a reduced amount of bone marrow components when compared to BMMSC transplants (FIGS. 14I-K). Next, we confirmed that SHED were similar to BMMSCs in activation of multiple signaling pathways, including transforming growth factor beta (TGFβ), extracellur signal-related kinase (ERK), Akt, Wnt, and platelet-derived growth factor (PDGF) (FIGS. 14L-P).

3.2 Interplays Between SHED and T-Iymphoeytes.

In order to compare the immunomodulatory capacity of SHED with BMMSCs, anti-CD3/CD28 antibodies with TGFβ/IL-6 were added to the co-cultures of SHED or BMMSCs with naïve T cells, which were purified from human PBMNCs, levels of IL17$^+$IFNg$^-$ Th17 cells and IL17 were significantly reduced in SHED and BMMSC groups compared to the naïve T cell group (FIG. 15A). It appeared that SHED showed a significant inhibiting effect in reducing IL17 levels when compared to BMMSCs (FIG. 15B). Our previous report indicated that activated T cells induce apoptosis of BMMSCs through the Fas/FasL pathway (Yamaza et al., *PLoS ONE* 2008, 3(7):e2615). To determine whether activated T cells also directly impinge on SHED, as occurs in BMMSCs, SHED were co-cultured with human PBMNCs activated by anti-CD3 specific antibody treatment. We found that the activated PBMNCs were able to induce part of SHED death in the co-culture system (FIG. 15C). When SHED were separated from PBMNCs using a transwell co-culture system or treated using anti-FasL neutralizing antibody, SHED failed to show the cell death (FIG. 15C), suggesting that direct cell-cell contact and the Fas/FasL pathway are required for inducing SHED death by activated splenocytes. Next, we confirmed that SHED express Fas by immunoblot analysis (FIG. 15D). Terminal deoxynucleotidyl transferase-mediated dUTP-biotin nick end labeling (TUNEL) staining was used to confirm that the SHED death was due to cell apoptosis (FIG. 15E).

3.3 SHED Transplantation Improves SLE Phenotypes in MRL/Lpr Mice.

The inventors have previously showed that systemic infusion of BMMSCs offers appropriate treatment for SLE disorders in human patients and SLE-like MRL/lpr mice. Here we selected SLE-like mice at 16 weeks of age to infuse SITED for treating SLE disorders using BMMSCs as a control (FIG. 16A). It is known that autoantibodies play a crucial role in SLE patients. Our previous study showed a remarkable increase in the levels of autoantibodies including anti-dsDNA IgG and IgM antibodies, and ANA in the peripheral blood. As seen in BMMSC transplantation, SHED transplantation resulted in a significant reduction in serum levels of anti-dsDNA IgG and IgM, and ANA antibodies (FIGS. 16B-D).

Histological analysis with hematoxylin and eosin, trichrome, and periodic acid-Schiff staining revealed that SHED transplantation was similar to BMMSC transplantation in recovery of SLEassociated renal disorders, such as nephritis with glomerular basal membrane disorder and messangial proliferation in MRL/lpr mice (FIG. 16E). An ELISA data showed that SHED and BMMSC transplantation was able to reduced the urine C3 level and elevate the serum C3 level (FIG. 16F). Also, SHED transplantation significantly reduced urine protein levels compared to BMMSC transplantation (FIG. 16G), Moreover, SHED and BMMSC transplantation significantly elevated creatinine levels in urine and reduced creatinine levels in serum (FIG. 16H). This experimental evidence indicated that SHED transplantation is an effective approach for treating SLE disorders.

3.4 SHED Transplantation Regulates Ratio of Regulatory T Cells (Tregs) and Th17 Cells.

Tregs prevent pathogenic autoimmunity by suppressing proliferation and production of pro-inflammatory cytokines in effector immune cells, such as helper T-lymphocytes. In contrast, Th17 cells that produce IL17 are inflammatory cells responsible for the pathogenesis of autoimmune diseases and bone destruction. The inventors have previously shown that BMMSC transplantation affects the immune balance between Tregs and Th17 cells in SLE-like disorders. Here it was discovered that SHED transplantation showed more significant effect in up-regulating the ratio of Treg and Th17 cells in comparison to BMMSC transplantation in MRL/lpr mice (FIGS. 17A-C). Both SHED and BMMSC transplantations showed no significant changes in the level of IL10 and IL6 in MRL/lpr mice (FIGS. 17D and 17E); however, SHED transplantation provided a remarkably reduction of Th17 cells and IL17 level in MRL/lpr mice when compared to BMMSC transplantation (FIGS. 17C and 17F).

The inventors have found in a previous study that BMMSC transplantation-mediated therapy in SLE-like mice may associate with the reconstructing trabecular bone, however, it was not known whether this property would extent to other cell lines (Sun et at, Stem Cells. 2009; 27(6):1421-32), In this experiment, the inventors discovered that SHED were also capable of reconstructing trabecular bone in MRL/lpr mice (FIG. 18A). In contrast to BMMSC/osteoblast lineage, osteoclasts play a significant role in the maintenance of bone homeostasis by the bone resorption function. The inventors compared SHED transplantation with BMMSC transplantation in inhibiting osteoclast activity in MRL/lpr mice and found that both SHED and BMMSC transplantation were able to reduce the number of TRAP-positive osteoclasts in the distal femur epiphysis of MRL/lpr mice (FIG. 18B), serum levels of sRANKL, a critical factor for osteoclastogenesis (FIG. 18C), and bone resorption marker C-terminal telopeptides of type I collagen (FIG. 18D) as compared to untreated MRL/lpr mice.

Materials and Methods

Mice.

C57BL/6J and C3MRL-Faslpr/J (MRL/lpr) mice (female, 6-7 week-old) were purchased from the Jackson Laboratory. Beige Nude XidIII (nu/nu) mice (female, 8-12 week-old) were purchased from Harlan (Indianapolis). All animal experiments were performed under an institutionally approved protocol for the use of animal research (University of Southern California protocol #10874 and #10941). The mice were maintained in a temperature-controlled room with a 12-h alternating light-dark cycle and fed sufficient diet and water ad libitum throughout the experimental period.

Human Tooth, Bone Marrow and Peripheral Blood Samples.

Human exfoliated deciduous incisors were obtained as discarded biological samples from children (6-8-year-old) at Dental Clinic of University of Southern California following the approved Institutional Review Board guidelines. Healthy bone marrow aspirates from iliac bone and peripheral blood mononuclear cells (PBMNCs) of healthy volunteers were purchased from AllCells (Barkley, Calif.).

Isolation and Culture of SHED and BMMSCs.

Mononuclear cells (MNCs) isolated from the remnant dental pulp tissue of the deciduous incisors were cultured as reported previously (Miura et al., *Proc Natl Acad Sci USA* 2003, 100: 5807-5812). BMMSCs culture was described previously (Shi et al., *Nat Biotechnol* 2002, 20:587-591; Miura et al., *Proc Natl Acad Sci USA*. 2005; 102: 14022-14027). Minced remnant dental pulp tissue was digested in a fresh enzyme mixture. The enzyme solution contained 0.2% collagenase type I (Worthington Biochemicals Corp) and 0.1% dispase II (Roche Diagnostic/Boehringer Mannheim Corp.) in phosphate buffered saline (PBS). After incubation for 60 mM at 37° C., MNCs were obtained. Lymphocyte fraction was separated from bone marrow using a density gradient media Ficoll-PlaqueTmPLUS (GE Healthcare Bioscience). MNCs were passed through a 70-μm cell strainer (BD Bioscience). The single cell suspension of MNCs ($1\times10^6$) was seeded on T-75 culture flasks (Corning), and cultured at 37° C. in 5% $CO_2$ in a growth medium. The growth medium contained αMEM (Invitrogen) supplemented with 15% fetal calf serum (Equitech-Bio Inc.), 100 μM L-ascorbic acid 2-phosphate (WAKO Pure Chemical Industries, Ltd.), 2 mM L-glutamine (Invitrogen), 100 U/ml penicillin and 100 μg/ml streptomycin (Invitrogen). After 3 hours, non-adherent cells were removed by washing with PBS, and the adherent cells were cultured. Colonies forming cells were recognized as stem cell culaters. The cells were passed and sub-cultured. For xenogenic stem cell transplantation (MSCT), SHED and BMMSCs were cultured under non-serum-depleted condition for 12 hours prior to MSCT, and repeatedly washed with physiological saline.

Cell Surface Markers Analysis.

The procedure for single colored flow cytometry was performed as described previously (Shi et al., *Nat Biotechnol* 2002, 20:587-591)=Passage 1 stem cells were cultured under the growth medium. Single-cell suspensions ($2\times10^5$/100 μl per each marker) were incubated with mouse monoclonal antibodies specific to cell surface markers (each 1 μg/100 μl) for 45 min on ice, followed by reaction with R-phycoerythrin (PE) conjugated goat antibodies against mouse IgM or IgG (each 1 μg/100 μl, Southern Biotechnology) for 30 min on ice. As negative controls, isotype-matched mouse immunoglobulins ($IgG_1$, $IgG_{2a}$ and IgM) (each 1 μg/100 μl, Southern Biotechnology) were incubated instead of the primary antibodies. The samples were analyzed on a FACScamur flow cytometer (BD Bioscience, San Jose, Calif.). Some cells were used for immunoblot analysis and immunofluorescent staining.

Immunofluorescent Microscopy.

The cells subcultured on 8-well chamber slides (Nunc) ($2\times10^4$ per well) under the growth medium were fixed with 4% PFA (Merck), and blocked with normal serum matched to secondary antibodies. The samples were incubated with the specific antibodies to cell surface markers or isotype-matched mouse antibodies (1:50) overnight at 4° C., and treated with Rhodamin-conjugated secondary antibodies (1:200, Jackson ImmunoResearch, Southern Biotechnology). Finally, they were mounted by means of a Vectaseald mounting medium containing 4',6-diamidino-2-phenylindole (DAPI) (Vector Laboratories, Burlingame, Calif.).

CFU-F assay. CFU-F assay was performed according to previous study (Miura et al., *J Clin Invest* 2004; 114:1704-1713). MNCs ($10\times10^3$ per flask) were seeded and incubated on T-25 culture flasks (Nunc) for 3 hours at 37° C. The flasks were washed with PBS twice to remove and non-adherent cells. Adherent cells on the flasks were cultured for 16 days in the growth medium, and stained with a fix/stain solution containing 0.1% toluidine blue (Merck) and 2% PFA (Merck) in PBS. Colonies containing >50 cells were recognized as single colony clusters under a microscope, and the colony numbers were counted.

Cell Proliferation Assay.

The proliferation of each MSC population was performed by BrdU incorporation assay as previously described (Miura et al., *J Clin Invest* 2004; 114:1704-1713). SHED and BMMSCs ($1\times10^3$ per well) were seeded on 2-well chamber slides (Nuns) and cultured in the growth medium. After one to two days, BrdU reagent (1:100, Invitrogen) was added in the cultures. After 24 hours, incorporated BrdU were stained with the BrdU staining kit (Invitrogen), following the manufacture's instruction, followed by hematoxylin staining. To quantify proliferation capacity of the cells, ten representative images were used to calculate BrdU-positive nuclei number. Cell proliferation capacity was shown as a percentage of BrdU-positive nuclei over total nucleated cells.

Telomerase Activity Assay.

Telomerase activity was evaluated by telomeric repeat amplification protocol (TRAP) assay using real-time polymerase chain reaction (PCR) (Yamaza et al., *PLoS ONE* 2008, 3(7):e2615). To measure telomerase activity, TRAP assay was examined using the quantitative telomerase detection (QTD) kit (Allied Biotech) according to the manufactures' protocol. Briefly, P1 SHED or BMMSCs ($100\times10^3$) cultured in the growth medium were mixed with 2xQTD pre-mix containing telomere primers (TTAGGG) and iQ™SYBR® Green Supermix (BioRad Laboratories), and detected with an iCycler iQ® real-time PCR Detection System (BioRad Laboratories). As positive control, HEK293T cells were used. The extracts were heated at 85° C. for 10 min, and used as negative control. The real-time PCR condition was as follows: telomerase reaction for 20 min at 25° C., PCR initial activation step for 3 min at 95° C., 3-step cycling; denaturation for 10 sec at 95° C., annealing for 30 sec at 60° C., extension for 3 min at 72° C., and cycle number was 40.

In Vitro Osteogenic Induction Assay.

Osteogenic differentiation assay of SHED and BMMSCs were performed according to previous publications (Miura et al., *Proc Natl Acad Sci USA* 2003, 100: 5807-5812; Yamaza et al., *PLoS ONE* 2008, 3(7):e2615). SHED or BMMSCs ($500\times10^3$ per dish) were seeded on 100-mm dishes (Corning) and cultured in the growth medium until the cells reached at confluent condition. To induce osteogenic condition, the medium was changed to an osteogenic medium. The growth medium supplemented with 1.8 mM potassium dihydrogen phosphate (Sigma, St. Louis, Mo.) in the presence or absence of 10 nM dexamethasone (Sigma) was used as an osteogenic medium. Osteogenic markers and mineralized nodule formation were assessed as described previously (Miura et at, *Proc Natl Acad Sci USA* 2003, 100: 5807-5812; Yamaza et at, *PLoS ONE* 2008, 3(7):e2615). One weeks after the osteogenic induction, osteo genic markers were analyzed by colormetry, flow cytometry, and immunoblot analysis. To measure ALP activity by colormetry, cultured MSCs were washed three times with PI35 and collected for ALP activity analysis using Basic phospha-B test (Wako Pure Chemical) according manufactures' instruction and quantified the absorbance spectrophotometrically at $OD_{405}$. Total cellular protein was determined by using BCA protein assay kit (Pierce, Rockford, Ill.). ALP expression was also analyzed by flow cytometry. Extracted total protein two weeks post osteogenic induction was used to analyze the expression of osteoblastic specific markers by immunoblotting. For mineralized nodule assay, cultured MSCs were stained with 1% alizarin red-S (Sigma) in distilled water at 4 weeks post induction. The alizarin red-positive area was analyzed using NIH image software Image-J and shown as a percentage of alizarin red-positive area over total area.

Adipogenic Induction Assay In Vitro.

Adipogenic assay in vitro of each stem cell population was performed as described previously (Miura et at, *Proc Natl Acad Sci USA* 2003, 100: 5807-5812, Yamaza et al., *PLoS ONE* 2008, 3(7):e2615). Cells cultured until the confluent condition were induced in an adipogenic medium with the growth medium plus 500 µM isobutyl-methylxanthine (Sigma), 60 µM indomethacin (Sigma), 0.5 µM hydrocortisone (Sigma), and 10 µM insulin (Sigma) for three weeks. Some cultures were stained with 0.3% Oil-red-O (Sigma) to detect lipid droplets. The number of Oil-red O-positive droplets-containing cells were counted and shown as a percentage of Oil-red O-positive cells over total cells. Total protein was also extracted and analyzed adipocyte-specific markers by immunoblotting.

In Vivo Osteogenic Differentiation.

Xenogeneic transplantation was performed using immunocompromised mice as described (Miura et al., *Proc Natl Acad Sci USA* 2003, 100: 5807-5812; Yamaza et al., *Blood* 2009, 113(11):2595-2604; Shi et al., *Nat Biotechnol* 2002, 20:587-591). Each MSC population was subcutaneously transplanted into beige Xid (III) (nu/nu) mice using HA/TCP as a carrier. Eight weeks post-transplantation, the transplants were harvested for histological analysis. MSCs ($4.0\times10^6$) were mixed with hydroxyapatite/tricalcium phosphate (HA/TCP) ceramic powders (40 mg, Zimmer Inc., Warsaw, Ind.). The mixture was implanted subcutaneously into the dosal surface of 8-10-week-old beige nu/nu Xid (III) immunocompromised mice were used for in vivo transplantation experiments under the approved animal protocol of USC (#10874). The transplants were harvested 8 weeks after the implantation. For Histological analysis, the tissue samples were fixed with 4% PFA in PBS and decalcified with 5% EDTA solution (pH 7.4). The paraffin sections were stained with hematoxylin and eosin (H&E) and analyzed by Image. Seven fields were selected and newly-formed mineralized tissue and newly formed bone marrow-like tissue area within each field was calculated and shown as a percentage of each tissue area over total tissue area.

Immunoblot Analysis.

Ten µg total protein was loaded and analyzed by immunoblotting as previously described (Miura et al., *Proc Natl Acad Sci USA* 2003, 100: 5807-5812, Yamaza et al., *PLoS ONE* 2008, 3(7):e2615). Cells were lysed in M-PER® mammalian protein extraction reagent (Pierce). Ten µg of total protein were applied and separated on 4-12% NuPAGE® gel (Invitrogen) and transferred on Immobilon™-P membranes (Millipore Corporation, Bedford, Mass.). The membranes were blocked with 5% non-fat dry milk and 0.1% Tween 20 for 1 h, followed by incubation with the primary antibodies (1:100-1000 dilution) at 4° C. overnight. They were treated with horseradish peroxidase-conjugated rabbit or mouse IgG (Santa Cruz) (1:10,000) for 1 h, enhanced with a SuperSignal® West Pico Chemiluminescent Substrate (Pierce), and exposured on BIOMAX MR films (Kodak).

Co-Culture of Human PBMNCs or T Lymphocytes with SHED or BMMSCs.

Human PBMNCs purchased from All Cells (Buckley, Calif.) were used as naïve PBMNCs. Human $CD4^+CD25^-$ naïve T lymphocytes were purified by negative selection from naïve splenocytes using a $CD4^+CD25^+$ regulatory T cell isolation kit (Miltenyi Biotec, Aubun, Calif.) according to the manufacture's instruction with MACS LD and LS columns (Miltenyi Biotec) and a magnetic separator Midi-MACS (Miltenyi Biotec). The naïve PBMNCs and naïve T lymphocytes (each $1\times10^6$ per well) were cultured on 24-well multi-plates (Corning) under a complete medium. The complete medium contained Dulbecco's Modified Eagle Medium (DMEM) supplemented with 10% heat-inactivated FBS, 2 mM L-glutamine, 50 mM 2-mercaptoethanol, 100 U/ml penicillin and 100 µg/ml streptomycin.

Survival Assay of SHED Co-Cultured with Splenocytes.

MSCs ($200\times10^3$ per well) were plated in 24-well flat-bottom plates (Corning), and cultured for 3 days. Activated PBMNCs ($1\times10^6$) were loaded directly on MSCs or indirectly interacted with MSCs using transwell system (Corning). The cells were co-cultured in DMEM-based medium in the absence or presence of anti-FasL antibody (1 µg/ml). After three days, the wells were washed by PBS and stained using a fix/staining solution containing 2% PFA and 2% toluidine blue or an ApopTag Peroxidase In Situ Apoptosis Detection kit (Millipore) to detect apoptotic cells. To quantify cell death, ten representative images were used for counting positive nuclei number. Apoptotic cells were shown as a percentage of positive nuclei over total nucleated cells.

Tregs and Th17 Induction Assay Co-Cultured with MSCs.

$CD4^+CD25^-$ T-lymphocytes (naïve T lymphocytes, naïve T cells) ($1\times10^6$ per well) were pre-cultured on 24-well multiplates under the complete medium in the presence of plate bounded anti-CD3ε antibody (5 µg/ml) and soluble anti-CD28 antibody (2 µg/ml) for 3 days. MSCs (SHED and BMMSCs) ($20\times10^3$ per well) were also seeded on other plates and cultured under the growth medium for 3 days. MSC culture ware washed with complete medium twice. The activated T-lymphocytes ($1\times10^6$ per well) were loaded on the MSC cultures, and co-cultured in the complete medium with or without recombinant human TFGβ1 (2 ng/ml) (R&D Systems) and recombinant human IL2 (2 ng/ml) (R&D Systems) or recombinant human TGFβ1 (2 ng/ml) and recombinant human IL6 (50 ng/ml) (R&D Systems) for Tregs or Th17 induction. After 3.5 days, floating cells and culture medium were collected and centrifuged. The cells were used for to analyze Tregs and Th17 levels by flow cytometer, and the supernatant was used to measure IL10 level by enzyme-linked immunosorbent assay (ELISA).

Xenogeneic SHED or Human BMMSCs Transplantation into MRL/Lpr Mice.

Under general anesthesia, SHED or BMMSCs ($1\times10^5$ cells/10 g body weight in 100 µl PBS) were infused into MRL/lpr mice via tail vein at 16 weeks (n=3) MRL/lpr mice (16-week-old) received physiological saline (n=3) were used as experimentally control mice. All mice were sacrificed at 20 weeks of age, and collected peripheral blood, kidney, and long bones (femur and tibiae).

Flow Cytometric Analysis of Treg and Th17 Cells.

Flow cytometric staining and analysis were performed as previously reported (Liu et al., *Stem Cells* 2008, 26 (4): 1065-1073). For Treg staining, cells ($1\times10^6$) were treated with PerCP-conjugated anti-CD4, fluorescein isothiocyanate (FITC)-conjugated anti-CD8a, allophycocyanin (APC)-conjugated anti-CD25 antibodies (each 1 µg/ml) for 45 min on ice under shield. They were stained with R-phycoerythrin (PE)-conjugated anti-Foxp3 antibody (1 µg/ml) using a Foxp3 staining buffer kit (eBioscience) for cell fixation and permeabilization according to the manufacture's protocol. For Th17 staining, cells ($1\times10^6$) were incubated with PerCP-conjugated anti-CD4, FITC-conjugated anti-CD8a, followed by the treatment with R-PE-conjugated anti-IL17 and APC-conjugated anti-IFNγ antibodies (each 1 µg/ml) using a Foxp3 staining buffer kit. The cells were then sorted on a FACS$^{Calibur}$ flow cytometer (BD Bioscience).

Measurement of Biomarkers in Culture Supernatant, Blood Serum and Urine.

Several biomarkers, including anti-dsDNA antibody and anti-nuclear antibody ANA, C3, IL6, IL10, IL17, sRANKL, and C-terminal telopeptides of type I collagen, creatinine, urine protein in biofluid samples (peripheral blood serum and urine) were measured by ELISA. Culture supernatant was collected from the co-culture of SHED or BMMSCs with activated naïve T cells. Blood serum was obtained from the peripheral blood collected from the retro-orbital plexus of mice. Urine was also collected from mice. All of the samples were stored at $-20°$ C. until used and re-centrifuged before the application for ELISA. Anti-dsDNA IgG and IgM antibodies, ANA, C3, IL6, IL10, IL17, sRANKL and C-terminal telopeptides of type I collagen were measured using commercial available kits (anti-dsDNA antibodies, ANA, albumin, C3, alpha diagnostic; IL6, IL10, IL17 and sRANKL, R&D Systems; C-terminal telopeptides of type I collagen, Nordic Bioscience Diagnostics AIS) according to the manufactures' instructions. Creatinine levels were assayed using a commercial kit (R&D Systems). The urine protein concentration was measured using a Bio-Rad Protein Assay (Bio-Rad). The results were averaged in each group. The intra-group differences were calculated between the mean values.

Histological Analysis of Kidney and Bone.

Kidneys and long bones (femurs) harvested from mice were fixed with 4% PFA phosphate buffered saline (PBS), pH 7.2, for 24 hours at 4° C. and processed to make paraffin sections. Femurs and transplant tissue were decalcified with 5% EDTA (pH 7.4) in PBS for 10 days at 4° C. after the fixation. Samples were dehydrated with a graduate series of ethanol, cleaned with xylen, and immersed in paraffin. The samples were embedded in paraffin and cut into 8-µm-thick sections. Paraffin Sections were used for hematoxylin and eosin (H&E) staining, trichrome staining, and Periodic Acid Schiff (PAS) staining, and further histochemical staining.

Trap Staining.

Some deparaffinized sections were re-fixed with a mixture of 50% ethanol and 50% acetone for 10 min. TRAP-staining solutions were freshly made (1.6% naphthol AS-BI phosphate in N,N-dimethylformamide and 0.14% fast red-violet LB diazonium salt, 0.097% tartaric acid and 0.04% $MgCl_2$ in 0.2 M sodium acetate buffer, pH 5.0) and mixed in 1:10. The sections were incubated in the solution for 10 min at 37° C. under shield and counterstained with toluidine blue. All regents for TRAP staining were purchased from Sigma. Air-dryed sections were covered to observe under a light microscope.

Histomorphomety.

Histomorphometric analysis was quantified as described previously (Yamaza et al., *Blood* 2009, 113(11):2595-2604). Area of trabecular bone and bone marrow was measured on hematoxylin and eosi (H&E) stained slides. To quantify osteoclast activity in the bones, number of mature osteoclasts was determined by TRAP-positive cells that attached on the bone surface. Osteoblastic niche was quantified by the number of osteoblasts lining on the bone surface per bone marrow area with H&E staining. Quantification of newly-formed bone and marrow area was measured on H&E staining sections of transplant tissue. The number of cells and the area were measured from five to seven representative images each sample using an NIH Image-J. The data were average the means in each experimental group. The results were shown as each indicated percentage.

Statistics.

All data are expressed as the mean±standard deviation (SD) of, at least, triplicate determinations. Statistical difference between the values was examined by Student's t-test. The p values less than 0.05 were considered significant.

Antibodies and Primers.

All primary antibodies used in this study were described as below. Antiserum against STRO-1 was treated as reported previously (Shi et al., *Nat Bioteehnol.* 2002 20(6):587-91). Purified mouse anti-human CD3 $IgG_{2a}$, and anti-human CD28 IgG$_1$, anti-human CD34, anti-human CD45, and anti-human CD105 IgG$_1$, APC-conjugated rat anti-mouse CD25 IgG$_1$, FITC-conjugated rat anti-mouse CD8a IgG$_{2a}$, PerCP-conjugated rat anti-mouse CD4 IgG$_{2a}$, R-PE-conjugated mouse anti-human CD73, anti-human CD146 and anti-human CD166, rat anti-mouse IL17 IgG$_1$, and subclass matched control antibodies were from BD Bioscience. Purified hamster anti-mouse FasL IgG, APC-conjugated mouse anti-human CD25 IgG$_1$, anti-human IFNγ IgG$_1$ and rat anti-mouse IFNγ IgG$_{2a}$, PerCP-conjugated mouse anti-human CD4 IgG$_1$, FITC-conjugated mouse anti-human CD8a IgG$_1$, R-PE-conjugated mouse anti-human Foxp3 and anti-human IL17, and rat anti-mouse Foxp3 IgG$_{2a}$, were obtained from eBioscience. Purified rabbit anti-mouse Akt, anti-phospholirated Akt (p-Akt), anti-human p-38, anti-p-p-38, anti-human p44/42 (ERK1/2), anti-human p-p44/42 (p-ERK1/2), anti-human p-Smad IgG antibodies were from Cell Signaling. Purified rabbit anti-human angiopoietin-1, anti-human Fas (CD95), anti-human PPARγ2, and anti-humna PDGF receptor β, anti-human TGFβ receptor I and anti-human TGFβ receptor II, and anti-mouse LPL IgG antibodies were obtained form Santa Cruz. Purified rabbit anti-human Runx2 IgG antibody was form Oncogene. Purified rabbit anti-human Smad2 IgG antibody was form Zymed. Rabbit anti-human N-cadherin IgG was form IBL. Purified rabbit anti-human β-cathenin IgG and mouse anti-human β-actin IgG$_1$ antibodies were purchased from Sigma. Purified rabbit anti-human ALP (LF-47) and anti-human OCN (LF-32) and mouse anti-mouse DSP (LF-21) IgG antibodies were gifted from Dr. Larry Fisher (National Institute of Dental and Craniofacial Research, National Institutes of Health, Bethesda, Md., USA).

What is claimed is:

1. A method for treating an SLE-like autoimmune disease in a human subject, consisting of administering subcutaneously to the human subject with an SLE-like autoimmune disease a disease activity reducing amount of a composition comprising stem cells from human exfoliated deciduous teeth (SHED) and, following administration of the SHED, administering an osteoblastic niche reconstruction effective amount of erythropoietin (EPO) to said human subject, wherein the SHED are allogenic SHED; wherein disease activity is reduced without the use of high dose immunosuppressive maintenance therapy; and wherein the allogenic SHED are obtained using a method that comprises:
   obtaining an allogenic human deciduous tooth;
   isolating dental pulp tissue from the human deciduous tooth;
   isolating single cells from the dental pulp tissue; and
   culturing single cells to obtain the allogenic SHED that express surface markers STRO-1, stage specific embryonic antigen 4 (SSEA4), CD73, CD105, CD146, and CD166, but are negative for CD34 and CD45.

2. The method of claim 1, wherein said SLE-like autoimmune disease is one selected from rheumatoid arthritis, systemic sclerosis, dermatomyositis complex, polymyositis, polyarteritis nodosa, or a combination thereof.

3. The method of claim 1, wherein said subject is one who is refractory to a standard treatment of said disease.

4. The method of claim 1, wherein said allogenic SHED in said composition are a non-attached suspension, attached to a substrate suitable for bone grafting, or combinations thereof.

5. The method of claim 1, wherein the SLE-like autoimmune disease is (systemic lupus erythematosus) SLE.

6. The method of claim 1, wherein said allogenic SHED are derived from a healthy family member of the human subject and ex vivo expanded in culture.

7. The method of claim 1, wherein said human subject is one who has an SLE-like disease and is refractory to a treatment by CTX and/oi glucocorticoid.

8. The method of claim 1, wherein said allogenic SHED are administered at $\geq 1 \times 10^6$ cells/kg body weight of the subject.

9. The method of claim 1, wherein said allogenic SHED are unmodified.

10. The method of claim 1, wherein the lifespan and/or quality of life of the human subject is extended.

11. The method of claim 4, wherein said allogenic SHED in said composition are attached to a substrate suitable for bone grafting.

12. The method of claim 11, wherein the lifespan and/or quality of life of the human subject is extended.

13. The method of claim 6, wherein the lifespan and/or quality of life of the human subject is extended.

14. The method of claim 6, wherein said allogenic SHED in said composition are attached to a substrate suitable for bone grafting.

15. The method of claim 14, wherein the lifespan and/or quality of life of the human subject is extended.

* * * * *

UNITED STATES PATENT AND TRADEMARK OFFICE
CERTIFICATE OF CORRECTION

PATENT NO. : 10,098,333 B2
APPLICATION NO. : 13/133638
DATED : October 16, 2018
INVENTOR(S) : Songtao Shi et al.

Page 1 of 1

It is certified that error appears in the above-identified patent and that said Letters Patent is hereby corrected as shown below:

In the Specification

Column 1, Lines 21-25:
Please delete:
"This invention was made with goverment support under Contract No. ROIDEI 7449 and 1R01DE019413 awarded by National Institutes of Health and RNI-00572 awarded by the California Institute for Regenerative Medicine. The goverment has certain rights in the invention."

And insert:
--This invention was made with government support under grant numbers DE019413, R01 DE017449 awarded by the National Institutes of Health. The government has certain rights in the invention.--

Signed and Sealed this
Fourth Day of March, 2025

Coke Morgan Stewart
*Acting Director of the United States Patent and Trademark Office*